(12) United States Patent
Treon et al.

(10) Patent No.: US 10,525,060 B2
(45) Date of Patent: Jan. 7, 2020

(54) HCK AS A THERAPEUTIC TARGET IN MYD88 MUTATED DISEASES

(71) Applicant: Dana-Farber Cancer Institute, Inc., Boston, MA (US)

(72) Inventors: Steven P. Treon, Jamaica Plain, MA (US); Guang Yang, Natick, MA (US); Nathanael S. Gray, Boston, MA (US); Sara Jean Buhrlage, Somerville, MA (US); Li Tan, Shanghai (CN)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/581,736

(22) Filed: Apr. 28, 2017

(65) Prior Publication Data

US 2017/0333436 A1 Nov. 23, 2017

Related U.S. Application Data

(60) Provisional application No. 62/329,406, filed on Apr. 29, 2016.

(51) Int. Cl.
*A61K 31/519* (2006.01)
*A61K 45/06* (2006.01)

(52) U.S. Cl.
CPC ............ *A61K 31/519* (2013.01); *A61K 45/06* (2013.01)

(58) Field of Classification Search
CPC .............................. A61K 31/519; A61K 45/06
See application file for complete search history.

(56) References Cited

U.S. PATENT DOCUMENTS

| | | | |
|---|---|---|---|
| 2002/0156081 A1 | 10/2002 | Hirst et al. | |
| 2004/0137489 A1 | 7/2004 | Shaughnessy | |
| 2009/0156469 A1* | 6/2009 | Ghobrial | A61K 31/40 514/1.1 |
| 2010/0009350 A1 | 1/2010 | Chow | |
| 2010/0216115 A1 | 8/2010 | Yan et al. | |
| 2012/0065201 A1 | 3/2012 | Honigberg et al. | |
| 2012/0071497 A1 | 3/2012 | Buggy et al. | |
| 2014/0249142 A1 | 9/2014 | Treon | |
| 2015/0210698 A1 | 7/2015 | Ishikawa et al. | |
| 2016/0222465 A1 | 8/2016 | Treon et al. | |
| 2016/0304958 A1 | 10/2016 | Treon et al. | |

FOREIGN PATENT DOCUMENTS

| | | |
|---|---|---|
| EP | 2878601 A1 | 6/2015 |
| WO | WO 2006/067091 A1 | 6/2006 |
| WO | WO 2008/060367 A2 | 5/2008 |
| WO | WO 2013/006443 A2 | 1/2013 |
| WO | WO 2013/071068 A2 | 5/2013 |
| WO | WO 2015/038887 * | 3/2015 |

OTHER PUBLICATIONS

Extended European Search Report for EP12807230.3 dated Feb. 2, 2015.
Invitation to Pay Additional Fees for PCT/US2012/044956 dated Oct. 1, 2012.
International Search Report and Written Opinion for PCT/US2012/044956 dated Dec. 17, 2012.
International Preliminary Report on Patentability for PCT/US2012/044956 dated Jan. 16, 2014.
Extended European Search Report for EP14844516.6 dated Mar. 28, 2017.
International Search Report and Written Opinion for PCT/US2014/055386 dated Dec. 23, 2014.
International Preliminary Report on Patentability for PCT/US2014/055386 dated Mar. 24, 2016.
International Search Report and Written Opinion for PCT/US2014/068579 dated Mar. 3, 2015.
International Preliminary Report on Patentability for PCT/US2014/068579 dated Jun. 16, 2016.
Advani et al., Bruton tyrosine kinase inhibitor ibrutinib (PCI-32765) has significant activity in patients with relapsed/refractory B-cell malignancies. J Clin Oncol. Jan. 1, 2013;31(1):88-94. doi:10.1200/JCO.2012.42.7906. Epub Oct. 8, 2012.
Anderson et al., Multiple myeloma, version 1.2013. J Natl Compr Canc Netw. Jan. 1, 2013;11(1):11-7.
Arcaini et al., Distinctive clinical and histological features of Waldenström's macroglobulinemia and splenic marginal zone lymphoma. Clin Lymphoma Myeloma Leuk. Feb. 2011;11(1):103-5. doi:10.3816/CLML.2011.n.020.
Argentou et al., Rapid detection of MYD88-L265P mutation by PCR-RFLP in B-cell lymphoproliferative disorders. Leukemia. Feb. 2014;28(2):447-9. doi: 10.1038/leu.2013.294. Epub Oct. 18, 2013.
Argyropoulos et al., Clonal B cells in Waldenström's macroglobulinemia exhibit functional features of chronic active B-cell receptor signaling. Leukemia. May 2016;30(5):1116-25. doi:10.1038/leu.2016.8. Epub Feb. 12, 2016.
Balabanian et al., WHIM syndromes with different genetic anomalies are accounted for by impaired CXCR4 desensitization to CXCL12. Blood. Mar. 15, 2005;105(6):2449-57. Epub Nov. 9, 2004.
Bam et al., Role of Bruton's tyrosine kinase in myeloma cell migration and induction of bone disease. Am J Hematol. Jun. 2013;88(6):463-71. doi: 10.1002/ajh.23433. Epub Mar. 28, 2013.
Berger et al., Clinicopathologic features of Waldenstrom's macroglobulinemia and marginal zone lymphoma: are they distinct or the same entity? Clin Lymphoma. Mar. 2005;5(4):220-4. Abstract.
Bergsagel et al., Comprehensive identification of somatic mutations in chronic lymphocytic leukemia. Cancer Cell. Jul. 12, 2011;20(1):5-7. doi:10.1016/j.ccr.2011.06.023.
Bohers et al., Targetable activating mutations are very frequent in GCB and ABC diffuse large B-cell lymphoma. Genes Chromosomes Cancer. Feb. 2014;53(2):144-53. doi:10.1002/gcc.22126. Epub Nov. 5, 2013.

(Continued)

*Primary Examiner* — Sahar Javanmard
(74) *Attorney, Agent, or Firm* — Wolf, Greenfield & Sacks, P.C.

(57) ABSTRACT

Methods of treatment of conditions or diseases associated with myeloid differentiation primary response (MYD88) protein using a selective HCK inhibitor are provided herein.

15 Claims, 25 Drawing Sheets

Specification includes a Sequence Listing.

(56) References Cited

OTHER PUBLICATIONS

Brikos et al., Mass spectrometric analysis of the endogenous type I interleukin-1 (IL-1) receptor signaling complex formed after IL-1 binding identifies IL-1RAcP, MyD88, and IRAK-4 as the stable components. Mol Cell Proteomics. Sep. 2007;6(9):1551-9. Epub May 15, 2007.
Burger et al., B cell receptor signaling in Chronic lymphocytic leukemia. Trends Immunol. Dec. 2013;34(12):592-601. doi: 10.1016/j.it.2013.07.002. Epub Aug. 5, 2013.
Busillo et al., Regulation of CXCR4 signaling. Biochim Biophys Acta. Apr. 2007;1768(4):952-63. Epub Nov. 10, 2006.
Busillo et al., Site-specific phosphorylation of CXCR4 is dynamically regulated by multiple kinases and results in differential modulation of CXCR4 signaling. J Biol Chem. Mar. 5, 2010;285(10):7805-17. doi: 10.1074/jbc.M109.091173. Epub Jan. 4, 2010.
Cao et al., CXCR4 WHIM-like frameshift and nonsense mutations promote ibrutinib resistance but do not supplant MYD88(L265P)-directed survival signalling in Waldenström macroglobulinaemia cells. Br J Haematol. Mar. 2015;168(5):701-7. doi: 10.1111/bjh.13200. Epub Nov. 5, 2014.
Cao et al., The WHIM-like CXCR4(S338X) somatic mutation activates AKT and ERK, and promotes resistance to ibrutinib and other agents used in the treatment of Waldenstrom's Macroglobulinemia. Leukemia. Jan. 2015;29(1):169-76. doi: 10.1038/leu.2014.187. Epub Jun. 10, 2014.
Cao et al., Whole Genome Sequencing Identifies Recurring Somatic Mutations in the C-Terminal Domain of CXCR4, Including a Gain of Function Mutation in Waldenstrom's Macroglobinemia. Blood. 2012;120: Abstract 2715.
Carnevali et al., Computational techniques for human genome resequencing using mated gapped reads. J Comput Biol. Mar. 2012;19(3):279-92. doi: 10.1089/cmb.2011.0201. Epub Dec. 16, 2011.
Chen, Treatment for Waldenstrom's macroglobulinemia. Ann Oncol. Apr. 2004;15(4):550-8.
Cheng et al., Binding of Bruton's tyrosine kinase to Fyn, Lyn, or Hck through a Src homology 3 domain-mediated interaction. Proc Natl Acad Sci U S A. Aug. 16, 1994;91(17):8152-5.
Chng et al., Gene-expression profiling of Waldenstrom macroglobulinemia reveals a phenotype more similar to chronic lymphocytic leukemia than multiple myeloma. Blood. Oct. 15, 2006;108(8):2755-63. Epub Jun. 27, 2006.
Dave et al., Molecular diagnosis of Burkitt's lymphoma. N Engl J Med. Jun. 8, 2006;354(23):2431-42.
Davies et al., Preclinical pharmacology of AZD5363, an inhibitor of AKT: pharmacodynamics, antitumor activity, and correlation of monotherapy activity with genetic background. Mol Cancer Ther. Apr. 2012;11(4):873-87. doi: 10.1158/1535-7163.MCT-11-0824-T. Epub Jan. 31, 2012.
Ditzel et al., Establishment of BCWM.1 cell line for Waldenström's macroglobulinemia with productive in vivo engraftment in SCID-hu mice. Exp Hematol. Sep. 2007;35(9):1366-75.
Dotta et al., Clinical and genetic features of Warts, Hypogammaglobulinemia, Infections and Myelokathexis (WHIM) syndrome. Curr Mol Med. Jun. 2011;11(4):317-25.
Drmanac et al., Human genome sequencing using unchained base reads on self-assembling DNA nanoarrays. Science. Jan. 1, 2010;327(5961):78-81.
Evans et al., Inhibition of Btk with CC-292 provides early pharmacodynamic assessment of activity in mice and humans. J Pharmacol Exp Ther. Aug. 2013;346(2):219-28. doi:10.1124/jpet.113.203489. Epub May 24, 2013.
Farré et al., Identification of patterns in biological sequences at the ALGGEN server: PROMO and MALGEN. Nucleic Acids Res. Jul. 1, 2003;31(13):3651-3.
Futahashi et al., Separate elements are required for ligand-dependent and -independent internalization of metastatic potentiator CXCR4. Cancer Sci. Mar. 2007;98(3):373-9.

Gachard et al., IGHV gene features and MYD88 L265P mutation separate the three marginal zone lymphoma entities and Waldenström macroglobulinemia/lymphoplasmacytic lymphomas. Leukemia. Jan. 2013;27(1):183-9. doi: 10.1038/leu.2012.257. Epub Sep. 4, 2012.
Gay et al., Assembly and localization of Toll-like receptor signalling complexes. Nat Rev Immunol. Aug. 2014;14(8):546-58. doi: 10.1038/nri3713.
GENBANK Submission; NIH/NCBI, Accession No. NM_001008540. Micucci et al., Mar. 18, 2016.
Gertz et al., Waldenström's macroglobulinemia. Oncologist. 2000;5(1):63-7.
Gopal et al., PI3Kδ inhibition by idelalisib in patients with relapsed indolent lymphoma. N Engl J Med. Mar. 13, 2014;370(11):1008-18. doi: 10.1056/NEJMoa1314583. Epub Jan. 22, 2014.
Gutiérrez et al., Gene expression profiling of B lymphocytes and plasma cells from Waldenström's macroglobulinemia: comparison with expression patterns of the same cell counterparts from chronic lymphocytic leukemia, multiple myeloma and normal individuals. Leukemia. Mar. 2007;21(3):541-9. Epub Jan. 25, 2007.
Hallek et al., Signal transduction of interleukin-6 involves tyrosine phosphorylation of multiple cytosolic proteins and activation of Src-family kinases Fyn, Hck, and Lyn in multiple myeloma cell lines. Exp Hematol. Dec. 1997;25(13):1367-77.
Hanke et al., Discovery of a novel, potent, and Src family-selective tyrosine kinase inhibitor. Study of Lck- and FynT-dependent T cell activation. J Biol Chem. Jan. 12, 1996;271(2):695-701.
Harris et al., A revised European-American classification of lymphoid neoplasms: a proposal from the International Lymphoma Study Group. Blood. Sep. 1, 1994;84(5):1361-92.
Herman et al., Bruton tyrosine kinase represents a promising therapeutic target for treatment of chronic lymphocytic leukemia and is effectively targeted by PCI-32765. Blood. Jun. 9, 2011;117(23):6287-96. doi: 10.1182/blood-2011-01-328484. Epub Mar. 21, 2011.
Hodge et al., IL-21 in the bone marrow microenvironment contributes to IgM secretion and proliferation of malignant cells in Waldenstrom macroglobulinemia. Blood. Nov. 1, 2012;120(18):3774-82. doi: 10.1182/blood-2012-03-419440. Epub Sep. 13, 2012.
Hong et al., The Src family kinase Hck regulates mast cell activation by suppressing an inhibitory Src family kinase Lyn. Blood. Oct. 1, 2007;110(7):2511-9. Epub May 18, 2007. Erratum in: Blood. Mar. 15, 2008;111(6):3299.
Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010;107(29):13075-80. doi:10.1073/pnas.1004594107. Epub Jul. 6, 2010.
Hunter et al., Recurring activation mutations and somatic deletions revealed through whole genome sequencing in Waldenstrom's Macroglobulinemia. Hematol Oncol. Jun. 2013; 31(S1): Abstract 093.
Hunter et al., The genomic landscape of Waldenstrom macroglobulinemia is characterized by highly recurring MYD88 and WHIM-like CXCR4 mutations, and small somatic deletions associated with B-cell lymphomagenesis. Blood. Mar. 13, 2014;123(11):1637-46. doi:10.1182/blood-2013-09-525808. Epub Dec. 23, 2013.
Hunter et al., Use of whole genome sequencing to identify highly recurrent somatic mutations in Waldenström's macroglobulinemia. 2012 ASCO Annual Meeting. Jun. 1-Jun. 5. Chicago, Illinois: Abstract 8107.
Janz, Waldenström macroglobulinemia: clinical and immunological aspects, natural history, cell of origin, and emerging mouse models. ISRN Hematol. Sep. 9, 2013;2013:815325. doi: 10.1155/2013/815325.
Jeelall et al., Oncogenic MYD88 mutation drives Toll pathway to lymphoma. Immunol Cell Biol. Aug. 2011;89(6):659-60. doi: 10.1038/icb.2011.31. Epub Apr. 26, 2011.
Jiménez et al., MYD88 L265P is a marker highly characteristic of, but not restricted to, Waldenström's macroglobulinemia. Leukemia. Aug. 2013;27(8):1722-8. doi: 10.1038/leu.2013.62. Epub Feb. 28, 2013.

(56) References Cited

OTHER PUBLICATIONS

Jourdan et al., Characterization of a transitional preplasmablast population in the process of human B cell to plasma cell differentiation. J Immunol. Oct. 15, 2011;187(8):3931-41. doi:10.4049/jimmunol.1101230. Epub Sep. 14, 2011.

Juilland et al., CARMA1- and MyD88-dependent activation of Jun/ATF-type AP-1 complexes is a hallmark of ABC diffuse large B-cell lymphomas. Blood. Apr. 7, 2016;127(14):1780-9. doi:10.1182/blood-2015-07-655647. Epub Jan. 8, 2016.

Kawagoe et al., Sequential control of Toll-like receptor-dependent responses by IRAK1 and IRAK2. Nat Immunol. Jun. 2008;9(6):684-91.

Kiss et al., Comparative testing of peripheral blood and bone marrow for BCR-ABL transcripts in patients post allogeneic bone marrow transplantation and during interferon treatment for chronic myeloid leukemia. Leuk Lymphoma. Aug. 1999;34(5-6):493-500.

Kriangkum et al., Clonotypic IgM V/D/J sequence analysis in Waldenstrom macroglobulinemia suggests an unusual B-cell origin and an expansion of polyclonal B cells in peripheral blood. Blood. Oct. 1, 2004;104(7):2134-42. Epub Feb. 5, 2004.

Kyle et al., IgM monoclonal gammopathy of undetermined significance and smoldering Waldenström's macroglobulinemia. Clin Lymphoma Myeloma. Mar. 2009;9(1):17-8.

Kyle et al., Prognostic markers and criteria to initiate therapy in Waldenstrom's macroglobulinemia: consensus panel recommendations from the Second International Workshop on Waldenstrom's Macroglobulinemia. Semin Oncol. Apr. 2003;30(2):116-20.

Kyrtsonis et al., CD138 expression helps distinguishing Waldenström's macroglobulinemia (WM) from splenic marginal zone lymphoma (SMZL). Clin Lymphoma Myeloma Leuk. Feb. 2011;11(1):99-102. doi: 10.3816/CLML.2011.n.019.

Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.

Lam et al., Cooperative signaling through the signal transducer and activator of transcription 3 and nuclear factor-{kappa}B pathways in subtypes of diffuse large B-cell lymphoma. Blood. Apr. 1, 2008;111(7):3701-13. Epub Dec. 26, 2007.

Landgren et al., MYD88 L265P somatic mutation in IgM MGUS. N Engl J Med. Dec. 6, 2012;367(23):2255-6; author reply 2256-7. doi: 10.1056/NEJMc1211959#SA1.

Lee et al., The mutation spectrum revealed by paired genome sequences from a lung cancer patient. Nature. May 27, 2010;465(7297):473-7.

Leleu et al., Targeting NF-kappaB in Waldenstrom macroglobulinemia. Blood. May 15, 2008;111(10):5068-77.

Leleu et al., The Akt pathway regulates survival and homing in Waldenstrom macroglobulinemia. Blood. Dec. 15, 2007;110(13):4417-26. Epub Aug. 30, 2007.

Lin et al., Helical assembly in the MyD88-IRAK4-IRAK2 complex in TLR/IL-1R signaling. Nature. Jun. 17, 2010;465(7300):885-90.

Lin et al., Lymphoid neoplasms associated with IgM paraprotein: a study of 382 patients. Am J Clin Pathol. Feb. 2005;123(2):200-5.

Loiarro et al., Identification of critical residues of the MyD88 death domain involved in the recruitment of downstream kinases. J Biol Chem. Oct. 9, 2009;284(41):28093-103.

Loiarro et al., Peptide-mediated interference of TIR domain dimerization in MyD88 inhibits interleukin-1-dependent activation of NF-{kappa}B. J Biol Chem. Apr. 22, 2005;280(16):15809-14. Epub Mar. 8, 2005.

Loiarro et al., Pivotal Advance: Inhibition of MyD88 dimerization and recruitment of IRAK1 and IRAK4 by a novel peptidomimetic compound. J Leukoc Biol. Oct. 2007;82(4):801-10. Epub Jun. 4, 2007.

Martínez et al., Whole-exome sequencing in splenic marginal zone lymphoma reveals mutations in genes involved in marginal zone differentiation. Leukemia. Jun. 2014;28(6):1334-40. doi: 10.1038/leu.2013.365. Epub Dec. 3, 2013.

McDermott et al., A phase 1 clinical trial of long-term, low-dose treatment of WHIM syndrome with the CXCR4 antagonist plerixafor. Blood. Apr. 10, 2014;123(15):2308-16. doi:10.1182/blood-2013-09-527226. Epub Feb. 12, 2014.

McDermott et al., AMD3100 is a potent antagonist at CXCR4(R334X), a hyperfunctional mutant chemokine receptor and cause of WHIM syndrome. J Cell Mol Med. Oct. 2011;15(10):2071-81. doi: 10.1111/j.1582-4934.2010.01210.x.

McDermott et al., The CXCR4 antagonist plerixafor corrects panleukopenia in patients with WHIM syndrome. Blood. Nov. 3, 2011;118(18):4957-62. doi: 10.1182/blood-2011-07-368084. Epub Sep. 2, 2011.

McMaster et al., Long-term evaluation of three multiple-case Waldenstrom macroglobulinemia families. Clin Cancer Res. Sep. 1, 2007;13(17):5063-9.

Messeguer et al., PROMO: detection of known transcription regulatory elements using species-tailored searches. Bioinformatics. Feb. 2002;18(2):333-4.

Mueller et al., Hierarchical organization of multi-site phosphorylation at the CXCR4 C terminus. PLoS One. May 29, 2013;8(5):e64975. doi: 10.1371/journal.pone.0064975. Print 2013.

Musumeci et al., Hck inhibitors as potential therapeutic agents in cancer and HIV infection. Curr Med Chem. 2015;22(13):1540-64.

Ngo et al., Oncogenically active MYD88 mutations in human lymphoma. Nature. Feb. 3, 2011;470(7332):115-9. doi: 10.1038/nature09671.

Ngo et al., SDF-1/CXCR4 and VLA-4 interaction regulates homing in Waldenstrom macroglobulinemia. Blood. Jul. 1, 2008;112(1):150-8. doi: 10.1182/blood-2007-12-129395. Epub Apr. 30, 2008.

Ngo et al., Src tyrosine kinase regulates adhesion and chemotaxis in Waldenstrom macroglobulinemia. Clin Cancer Res. Oct. 1, 2009;15(19):6035-41. doi: 10.1158/1078-0432.CCR-09-0718. Epub Sep. 15, 2009.

O'Boyle et al., Open Babel: An open chemical toolbox. J Cheminform. Oct. 7, 2011;3:33. doi:10.1186/1758-2946-3-33.

Okada et al., Autopsy case of lymphoplasmacytic lymphoma with a large submucosal tumor in the stomach. Pathol Int. Oct. 2001;51(10):802-6.

Okuzumi et al., Inhibitor hijacking of Akt activation. Nat Chem Biol. Jul. 2009;5(7):484-93. doi:10.1038/nchembio.183. Epub May 24, 2009.

Ondrejka et al., MYD88 L265P somatic mutation: its usefulness in the differential diagnosis of bone marrow involvement by B-cell lymphoproliferative disorders. Am J Clin Pathol. Sep. 2013;140(3):387-94. doi: 10.1309/AJCP10ZCLFZGYZIP.

Owen et al., Clinicopathological definition of Waldenstrom's macroglobulinemia: consensus panel recommendations from the Second International Workshop on Waldenstrom's Macroglobulinemia. Semin Oncol. Apr. 2003;30(2):110-5.

Passamonti, How I treat polycythemia vera. Blood. Jul. 12, 2012;120(2):275-84. doi: 10.1182/blood-2012-02-366054. Epub May 18, 2012.

Patricelli et al., In situ kinase profiling reveals functionally relevant properties of native kinases. Chem Biol. Jun. 24, 2011;18(6):699-710. doi:10.1016/j.chembiol.2011.04.011.

Pecquet et al., The Src tyrosine kinase Hck is required for Tel-Abl—but not for Tel-Jak2-induced cell transformation. Oncogene. Mar. 8, 2007;26(11):1577-85. Epub Sep. 4, 2006.

Pene-Dumitrescu et al., An inhibitor-resistant mutant of Hck protects CML cells against the antiproliferative and apoptotic effects of the broad-spectrum Src family kinase inhibitor A-419259. Oncogene. Nov. 27, 2008;27(56):7055-69. doi:10.1038/onc.2008.330. Epub Sep. 15, 2008.

Poh et al., Hematopoietic cell kinase (HCK) as a therapeutic target in immune and cancer cells. Oncotarget. Jun. 30, 2015;6(18):15752-71.

Poulain et al., MYD88 L265P mutation in Waldenstrom macroglobulinemia. Blood. May 30, 2013;121(22):4504-11. doi: 10.1182/blood-2012-06-436329. Epub Mar. 26, 2013.

Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.

(56) References Cited

OTHER PUBLICATIONS

Puente et al., Whole-genome sequencing identifies recurrent mutations in chronic lymphocytic leukaemia. Nature. Jun. 5, 2011;475(7354):101-5. doi:10.1038/nature10113.
Roach et al., Analysis of genetic inheritance in a family quartet by whole-genome sequencing. Science. Apr. 30, 2010;328(5978):636-9.
Roccaro et al., A Novel Activating Mutation of CXCR4 Plays a Crucial Role in Waldenstrom Macroglobulinemia Biology. Blood. 2013;122: Abstract 272.
Roccaro et al., C1013G/CXCR4 acts as a driver mutation of tumor progression and modulator of drug resistance in lymphoplasmacytic lymphoma. Blood. Jun. 26, 2014;123(26):4120-31. doi:10.1182/blood-2014-03-564583. Epub Apr. 7, 2014.
Sahota et al., CD27 in defining memory B-cell origins in Waldenström's macroglobulinemia. Clin Lymphoma Myeloma. Mar. 2009;9(1):33-5. doi: 10.3816/CLM.2009.n.007.
Saijo et al., Essential role of Src-family protein tyrosine kinases in NF-kappaB activation during B cell development. Nat Immunol. Mar. 2003;4(3):274-9. Epub Feb. 3, 2003.
Saito et al., A pyrrolo-pyrimidine derivative targets human primary AML stem cells in vivo. Sci Transl Med. Apr. 17, 2013;5(181):181ra52. doi: 10.1126/scitranslmed.3004387.
Sanner et al., Reduced surface: an efficient way to compute molecular surfaces. Biopolymers. Mar. 1996;38(3):305-20.
Schaeffer et al., Signaling through a novel domain of gp130 mediates cell proliferation and activation of Hck and Erk kinases. Mol Cell Biol. Dec. 2001;21(23):8068-81.
Smith et al., In Waldenstrom's macroglobulinemia the quantity of detectable circulating monoclonal B lymphocytes correlates with clinical course. Blood. May 1983;61(5):911-4.
Song et al., The kinase activities of interleukin-1 receptor associated kinase (IRAK)-1 and 4 are redundant in the control of inflammatory cytokine expression in human cells. Mol Immunol. Apr. 2009;46(7):1458-66.
Suh et al., Inhibition of granulocyte-macrophage colony-stimulating factor signaling and microglial proliferation by anti-CD45RO: role of Hck tyrosine kinase and phosphatidylinositol 3-kinase/Akt. J Immunol. Mar. 1, 2005;174(5):2712-9.
Taguchi et al., Characteristic expression of Hck in human B-cell precursors. Exp Hematol. Jan. 2000;28(1):55-64. Erratum in: Exp Hematol. Mar. 2000;28(3):347.
Tai et al., Bruton tyrosine kinase inhibition is a novel therapeutic strategy targeting tumor in the bone marrow microenvironment in multiple myeloma. Blood. Aug. 30, 2012;120(9):1877-87. doi: 10.1182/blood-2011-12-396853. Epub Jun. 11, 2012.
Tai et al., Targeting Brouton's Tyrosine Kinase with PCI-32765 Blocks Growth and Survival of Multiple Myeloma and Waldenström Macroglobulinemia Via Potent Inhibition of Osteoclastogenesis, Cytokines/Chemokine Secretion, and Myeloma Stem-Like Cells in the Bone Marrow Microenvironment. Blood. Nov. 18, 2011;118(21):404.
Tiacci et al., Simple genetic diagnosis of hairy cell leukemia by sensitive detection of the BRAF-V600E mutation. Blood. Jan. 5, 2012;119(1):192-5. doi:10.1182/blood-2011-08-371179. Epub Oct. 25, 2011. Erratum in: Blood. Aug. 29, 2013;122(9):1685.
Treon et al., A new era for Waldenstrom macroglobulinemia: MYD88 L265P. Blood. May 30, 2013;121(22):4434-6. doi: 10.1182/blood-2013-04-494849.
Treon et al., A Prospective Multicenter Study of the Bruton's Tyrosine Kinase Inhibitor Ibrutinib in Patients With Relapsed or Refractory Waldenstrom's Macroglobulinemia. Blood. 2013;122:Abstract 251.
Treon et al., A prospective, multicenter, phase II study of the Bruton's Tyrosine Kinase Inhibitor Ibrutinib in patients with relapsed and refractory Waldenstrom's Macroglobulinemia. Hematol Oncol. Jun. 2013;31(S1): Abstract 067.
Treon et al., Characterization of familial Waldenstrom's macroglobulinemia. Ann Oncol. Mar. 2006;17(3):488-94. Epub Dec. 15, 2005.
Treon et al., Ibrutinib in previously treated Waldenström's macroglobulinemia. N Engl J Med. Apr. 9, 2015;372(15):1430-40. doi:10.1056/NEJMoa1501548.
Treon et al., Multicenter clinical trial of bortezomib in relapsed/refractory Waldenstrom's macroglobulinemia: results of WMCTG Trial 03-248. Clin Cancer Res. Jun. 1, 2007;13(11):3320-5.
Treon et al., MYD88 L265P somatic mutation in Waldenström's macroglobulinemia. N Engl J Med. Aug. 30, 2012;367(9):826-33. doi:10.1056/NEJMoa1200710.
Treon et al., MYD88 Mutations and Response to Ibrutinib in Waldenström's Macroglobulinemia. N Engl J Med. Aug. 6, 2015;373(6):584-6. doi:10.1056/NEJMc1506192.
Treon et al., Prospective phase II clinical trial of carfilzomib, rituximab, and dexamethasone (CaRD) in Waldenstrom's macroglobulinemia. 12th International Conference on Malignant Lymphoma. Palazzo dei Congressi, Lugano, Switzerland, Jun. 19-22, 2013, abstract 150, 2013.
Treon et al., Prospective, Multicenter Study of the MTOR Inhibitor Everolimus (RAD001) as Primary Therapy in Waldenstrom's Macroglobulinemia. Blood. 2011;118:Abstract 2951.
Treon et al., Somatic mutations in MYD88 and CXCR4 are determinants of clinical presentation and overall survival in Waldenstrom macroglobulinemia. Blood. May 1, 2014;123(18):2791-6. doi:10.1182/blood-2014-01-550905. Epub Feb. 19, 2014.
Treon et al., Whole Genome sequencing reveals a widely expressed mutation (MYD88 L265P) in Waldenstrom's Macroglobulinemia. Oral and Poster Abstracts. Dec. 2011. 1 Page.
Treon, How I treat Waldenström macroglobulinemia. Blood. Sep. 17, 2009;114(12):2375-85.
Trøen et al., CD79B and MYD88 Mutations in Splenic Marginal Zone Lymphoma. ISRN Oncol. 2013;2013:252318. doi: 10.1155/2013/252318. Epub Jan. 10, 2013.
Trott et al., AutoDock Vina: improving the speed and accuracy of docking with a new scoring function, efficient optimization, and multithreading. J Comput Chem. Jan. 30, 2010;31(2):455-61. doi: 10.1002/jcc.21334.
Varettoni et al., Prevalence and clinical significance of the MYD88 (L265P) somatic mutation in Waldenstrom's macroglobulinemia and related lymphoid neoplasms. Blood. Mar. 28, 2013;121(13):2522-8. doi: 10.1182/blood-2012-09-457101. Epub Jan. 25, 2013.
Wang et al., CD19: a biomarker for B cell development, lymphoma diagnosis and therapy. Experimental Hematol Oncol. 2012;1(36):1-7.
Wang et al., IRAK-4 inhibitors for inflammation. Curr Top Med Chem. 2009;9(8):724-37.
Watters et al., Structure, function and regulation of the Toll/IL-1 receptor adaptor proteins. Immunol Cell Biol. Aug.-Sep. 2007;85(6):411-9. Epub Jul. 31, 2007.
Willenbacher et al., Improved accuracy of discrimination between IgM multiple myeloma and Waldenström macroglobulinaemia by testing for MYD88 L265P mutations. Br J Haematol. Jun. 2013;161(6):902-4. doi:10.1111/bjh.12313. Epub Apr. 5, 2013.
Wilson et al., Targeting B cell receptor signaling with ibrutinib in diffuse large B cell lymphoma. Nat Med. Aug. 2015;21(8):922-6. doi: 10.1038/nm.3884. Epub Jul. 20, 2015.
Woyach et al., Resistance mechanisms for the Bruton's tyrosine kinase inhibitor ibrutinib. N Engl J Med. Jun. 12, 2014;370(24):2286-94. doi: 10.1056/NEJMoa1400029. Epub May 28, 2014.
Xu et al., Detection of MYD88 L265P in Peripheral Blood of Patients With Waldenström's Macroglobulinemia and IgM Monoclonal Gammopathy of Undetermined Significance. Blood. 2013;122(21): Abstract 3024.
Xu et al., Detection of MYD88 L265P in peripheral blood of patients with Waldenström's Macroglobulinemia and IgM monoclonal gammopathy of undetermined significance. Leukemia. Aug. 2014;28(8):1698-704. doi: 10.1038/leu.2014.65. Epub Feb. 10, 2014.
Xu et al., MYD88 L265P in Waldenström macroglobulinemia, immunoglobulin M monoclonal gammopathy, and other B-cell lymphoproliferative disorders using conventional and quantitative allele-specific polymerase chain reaction. Blood. Mar. 14, 2013;121(11):2051-8. doi: 10.1182/blood-2012-09-454355. Epub Jan. 15, 2013. Erratum in: Blood. Jun. 27, 2013;121(26):5259.

(56) References Cited

OTHER PUBLICATIONS

Xu et al., Detection of the MYD88 L265P mutation in Waldenström's macroglobulinemia using a highly sensitive allele-specific PCR assay. J Clinical Oncology. May 2012;30(15):8042. Abstract.
Yang et al., A mutation in MYD88 (L265P) supports the survival of lymphoplasmacytic cells by activation of Bruton tyrosine kinase in Waldenström macroglobulinemia. Blood. Aug. 15, 2013;122(7):1222-32. doi:10.1182/blood-2012-12-475111. Epub Jul. 8, 2013.
Yang et al., HCK is a survival determinant transactivated by mutated MYD88, and a direct target of ibrutinib. Blood. Jun. 23, 2016;127(25):3237-52. doi:10.1182/blood-2016-01-695098. Epub May 3, 2016.
Yang et al., Tyrosine kinase inhibition in diffuse large B-cell lymphoma: molecular basis for antitumor activity and drug resistance of dasatinib. Leukemia. Sep. 2008;22(9):1755-66. doi:10.1038/leu.2008.163. Epub Jul. 3, 2008.
Ye et al., t(1;14) and t(11;18) in the differential diagnosis of Waldenström's macroglobulinemia. Mod Pathol. Sep. 2004;17(9):1150-4.
Young et al., Survival of human lymphoma cells requires B-cell receptor engagement by self-antigens. Proc Natl Acad Sci U S A. Nov. 3, 2015;112(44):13447-54. doi:10.1073/pnas.1514944112. Epub Oct. 19, 2015.
International Search Report and Written Opinion for PCT/US2017/030116 dated Aug. 21, 2017.
[No Author Listed] Package Insert. Campath (ALEMTUZUMAB). Millennium and ILEX Partners, LP. Date created Sep. 26, 2003;1-11.
[No Author Listed] Trademark Electronic Search System (TESS) Typed Drawing. May 21, 1991. 2nd Renewal Apr. 24, 2013. Last accessed Apr. 4, 2018.
Baxter et al., Acquired mutation of the tyrosine kinase JAK2 in human myeloproliferative disorders. Lancet. Mar. 19-25, 2005;365(9464):1054-61.
Dasmahaptra et al., The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib. Br J. Haematol. Apr. 2013;161(1):43-56. Abstract only.
Montesinos-Rongen et al., Activating L265P mutations of the MYD88 gene are common in primary central nervous system lymphoma. Acta Neuropathol. Dec. 2011;122(6):791-2. doi:10.1007/s00401-011-0891-2. Epub Oct. 22, 2011.
Tesar et al., MYD88 L265P Mutations Influence Clinical Outcome and Identify a Pathway for Targeted Inhibition in Chronic Lymphocytic Leukemia. Presentation. American Society of Hematology Conference. Dec. 7, 2015. Abstract only.
Yang et al., HCK Is a Highly Relevant Target of Ibrutinib in MYD88 Mutated Waldenstrom's Macroglobulinemia and Diffuse Large B-Cell Lymphoma. Blood. 2015;126:705.
International Report on Patentability for Application No. PCT/US2017/030116 dated Nov. 8, 2018.

\* cited by examiner

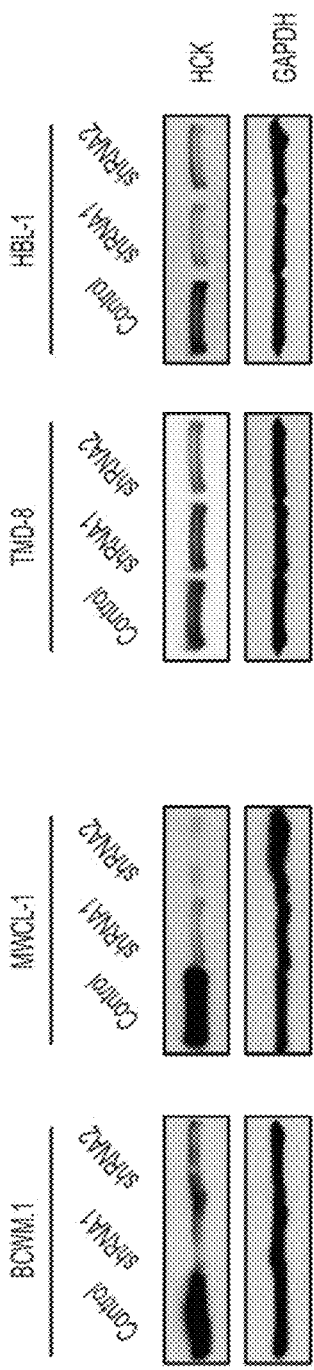
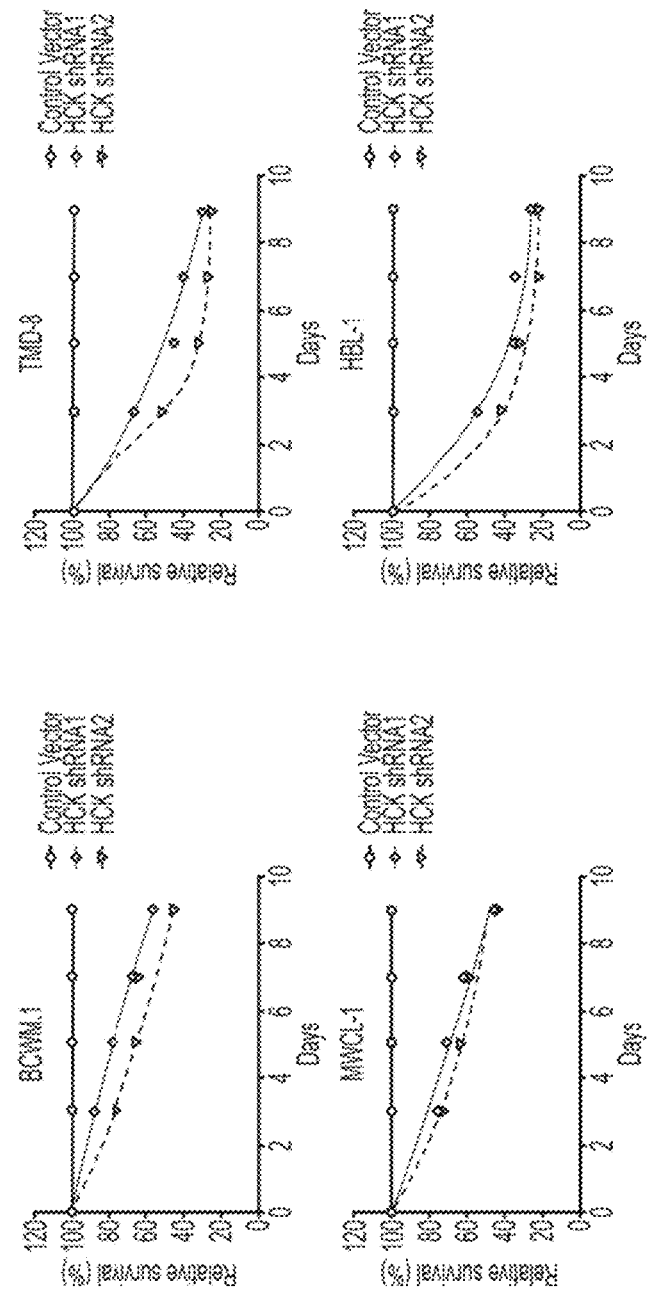
Figure 4A
Figure 4B

HCK AS A THERAPEUTIC TARGET IN MYD88 MUTATED DISEASES

RELATED APPLICATIONS

This application claims the benefit under 35 U.S.C. § 119(e) of U.S. Provisional Patent Application No. 62/329,406, filed on Apr. 29, 2016, entitled "HCK AS A THERAPEUTIC TARGET IN MYD88 MUTATED DISEASES," the entire contents of which are incorporated by reference herein.

BACKGROUND OF THE INVENTION

Next generation sequencing has revealed activating myeloid differentiation primary response 88 (MYD88) mutations in several B-cell malignancies including Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia. Particularly striking has been the expression of MYD88 mutations in Waldenstrom Macroglobulinemia (WM), wherein 95-97% of patients express MYD88$^{L265P}$, and more rarely non-L265P MYD88 mutations. WM is considered to correspond to lymphoplasmacytic lymphoma (LPL) as defined by the World Health Organization classification system. Up to 30% of patients with Activated B-Cell (ABC) Subtype of Diffuse Large B-cell lymphoma (ABC DLBCL) also express activating MYD88 mutations, including MYD88$^{L265P}$. Mutations in MYD88 promote Myddosome self-assembly and can trigger NF-kB signaling in the absence of Toll (TLR) or IL1 (IL1R) receptor signaling through IL1 Receptor Associated Kinases (IRAK4/IRAK1) or Bruton's Tyrosine Kinase (BTK).

Ibrutinib is an inhibitor of BTK that is highly active in WM, producing responses in 91% of previously treated patients. In WM patients, both major and overall responses to ibrutinib are higher in patients with MYD88 mutations. Ibrutinib also shows activity in previously treated patients with ABC DLBCL, particularly among patients with MYD88 mutations. Ibrutinib is also active in other B-cell malignancies including Chronic Lymphocytic Leukemia (CLL) and Mantle Cell Lymphoma (MCL). Suppression of tonic B-cell receptor (BCR) activity mediated by BTK has been implicated as the mechanism underlying ibrutinib activity in non-WM B-cell diseases.

SUMMARY OF THE INVENTION

It has been discovered, surprisingly, that Hematopoietic cell kinase (HCK) transcription and activation is triggered by mutated MYD88, and is an important determinant of pro-survival signaling. It has also been discovered that inhibition of the kinase activity of HCK triggers apoptosis in mutated MYD88 cells. Accordingly, in some aspects, the invention provides a method of treating a subject comprising administering to a subject with a MYD88 mutated disease (e.g., Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia) a pharmaceutical composition comprising a compound that blocks ATP binding to Hematopoietic cell kinase (HCK) at a concentration at least 10-fold lower than the concentration at which it blocks ATP binding to Bruton's Tyrosine Kinase (BTK) under equivalent conditions, wherein the compound is of a structure within Formula (I) or (II):

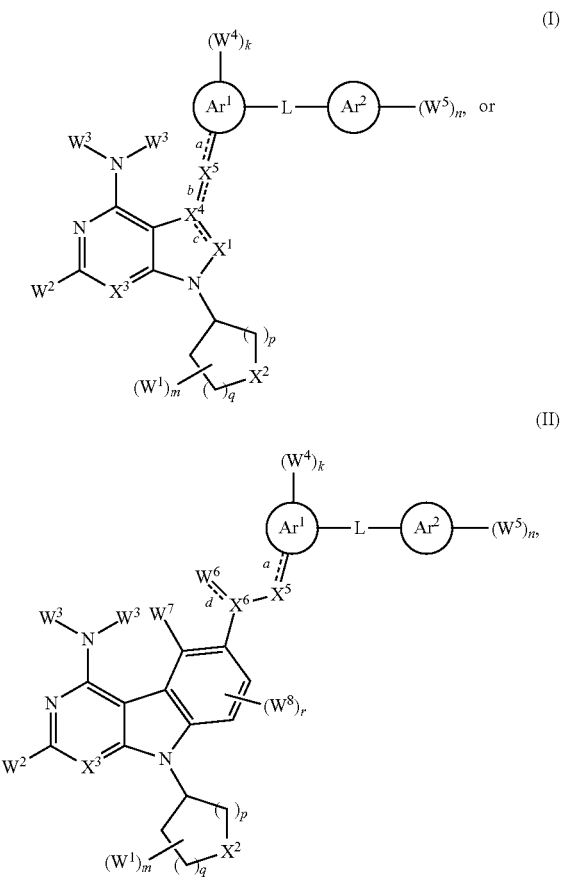

or a pharmaceutically acceptable salt, solvate, hydrate, polymorph, co-crystal, tautomer, stereoisomer, isotopically labeled derivative, or prodrug thereof, wherein:

Ar$^1$ is absent, substituted or unsubstituted carbocyclyl, substituted or unsubstituted heterocycyl, substituted or unsubstituted aryl, or substituted or unsubstituted heteroaryl;

each instance of W$^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic ring, or substituted or unsubstituted heteroaryl ring;

k is 0, 1, 2, 3, or 4, as valency permits;

L is absent, —O—, —S—, —$NR^b$—, —$C(R^c)_2$—, —$NR^bC(=O)$—, —$C(=O)NR^b$—, —OC(=O)—, —C(=O)O—, or a substituted or unsubstituted, $C_{1-6}$ hydrocarbon chain, optionally wherein one or more chain atoms of the hydrocarbon chain are independently replaced with —O—, —S—, —$NR^b$—, =N—, —N=, or —C(=O)—;

each instance of $R^b$ is independently hydrogen, substituted or unsubstituted $C_{1-6}$ alkyl, or a nitrogen protecting group;

$Ar^2$ is substituted or unsubstituted aryl or substituted or unsubstituted heteroaryl;

each instance of $W^5$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

n is 0, 1, 2, 3, 4, or 5, as valency permits;

bond a is a single or double bond, as valency permits;

$X^5$ is absent, —O—, —S—, —$NR^b$—, =N—, —N=, —$C(R^c)_2$—, —$NR^bC(=O)$—, —$C(=O)NR^b$—, —OC(=O)—, —C(=O)O—, or a substituted or unsubstituted, $C_{1-6}$ hydrocarbon chain, optionally wherein one or more chain atoms of the hydrocarbon chain are independently replaced with —O—, —S—, —$NR^b$—, =N—, —N=, or —C(=O)—;

bond b is a single or double bond, as valency permits;

$X^4$ is C, $CR^c$, or N;

bond c is a single or double bond, as valency permits;

$X^1$ is $CR^c$, N, —C(=O)—, —$S(=O)_2$—, or —$P(=O)(R^a)$—;

each instance of $R^c$ is independently hydrogen, halogen, substituted or unsubstituted $C_{1-6}$ alkyl, or —$OR^d$;

each instance of $R^d$ is independently hydrogen, substituted or unsubstituted $C_{1-6}$ alkyl, or an oxygen protecting group;

$X^2$ is —$C(R^e)_2$— or —$N(R^f)$—;

each instance of $R^e$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

$R^f$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, or a nitrogen protecting group;

each instance of $W^1$ is independently halogen, substituted or unsubstituted $C_{1-6}$ alkyl, or —$OR^d$, or two instances of $W^1$ at the same carbon atom are joined to form =O;

m is 0, 1, 2, 3, 4, 5, 6, 7, 8, 9, 10, or 11, as valency permits;

p is 1 or 2;

q is 1 or 2;

$X^3$ is $CR^h$ or N;

$R^h$ is hydrogen, halogen, substituted or unsubstituted $C_{1-6}$ alkyl, or —$OR^d$;

$W^2$ is hydrogen, halogen, substituted or unsubstituted $C_{1-6}$ alkyl, or —$OR^d$;

each instance of $W^3$ is independently hydrogen, substituted or unsubstituted $C_{1-6}$ alkyl, or a nitrogen protecting group;

$X^6$ is absent, C, $CR^c$, or N;

bond d is absent, a single bond, or a double bond, as valency permits;

$W^6$ is absent, or $W^6$ and $W^7$ are joined to form substituted or unsubstituted carbocyclyl, substituted or unsubstituted heterocyclyl, substituted or unsubstituted aryl, or substituted or unsubstituted heteroaryl;

$W^7$ is hydrogen, halogen, substituted or unsubstituted $C_{1-6}$ alkyl, or —$OR^d$;

each instance of $W^8$ is independently halogen, substituted or unsubstituted $C_{1-6}$ alkyl, or —$OR^d$; and r is 0, 1, or 2.

In some embodiments, the compound blocks ATP binding to HCK at a concentration at least 30-fold, e.g., at least 100-fold, lower than the concentration at which it blocks ATP binding to BTK under equivalent conditions.

In some embodiments, the blocking of ATP binding to HCK and BTK is tested in a native protein kinase activity profiling assay performed under conditions described in Example 1. In some embodiments, the compound blocks ATP binding to HCK at a concentration of 1 µm, e.g., at a concentration of 0.1 µm, as determined by absence of a detectable band in the native protein kinase activity profiling assay performed under conditions described in Example 1. In some embodiments, the compound does not block ATP binding to BTK at a concentration of 1 µm, e.g., at a concentration of 0.1 µm as determined by presence of a detectable band in the native protein kinase activity profiling assay performed under conditions described in Example 1.

In some embodiments, the compound further blocks ATP binding to LYN proto-oncogene (LYN), e.g., at a concentration at least 10-fold lower than the concentration at which it blocks ATP binding to BTK under equivalent conditions. In some embodiments, the blocking of ATP binding to LYN and BTK is tested in a native protein kinase activity profiling assay performed under conditions described in Example 1. In some embodiments, the compound blocks ATP binding to LYN at a concentration of 1 µm, e.g., at a concentration of 0.1 µm, as determined by absence of a detectable band in the native protein kinase activity profiling assay performed under conditions described in Example 1. In some embodiments, the compound does not block ATP binding to BTK at a concentration of 1 µm, e.g., at a concentration of 0.1 µm as determined by presence of a detectable band in the native protein kinase activity profiling assay performed under conditions described in Example 1.

In some embodiments, the compound blocks ATP binding to LYN at a concentration at least 30-fold, e.g., at least 100-fold, lower than the concentration at which it blocks ATP binding to BTK under equivalent conditions.

In some embodiments, the compound further blocks ATP binding to ATP binding to Proto-oncogene tyrosine-protein kinase SRC (SRC), e.g., at a concentration at least 10-fold lower than the concentration at which it blocks ATP binding to BTK under equivalent conditions. In some embodiments, the blocking of ATP binding to SRC and BTK is tested in a native protein kinase activity profiling assay performed under conditions described in Example 1. In some embodiments, the compound blocks ATP binding to SRC at a concentration of 1 µm, e.g., at a concentration of 0.1 µm, as determined by absence of a detectable band in the native protein kinase activity profiling assay performed under conditions described in Example 1. In some embodiments, the compound does not block ATP binding to BTK at a concentration of 1 µm, e.g., at a concentration of 0.1 µm as determined by presence of a detectable band in the native protein kinase activity profiling assay performed under conditions described in Example 1. In some embodiments, the compound blocks ATP binding to SRC at a concentration at least 30-fold, e.g., at least 100-fold, lower than the concentration at which it blocks ATP binding to BTK under equivalent conditions.

In some embodiments, the MYD88 mutated disease is selected from Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, and immune privileged lymphoma (e.g., testicular lymphoma, marginal zone lymphoma, and chronic lymphocytic leukemia). In some embodiments, the MYD88 mutated disease is Waldenstrom's Macroglobulinemia. In some embodiments, the MYD88 mutated disease is ABC subtype of diffuse large B-cell lymphoma. In some embodiments, the subject has a mutation in the gene encoding myeloid differentiation primary response 88 (MYD88). In some embodiments, the mutation in the gene encoding MYD88 results in a single nucleotide change from T to C in the MYD88 gene. In some embodiments, the mutation in the gene encoding MYD88 results in an amino acid change from leucine to proline at position 265 in the MYD88 protein. In some embodiments, the mutation in the gene encoding MYD88 results in an amino acid change selected from V217F, W218R, I220T, S222R, M232T, S243N, and T294P. In some embodiments, the mutation in the gene encoding MYD88 results in an amino acid change of S222R. In some embodiments, the subject has been previously tested and is known to have a mutation in the gene encoding MYD88.

In some embodiments, the compound is of the formula:

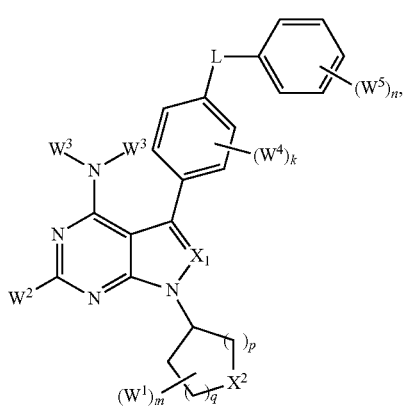

or a pharmaceutically acceptable salt, solvate, hydrate, polymorph, co-crystal, tautomer, stereoisomer, isotopically labeled derivative, or prodrug thereof.

In some embodiments, the compound is of the formula:

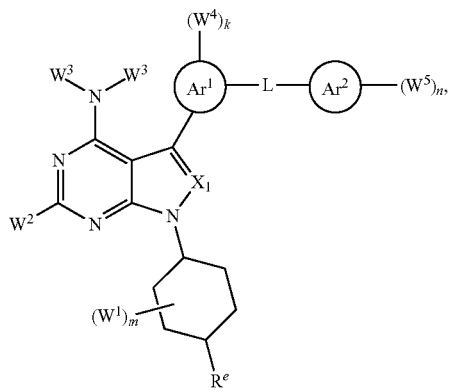

or a pharmaceutically acceptable salt, solvate, hydrate, polymorph, co-crystal, tautomer, stereoisomer, isotopically labeled derivative, or prodrug thereof.

In some embodiments, the compound is of the formula:

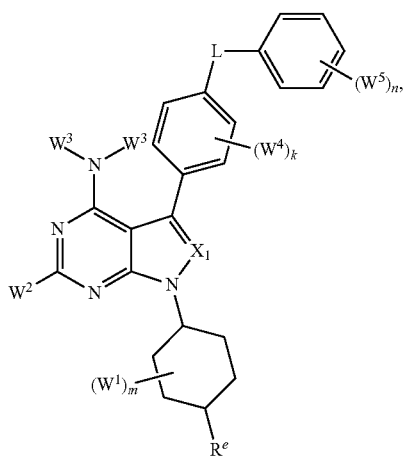

or a pharmaceutically acceptable salt, solvate, hydrate, polymorph, co-crystal, tautomer, stereoisomer, isotopically labeled derivative, or prodrug thereof.

In some embodiments, the compound is of the formula:

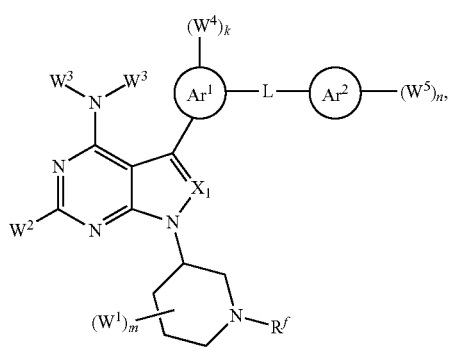

or a pharmaceutically acceptable salt, solvate, hydrate, polymorph, co-crystal, tautomer, stereoisomer, isotopically labeled derivative, or prodrug thereof.

In some embodiments, the compound is of the formula:

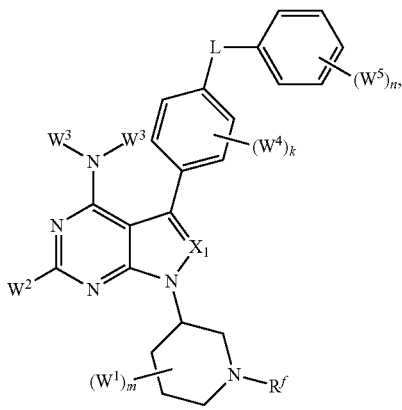

or a pharmaceutically acceptable salt, solvate, hydrate, polymorph, co-crystal, tautomer, stereoisomer, isotopically labeled derivative, or prodrug thereof.

In some embodiments, each one of $Ar^1$ and $Ar^2$ is substituted or unsubstituted phenyl. In some embodiments, L is —O—. In some embodiments, $X^1$ is $CR^c$. In some embodiments, $X^1$ is N.

In some embodiments, the compound is of the formula:

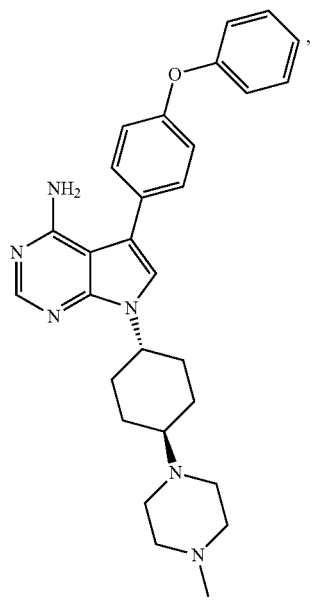

or a pharmaceutically acceptable salt, solvate, hydrate, polymorph, co-crystal, tautomer, stereoisomer, isotopically labeled derivative, or prodrug thereof.

In some embodiments, the method further comprises administering an anti-cancer agent to the subject. In some embodiments, the anti-cancer agent is a chemotherapeutic agent.

In some embodiments, the method further comprises administering an agent that blocks ATP binding to LYN, e.g., at a concentration at least 10-fold lower than the concentration at which it blocks ATP binding to BTK under equivalent conditions.

In some embodiments, the method further comprises administering an agent that blocks ATP binding to SRC, e.g., at a concentration at least 10-fold lower than the concentration at which it blocks ATP binding to BTK under equivalent conditions.

In some embodiments, the method further comprises administering to the subject one or more of a proteasome inhibitor (e.g., bortezomib, carfilzomib, ixazomib or oprozomib), a monoclonal antibody (e.g., rituximab, daratumumab, ofatumumab or obinituzumab), an alkylator drug (e.g., bendamustine, cyclophosphamide), a nucleoside analogue (e.g., fludarabine or cladribine), an MTOR inhibitor (e.g., everolimus), a BTK inhibitor (e.g., ibrutinib, acalabrutinib or BGB-3111), a BCR inhibitor (e.g., a SYK inhibitor) and/or an immunomodulating agent (e.g., thalidomide or lenalidomide).

In some aspects, the invention provides a method of treating a subject comprising performing an assay on a biological sample obtained from a subject in need thereof to determine whether the subject has a mutation in the gene encoding MYD88; if the subject has a mutation in the gene encoding MYD88, then administering to the subject a pharmaceutical composition comprising a compound that blocks ATP binding to Hematopoietic cell kinase (HCK) at a concentration at least 10-fold lower than the concentration at which it blocks ATP binding to Bruton's Tyrosine Kinase (BTK) under equivalent conditions, wherein the compound is of a structure within Formula (I) or (II), or a pharmaceutically acceptable salt, solvate, hydrate, polymorph, co-crystal, tautomer, stereoisomer, isotopically labeled derivative, or prodrug thereof.

In some embodiments, the biological sample is a sample of bone marrow, lymph node, spleen or blood.

In some embodiments, the mutation in the gene encoding MYD88 is a mutation at position 38182641 in chromosome 3p22.2. In some embodiments, the mutation at position 38182641 results in a single nucleotide change from T to C in the myeloid differentiation primary response 88 (MYD88) gene. In some embodiments, the mutation at position 38182641 results in an amino acid change from leucine to proline at position 265 in the myeloid differentiation primary response 88 protein. In some embodiments, the mutation in the gene encoding MYD88 results in an amino acid change selected from V217F, W218R, I220T, S222R, M232T, S243N, and T294P. In some embodiments, the mutation in the gene encoding MYD88 results in an amino acid change of S222R.

In some embodiments, the assay to determine whether the subject has a mutation in the gene encoding MYD88 comprises an allele specific polymerase chain reaction assay. In some embodiments, the assay to determine whether the subject has a mutation at position 38182641 in chromosome 3p22.2 comprises allele specific polymerase chain reaction performed using an allele specific primer, wherein the allele specific primer hybridizes at or near its 3' end to the mutation at position 38182641 in chromosome 3p22.2.

In some embodiments, Sanger, whole exome or whole genome sequencing has been used to identify somatic mutations in MYD88.

In some embodiments, the compound blocks ATP binding to HCK at a concentration at least 30-fold, e.g., at least 100-fold, lower than the concentration at which it blocks ATP binding to BTK under equivalent conditions.

In some embodiments, the blocking of ATP binding to HCK and BTK is tested in a native protein kinase activity profiling assay performed under conditions described in Example 1. In some embodiments, the compound blocks ATP binding to HCK at a concentration of 1 μm, e.g., at a concentration of 0.1 μm, as determined by absence of a detectable band in the native protein kinase activity profiling assay performed under conditions described in Example 1. In some embodiments, the compound does not block ATP binding to BTK at a concentration of 1 μm, e.g., at a concentration of 0.1 μm, as determined by presence of a detectable band in the native protein kinase activity profiling assay performed under conditions described in Example 1.

In some embodiments, the compound further blocks ATP binding to LYN, e.g., at a concentration at least 10-fold lower than the concentration at which it blocks ATP binding to BTK under equivalent conditions. In some embodiments, the blocking of ATP binding to LYN and BTK is tested in a native protein kinase activity profiling assay performed under conditions described in Example 1. In some embodiments, the compound blocks ATP binding to LYN at a concentration of 1 μm, e.g., at a concentration of 0.1 μm, as determined by absence of a detectable band in the native protein kinase activity profiling assay performed under conditions described in Example 1. In some embodiments, the compound does not block ATP binding to BTK at a concentration of 1 μm, e.g., at a concentration of 0.1 μm as determined by presence of a detectable band in the native protein kinase activity profiling assay performed under conditions described in Example 1.

In some embodiments, the compound blocks ATP binding to LYN at a concentration at least 30-fold, e.g., at least 100-fold, lower than the concentration at which it blocks ATP binding to BTK under equivalent conditions.

In some embodiments, the compound further blocks ATP binding to ATP binding to SRC, e.g., at a concentration at least 10-fold lower than the concentration at which it blocks ATP binding to BTK under equivalent conditions. In some embodiments, the blocking of ATP binding to SRC and BTK is tested in a native protein kinase activity profiling assay performed under conditions described in Example 1. In some embodiments, the compound blocks ATP binding to SRC at a concentration of 1 μm, e.g., at a concentration of 0.1 μm, as determined by absence of a detectable band in the native protein kinase activity profiling assay performed under conditions described in Example 1. In some embodiments, the compound does not block ATP binding to BTK at a concentration of 1 μm, e.g., at a concentration of 0.1 μm as determined by presence of a detectable band in the native protein kinase activity profiling assay performed under conditions described in Example 1.

In some embodiments, the compound blocks ATP binding to SRC at a concentration at least 30-fold, e.g., at least 100-fold, lower than the concentration at which it blocks ATP binding to BTK under equivalent conditions.

In some embodiments, the compound is of the formula:

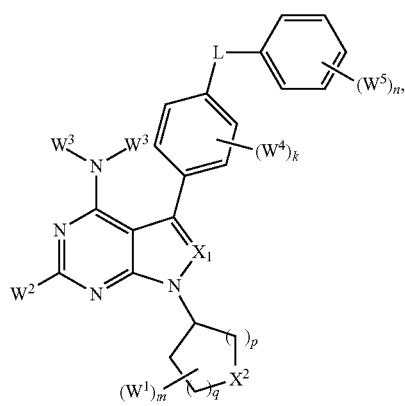

or a pharmaceutically acceptable salt, solvate, hydrate, polymorph, co-crystal, tautomer, stereoisomer, isotopically labeled derivative, or prodrug thereof.

In some embodiments, the compound is of the formula:

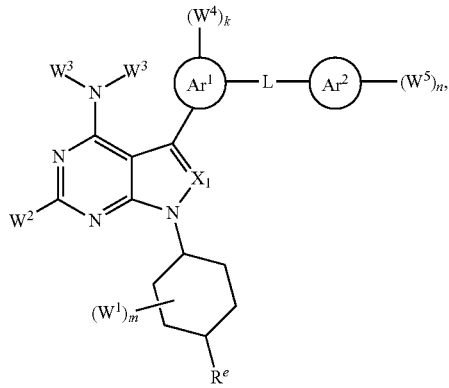

or a pharmaceutically acceptable salt, solvate, hydrate, polymorph, co-crystal, tautomer, stereoisomer, isotopically labeled derivative, or prodrug thereof.

In some embodiments, the compound is of the formula:

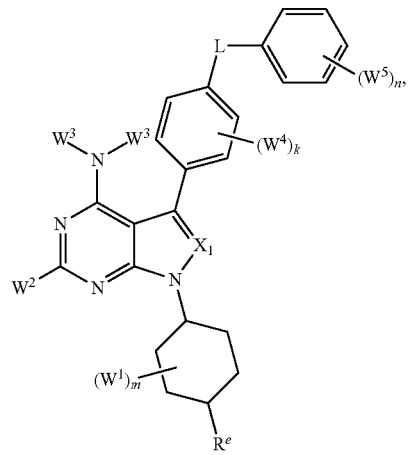

or a pharmaceutically acceptable salt, solvate, hydrate, polymorph, co-crystal, tautomer, stereoisomer, isotopically labeled derivative, or prodrug thereof.

In some embodiments, the compound is of the formula:

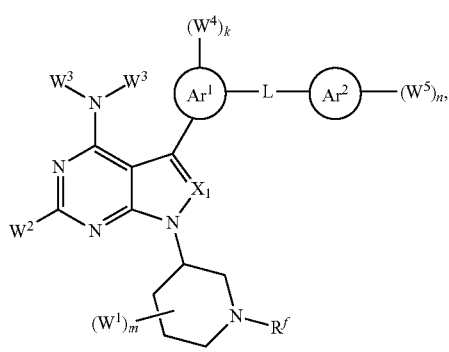

or a pharmaceutically acceptable salt, solvate, hydrate, polymorph, co-crystal, tautomer, stereoisomer, isotopically labeled derivative, or prodrug thereof.

In some embodiments, the compound is of the formula:

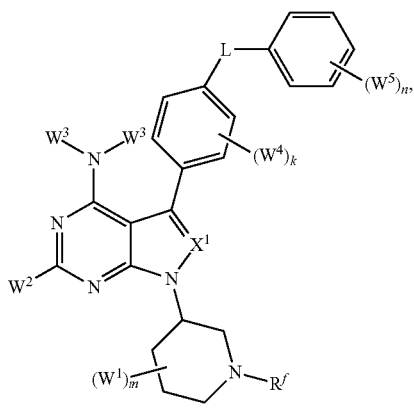

or a pharmaceutically acceptable salt, solvate, hydrate, polymorph, co-crystal, tautomer, stereoisomer, isotopically labeled derivative, or prodrug thereof.

In some embodiments, each one of $Ar^1$ and $Ar^2$ is substituted or unsubstituted phenyl. In some embodiments, L is —O—. In some embodiments, $X^1$ is $CR^e$. In some embodiments, $X^1$ is N.

In some embodiments, the compound is of the formula:

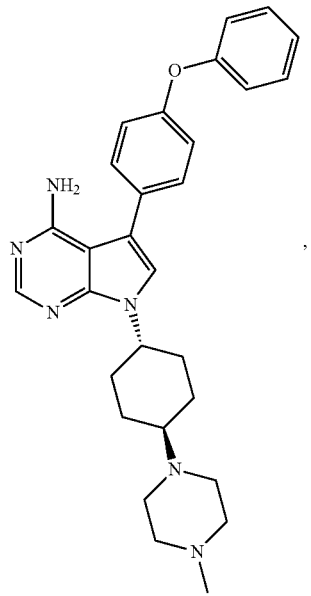 [SMILES: CN1CCN([C@H]2CC[C@H](n3cc(-c4ccc(Oc5ccccc5)cc4)c4c(N)ncnc43)CC2)CC1]

or a pharmaceutically acceptable salt, solvate, hydrate, polymorph, co-crystal, tautomer, stereoisomer, isotopically labeled derivative, or prodrug thereof.

In some embodiments, the method further comprises administering an anti-cancer agent to the subject. In some embodiments, the anti-cancer agent is a chemotherapeutic agent.

In some embodiments, the method further comprises administering an agent that blocks ATP binding to LYN, e.g., at a concentration at least 10-fold lower than the concentration at which it blocks ATP binding to BTK under equivalent conditions.

In some embodiments, the method further comprises administering an agent that blocks ATP binding to SRC, e.g., at a concentration at least 10-fold lower than the concentration at which it blocks ATP binding to BTK under equivalent conditions.

In some embodiments, the method further comprises administering to the subject one or more of a proteasome inhibitor (e.g., bortezomib, carfilzomib, ixazomib or oprozomib), a monoclonal antibody (e.g., rituximab, daratumumab, ofatumumab or obinituzumab), an alkylator drug (e.g., bendamustine, cyclophosphamide), a nucleoside analogue (e.g., fludarabine or cladribine), an MTOR inhibitor (e.g., everolimus), a BTK inhibitor (e.g., ibrutinib, acalabrutinib or BGB-3111), a BCR inhibitor (e.g., a SYK inhibitor) and/or an immunomodulating agent (e.g., thalidomide or lenalidomide).

In some instances, patients who are treated with a BTK inhibitor, such as ibrutinib, are resistant to such BTK inhibitor treatment. A subject who is resistant to treatment with a BTK inhibitor is one who shows no or minimal response to the treatment. In some embodiments, response to a treatment is measured by reduction in tumor cells or tumor cell killing. In some embodiments, response to a treatment is measured by changes in symptoms of the disease, condition or malignancy (e.g., WM or CLL). It has been discovered that the compounds that block ATP binding to HCK as described herein are able to cause tumor cell killing even in cells that are derived from patients who are resistant to a BTK inhibitor treatment.

Accordingly, provided herein is a method of treating a subject comprising administering to the subject any one of the pharmaceutical compositions described herein, wherein the subject is resistant to treatment with a BTK inhibitor. In some embodiments, a subject who is resistant to treatment with a BTK inhibitor is diagnosed to have a MYD88 mutated disease (e.g., WM, non-IgM secreting lymphoplasmacytic lymphoma, ABC DLBCL, primary CNS lymphoma, or an immune privileged lymphoma such as testicular lymphoma, marginal zone lymphoma and chronic lymphocytic leukemia). In some embodiments, a subject who is resistant to treatment with a BTK inhibitor is diagnosed to have a MYD88 mutated disease but may or may not have a mutation in MYD88. In some embodiments, the BTK inhibitor to which a subject is resistant is ibrutinib, CC-292, ONO-4059 or ACP-196 (also known as acalabrutinib). In some embodiments, a subject who is resistant to treatment with a BTK inhibitor has a BTK mutations, e.g., mutation $BTK^{C481S}$.

BRIEF DESCRIPTION OF THE DRAWINGS

FIG. 1A shows HCK transcript levels in MYD88 mutated WM (BCWM.1, MWCL-1) and ABC DLBCL (TMD-8, HBL-1, OCI-Ly3, SU-DHL2) cells, and MYD88 wild-type (OCI-Ly7 and OCI-Ly19 GCB DLBCL, Ramos Burkitt, MM1.S and RPMI-8226 myeloma) cells by quantitative RT-PCR. FIG. 1B shows HCK transcription, measured using TaqMan® Gene Expression Assay, in primary lymphoplasmacytic cells (CD19$^+$) from MYD88 L265P expressing WM patients, and healthy donor derived non-memory (CD19$^+$CD27$^+$) and memory (CD19$^+$CD27$^+$) B-cells. p<0.01 for comparison of WM LPC versus either healthy donor non-memory or memory B-cells. FIG. 1C shows fold change in HCK transcription following lentiviral transduction with vector control, Flag-tagged MYD88 L265P or MYD88 wild-type protein in cell lines expressing mutated or wild-type MYD88. At the bottom of the FIG. 1C, total Flag-tagged MYD88 L265P or wild-type protein levels are shown for all transduced cell lines to demonstrate relative translation efficiency for MYD88 L265P and wild-type vectors, as well as GAPDH protein levels as protein loading controls.

FIGS. 2A and 2B show expression of IL6 and IL6R transcripts using TaqMan® Gene Expression Assays in MYD88 mutated and MYD88 wild-type (WT) cell lines, respectively. FIGS. 2C and 2D show IL6 and IL6R transcript levels, respectively, determined by TaqMan® Gene Expression Assays in primary lymphoplasmacytic cells (CD19$^+$) from MYD88 L265P expressing WM patients, and healthy donor derived non-memory (CD19$^+$CD27$^+$) and memory (CD19$^+$CD27$^+$) B-cells. $p<0.01$ for comparison of IL6 or IL6R transcript levels in WM LPC versus either healthy donor non-memory or memory B-cells. FIGS. 2E and 2F respectively show IL6 and IL6R transcription following over-expression of MYD88 L265P or wild-type protein in cell lines expressing mutated or wild-type MYD88. Total Flag-tagged MYD88 L265P or wild-type protein, as well as GAPDH protein levels determined by immunoblotting are shown for all transduced cell lines in FIG. 1C.

FIG. 3A shows results of PhosFlow analysis for phosphorylated HCK (pHCK$^{Tyr411}$) in MYD88 mutated WM (BCWM.1, MWCL-1) and ABC DLBCL (TMD-8, OCI-Ly3) cells; MYD88 wild-type GCB DLBCL (OCI-Ly7, OCI-Ly19), Ramos Burkitt, and RPMI-8226 myeloma cells. FIG. 3B shows results of PhosFlow analysis for pHCK$^{Tyr411}$ in primary lymphoplasmacytic cells (CD20$^+$) from 3 representative MYD88 L265P expressing WM patients, as well as non-memory (CD20$^+$CD27$^-$) and memory (CD20$^+$CD27$^+$) B-cells from healthy donors. Percentage of cells gating for pHCK$^{Tyr411}$ expression are shown in FIG. 3A and FIG. 3B. Histogram depicts the results of pHCK$^{Tyr411}$ expression in LPC derived from 20 WM patients, as well as non-memory and memory B-cells from 5 healthy donors. $p<0.01$ for comparison of p-HCK expression in WM LPC versus either healthy donor non-memory or memory B-cells. FIG. 3C shows pHCK$^{Tyr411}$ expression in the presence or absence of IL6 (1 ng/mL) for 5 minutes in MYD88 mutated (BCWM.1, MWCL-1, TMD-8, HBL-1, OCI-Ly3) and MYD88 wild-type (OCI-Ly7, OCI-Ly19, Ramos, RPMI 8226) cell lines, as well as primary WM lymphoplasmacytic cells. Peak pHCK$^{Tyr411}$ activation was determined by PhosFlow analysis after three MYD88 mutated cell lines were cultured with IL6 (1 ng/mL) for 2, 5, and 15 minutes. (*) $p<0.05$; () $p<0.01$; (*) $p<0.001$ versus untreated controls. FIG. 3D shows PhosFlow analysis of pHCK$^{Tyr411}$ in BCWM.1 cells transduced with scrambled control vector or IL6ST knockdown vector (shRNA2) in the presence or absence of 1 ng/mL of IL6.

FIGS. 4A and 4B show that HCK is a determinant of survival in MYD88 mutated cells. FIG. 4A shows HCK protein levels determined by western blot analysis. FIG. 4B shows survival determined by AlamarBlue® cell viability assay over an 11 day evaluation period in MYD88 mutated BCWM.1 and MWCL-1 WM cells, and TMD-8 and HBL-1 ABC DLBCL cells following transduction with inducible HCK knockdown (shRNA1, shRNA2) or scrambled control vectors. Mean of two independent experiments is depicted for time points.

FIG. 5A shows PhosFlow analysis for pHCK$^{Tyr411}$, pBTK, pAKT, and pERK in scramble control vector or HCK transduced MYD88 mutated BCWM.1 and MWCL-1 cells. FIG. 5B shows the impact of HCK over-expression on PI3K/AKT (PIK3R2, AKT), MAPK (PLCγ1, ERK1/2), BTK (BTK, PLCγ2), and IRAK4 signaling in BCWM.1 and MWCL-1 cells using antibodies to detect phospho-specific and total protein expression by immunoblotting. FIG. 5C shows the impact of HCK knockdown on PI3K/AKT (PIK3R2, AKT), MAPK (PLCγ1, ERK1/2), BTK (BTK, PLCγ2), and IRAK4 signaling in BCWM.1 and MWCL-1 cells using antibodies to detect phospho-specific and total protein expression by immunoblotting. GAPDH protein levels were determined for control purposes in all experiments.

FIG. 6A shows a docking model of the ibrutinib aligned with the co-crystal structure of HCK-A419259. The hydrogen bonds between the aminopyrimidine moiety of ibrutinib and the hinge region of HCK are indicated. Docking studies showed that ibrutinib bound to the ATP-binding pocket of HCK with calculated affinity energy (AG) of −10.5 kcal/mol. FIG. 6B shows results from pull-down experiments using streptavidin beads (SVB) and biotinylated ibrutinib (IB-BTN) and CC-292 (CC-BTN) to detect BTK and HCK binding in MYD88 mutated BCWM.1, MWCL-1 and TMD-8 cells. FIG. 6C shows results from kinase active-site inhibition assays utilizing an ATP-biotin (ATP-BTN) probe that was used to pull-down active kinases in presence of ibrutinib, CC-292, or A419259 in lysates from BCWM.1 WM cells.

FIG. 7A shows PhosFlow analysis showing changes in pHCK$^{Tyr411}$ following treatment of MYD88 mutated WM (BCWM.1, MWCL-1) and ABC DLBCL (TMD-8, OCI-Ly3, HBL-1) cells and MYD88 mutated primary lymphoplasmacytic cells from 4 WM patients with 0.5 μM of A419259, ibrutinib or CC-292 for 30 minutes.

FIG. 7B shows dose dependent survival determined by CellTiter-Glo® Luminescent cell viability assay for mutated (BCWM.1, MWCL-1, TMD-8, HBL-1, OCI-LY3) and wild type (OCI-LY7, OCI-LY19, Ramos, RPMI 8226) MYD88 cells following treatment with ibrutinib, A419259 or CC-292 for 72 hours. FIG. 7C shows apoptotic changes using propidium iodide (PI) and Annexin V (FITC-A) staining following treatment of mutated and wild type MYD88 cell lines, and primary lymphoplasmacytic cells from 3 WM patients with 0.5 μM of A419259, ibrutinib or CC-292 for 18 hours. DMSO denotes vehicle control only treated cells. Cell line results are from experiments performed in triplicate. Primary LPC data are from results obtained from 6 WM patients. (*) $p\leq0.05$ and (**) $p\leq0.01$ versus DMSO controls. FIG. 7D shows dose dependent tumor cell survival of MYD88 mutated BCWM.1 cells transduced with control vector or vectors expressing wild-type BTK (BTK WT); BTK expressing mutated site for ibrutinib binding (BTK$^{C481S}$); wild-type HCK (HCK WT); or HCK expressing the gatekeeper mutation (HCK$^{T333M}$; HCK$^{T338M}$ based on c-SRC numbering)[16] and treated with ibrutinib, A419259 or CC-292. Protein levels following transduction with control, wild-type or mutated BTK or HCK vectors are also shown at the bottom of FIG. 7D.

FIG. 8A shows cell viabilities in BCWM.1 WM cells transfected with vectors to express either wild-type BTK (BTK-wt), BTK$^{C481S}$ or a control vector, and treated with an HCK inhibitor A419259 or a BTK inhibitor, ibrutinib, CC-292, ONO-4059 or ACP-196. FIG. 8B shows cell viabilities in TMD-8 ABC DLBCL cells transfected with vectors to express either wild-type BTK (BTK-wt), BTK$^{C481S}$ or a control vector, and treated with an HCK inhibitor A419259 or a BTK inhibitor, ibrutinib, CC-292, ONO-4059 or ACP-196.

DETAILED DESCRIPTION OF THE INVENTION

Figure 1A:
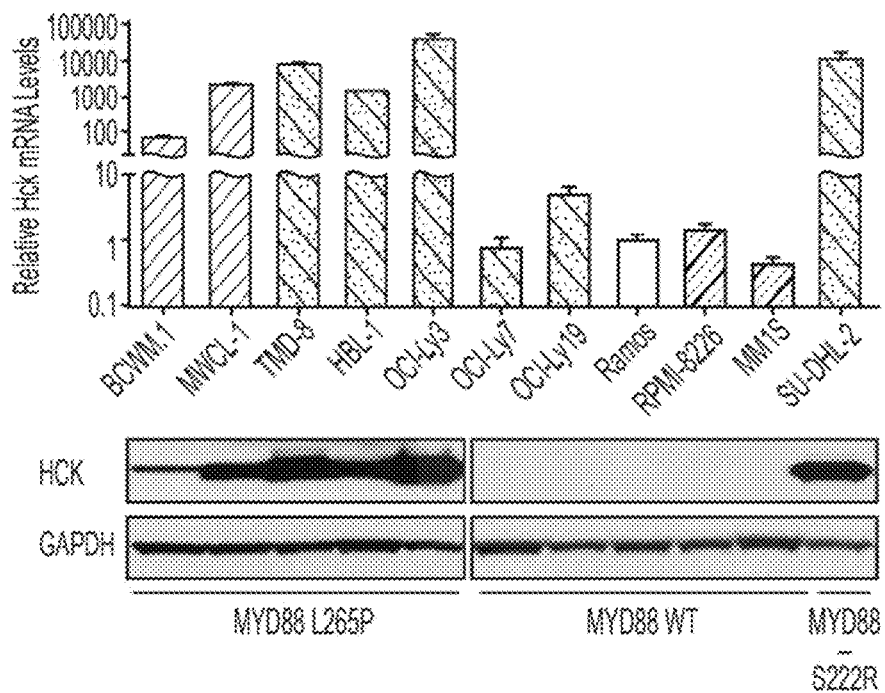
FIGS. 1A-1C show that HCK transcription is driven by mutated MYD88.

The present invention, in one aspect, relates to the surprising discovery that HCK transcription and activation is triggered by mutated MYD88, and is an important determinant of pro-survival signaling. The invention is based, at least in part, on the discovery that inhibition of the kinase activity of HCK triggers apoptosis in mutated MYD88 cells.

According to one aspect, the present invention provides a method of treating a subject comprising administering to a subject with MYD88 mutated disease (e.g., Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia) a pharmaceutical composition comprising a compound that blocks ATP binding to Hematopoietic cell kinase (HCK) at a concentration at least 10-fold lower than the concentration at which it blocks ATP binding to Bruton's Tyrosine Kinase (BTK) under equivalent conditions, wherein the compound has a structure within Formula (I) or (II) as described herein.

HCK is a member of the src-family of protein tyrosine kinases, and is aberrantly up-regulated in WM cells. In myeloma cells, HCK is activated by interleukin 6 (IL6) through the IL6 co-receptor IL6ST (GP130).

Bruton's tyrosine kinase (BTK) is a member of the src-related BTK/Tec family of cytoplasmic tyrosine kinases, is required for B cell receptor signaling, plays a key role in B-cell maturation, and exhibits increased activation in a number of B-cell malignancies.

LYN proto-oncogene (LYN) is a member of the src-family of protein tyrosine kinases, plays an important role in the regulation of B-cell differentiation, proliferation, survival and apoptosis, is important for immune self-tolerance, and acts downstream of several immune receptors, including the B-cell receptor (BCR). Without wishing to be bound by theory, BCR signaling is thought to be involved in pro-growth and survival signaling in MYD88 mutated disease, as well as being involved in non-MYD88 mutated disease. For example, BCR signaling is thought to be active in Waldenstrom's Macroglobulinemia, ABC subtype of diffuse large B-cell lymphoma, and chronic lymphocytic leukemia.

Proto-oncogene tyrosine-protein kinase SRC (SRC) is a protein tyrosine kinase, plays a central role in the regulation of a variety of biological processes, such as cell proliferation, migration, adhesion, and survival in solid tumors, and is overexpressed in Waldenstrom's Macroglobulinemia.

In some embodiments, provided methods include inhibiting LYN and/or SRC. In some embodiments, a compound of the disclosure blocks ATP binding to HCK at a concentration at least 10-fold lower than the concentration at which it blocks ATP binding to Bruton's Tyrosine Kinase (BTK) under equivalent conditions, and further blocks ATP binding to LYN at a concentration at least 10-fold lower than the concentration at which it blocks ATP binding to BTK under equivalent conditions. In some embodiments, a compound of the disclosure blocks ATP binding to HCK at a concentration at least 10-fold lower than the concentration at which it blocks ATP binding to Bruton's Tyrosine Kinase (BTK) under equivalent conditions, and further blocks ATP binding to SRC at a concentration at least 10-fold lower than the concentration at which it blocks ATP binding to BTK under equivalent conditions.

In some embodiments, the method further comprises administering an agent which inhibits LYN and/or SRC. For example, in some embodiments, a compound of a structure within Formula (I) or (II) as described herein is administered to the subject in combination (e.g., concurrently or sequentially) with an agent which blocks ATP binding to LYN and/or an agent which blocks ATP binding to SRC.

The terms "block" or "blocking" refer to the ability of a compound to prevent a biological interaction (e.g., binding) in a cell relative to a negative control, e.g., vehicle. For example, a compound can block ATP from binding to the ATP binding pocket of a kinase. Such blocking may occur by direct binding of the compound to the ATP binding pocket itself, or indirect blocking. In some embodiments, the term refers to a reduction in the level of binding of ATP to a kinase, e.g., HCK, and/or LYN, and/or SRC, to a level that is statistically significantly lower than an initial level, which may, for example, be a baseline level of ATP binding. In some embodiments, the term refers to a reduction in the level of ATP binding to a kinase, e.g., HCK, and/or LYN, and/or SRC, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of ATP binding. In some embodiments, blocking ATP binding leads to a reduction in the level of enzyme activity, e.g., HCK, and/or LYN, and/or SRC activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound or pharmaceutical composition is referred to as "selectively," "specifically," or "competitively" binding a first protein, the compound binds the first protein, e.g., HCK or LYN or SRC, with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein that is different from the first protein, e.g., BTK. In some embodiments, a compound blocks ATP binding to a first protein, e.g., HCK or LYN or SRC, at a lower concentration (e.g., not less than about 2-fold, not less than about 5-fold, not less than about 10-fold, not less than about 30-fold, not less than about 100-fold, not less than about 1,000-fold, or not less than about 10,000-fold) than it blocks ATP binding a second protein that is different from the first protein, e.g., BTK.

Compounds which selectively block ATP binding to a kinase (e.g., HCK) provided herein can be identified and/or characterized by methods known in the art. Methods include purified enzyme and cell based biochemical and binding assays such as an HCK gatekeeper mutant rescue assay, an in vitro kinase assay, e.g., using HCK gatekeeper mutated kinase, competitive binding assays using KiNativ technology or biotin tagged inhibitors, e.g., HCK inhibitors. Suitable assays for determining selective inhibition of HCK by a compound include, but are not limited to, Life Technology Z-Lyte activity assays (e.g., including HCK gatekeeper mutants and GK+6 mutants); DiscoverX KinomeScan binding assays; MRC radioactivity assays; ACD Ba/F3 viability assays (e.g., including HCK gatekeeper mutants and GK+6 mutants); Yeast hybrid proliferation assays; Protein thermostability assays; and cancer cells with HCK gatekeeper mutants or GK+6 mutants proliferation-rescue assays. Such assays can also be used to determine selective inhibition of LYN and/or SRC by a compound.

In some embodiments, selective inhibition of HCK and/or LYN and/or SRC by a compound can be determined by a native protein kinase activity profiling assay such as a KiNativ profiling. As described in the Example, in some embodiments, the ability of inhibitors to protect kinases from subsequent labeling with a reactive ATP-biotin probe can be determined. Living cells can be treated with a compound of Formula I, followed by lysis treatment with ATP-biotin and western blotting for BTK and HCK and/or LYN and/or SRC. It can be determined whether the compound tested blocks ATP binding to HCK and/or LYN and/or SRC at one or more particular concentrations, and whether the compound tested blocks ATP binding to BTK at the one or more concentrations. In such an assay, blocking of binding to ATP can be determined by lack of a detectable band on Western blot when performed under the conditions described in Example 1. In some embodiments, the compound blocks ATP binding to HCK and/or LYN and/or SRC at a concentration at least 10-fold, at least 30-fold, at least 50-fold, at least 100-fold, at least 150-fold, at least 200-fold, at least 250-fold, at least 300-fold, at least 350-fold, at least 400-fold, at least 450-fold, at least 500-fold, at least 750-fold, or at least 1000-fold, lower than the concentration at which it blocks ATP binding to BTK under equivalent conditions. In some embodiments, a compound blocks ATP binding to HCK and/or LYN and/or SRC at a concentration at least 10-fold lower than the concentration at which it blocks ATP binding to Bruton's Tyrosine Kinase (BTK) under equivalent conditions. In some embodiments, the compound blocks ATP binding to and/or LYN and/or SRC at a concentration of 1 am as determined by absence of a detectable band in a native protein kinase activity profiling assay, e.g., as described in Example 1. In some embodiments, the compound does not block ATP binding to BTK at a concentration of 1 am as determined by presence of a detectable band in a native protein kinase activity profiling assay, e.g., as described in Example 1. In some embodiments, the compound blocks ATP binding to and/or LYN and/or SRC at a concentration of 0.1 am as determined by absence of a detectable band in a native protein kinase activity profiling assay, e.g., as described in Example 1. In some embodiments, the compound does not block ATP binding to BTK at a concentration of 0.1 am as determined by presence of a detectable band in a native protein kinase activity profiling assay, e.g., as described in Example 1.

The term "MYD88 mutation" means any change or difference in the nucleic acid or protein sequence of MYD88 as compared to the wild type sequence that results in the activation of MYD88 which leads to the activation of NF-κB. Mutations include, but are not limited to, nonsense mutations, missense mutations, frameshift mutations, rearrangement mutations, insertion mutations and deletion mutations. In some embodiments, the mutation is a somatic mutation at position 38182641 in chromosome 3p22.2 which results in a single nucleotide change from T→C in the myeloid differentiation primary response (MYD88) gene, and a predicted non-synonymous change at amino acid position 265 from leucine to proline (L265P). In some embodiments, the mutation is another activating mutation in MYD88, such as V217F, W218R, I220T, S222R, M232T, S243N, T294P. Signaling studies show that SU-DHL-2 lymphoma cells that express the serine to arginine mutation at amino acid position 222 also have upregulated HCK (Yang et al, Blood 2016). In some embodiments, Sanger sequencing, whole exome or whole genome sequencing can be used to identify somatic mutations in MYD88.

One skilled in the art will appreciate that many suitable methods, in addition to and including the ones discussed in the examples, can be used to detect mutations in the MYD88 gene. Detection methods that can be used include, but are not limited to, direct sequencing, DNAchip technologies, mass spectroscopy, polymerase chain reaction (PCR), allele specific polymerase chain reaction, real time polymerase chain reaction, reverse transcriptase PCR, electrophoretic mobility, nucleic acid hybridization, fluorescent in situ hybridization, and denaturing high performance liquid chromatography. In some embodiments, mutations in the MYD88 gene may be detected by allele specific polymerase chain reaction (AS-PCR), e.g., as described in WO2013/006443. The term "MYD88 mutated disease" or "disease associated with mutated MYD88" means any disease in a subject that is related to a change or difference in the nucleic acid or protein sequence of MYD88 as compared to the wild type sequence that results in the activation of MYD88 which leads to the activation of NF-κB. In some embodiments, mutated MYD88 is associated with Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia. In some embodiments, mutated MYD88 is associated with susceptibility to infectious disease. In some embodiments, mutated MYD88 is associated with susceptibility to autoimmune disease. The terms "condition," "disease," and "disorder" are used interchangeably.

One or more symptoms or clinical features of LPL include anemia, hyper-viscosity, neuropathy, coagulopathies, splenomegaly, hepatomegaly, adenopathy, and an IgM serum paraprotein. In addition, the subject may also present one or more of the following clinical features or symptoms of other B cell neoplasms: asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia. A subject suspected of having one or more of Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia may be assessed for the presence of a mutation in the gene encoding MYD88, e.g., at position 38182641 in chromosome 3p22.2, as well as other activating mutations in MYD88 (including but not limited to V217F, W218R, I220T, S222R, M232T, S243N, and T294P).

Non-limiting examples of the biological sample obtained from the subject to determine whether the subject has a mutation in the gene encoding MYD88, e.g., at position 38182641 in chromosome 3p22.2 as well as other activating mutations in MYD88 (including but not limited to V217F, W218R, I220T, S222R, M232T, S243N, and T294P) include bone marrow, lymph node, spleen or blood. Obtaining a biological sample of a subject means taking possession of a biological sample of the subject. Obtaining a biological sample from a subject means removing a biological sample from the subject. Therefore, the person obtaining a biological sample of a subject and determining the presence of the mutation in the sample does not necessarily obtain the biological sample from the subject. In some embodiments, the biological sample may be removed from the subject by a medical practitioner (e.g., a doctor, nurse, or a clinical laboratory practitioner), and then provided to the person determining the presence of the mutation. The biological sample may be provided to the person determining the mutation by the subject or by a medical practitioner (e.g., a doctor, nurse, or a clinical laboratory practitioner). In some embodiments, the person determining the mutation obtains a biological sample from the subject by removing the sample from the subject.

In some embodiments, treatment further includes administering to the subject an agent, e.g., an anti-cancer agent, in combination with a compound described herein. In some embodiments, treatment further includes administering to the subject one or more of bendamustine, fludarabine, bortezomib, or idelalisib. In some embodiments, treatment further includes administering to the subject one or more of a proteasome inhibitor (e.g., bortezomib, carfilzomib, ixazomib or oprozomib), a monoclonal antibody (e.g., rituximab, daratumumab, ofatumumab or obinituzumab), an alkylator drug (e.g., bendamustine, cyclophosphamide), a nucleoside analogue (e.g., fludarabine or cladribine), an MTOR inhibitor (e.g., everolimus), a BTK inhibitor (e.g., ibrutinib, acalabrutinib or BGB-3111), a BCR inhibitor (e.g., a SYK inhibitor) and/or an immunomodulating agent (e.g., thalidomide or lenalidomide). In some embodiments, the anti-cancer agent is a monoclonal antibody, e.g., rituximab. In some embodiments, the anti-cancer agent is a chemotherapeutic drug such as chlorambucil, cyclophosphamide, or vincristine or thalidomide. Corticosteroids, such as Prednisone, may also be used in combination. Plasmapheresis can be used to treat the hyperviscosity syndrome by removing the paraprotein from the blood. Autologous bone marrow transplantation may be used in combination with compounds described herein. In some embodiments, treatment further includes administering to the subject an agent that inhibits LYN and/or SRC.

When administered to a subject, effective amounts of the therapeutic agent will depend on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of a MYD88 mutated disease, such as Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, immune privileged lymphomas that include testicular lymphoma, marginal zone lymphoma, and chronic lymphocytic leukemia, an effective amount of a selective HCK inhibitor is that amount which slows the progression of the disease, halts the progression of the disease, or reverses the progression of the disease. An effective amount includes, but is not limited to, that amount necessary to slow, reduce, inhibit, ameliorate or reverse one or more symptoms associated with the MYD88 mutated disease. In some embodiments, such terms refer to a reduction in the levels of IgM serum paraprotein, anemia, hyper-viscosity, neuropathy, coagulopathies, splenomegaly, hepatomegaly, and adenopathy.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

Pharmaceutical preparations and compounds are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present invention may include or be diluted into a pharmaceutically-acceptable carrier. The term "pharmaceutically-acceptable carrier" as used herein means one or more compatible fillers, diluants or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

Chemistry Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$,

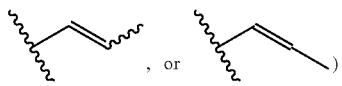

, or

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NRCO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^a$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOCl$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a mono-substituted amino or a disubstituted amino group.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2$H), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$, —C(=$NR^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)($OR^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is Bn, Boc, Cbz, Fmoc, trifluoroacetyl, triphenylmethyl, acetyl, or Ts.

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "hydrocarbon chain" refers to a substituted or unsubstituted, divalent, alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain $-C^AH(C^BH_2C^CH_3)-$ includes one chain atom $C^A$, one hydrogen atom on $C^A$, and non-chain substituent $-(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, $-CH(C_2H_5)-$ is a $C_1$ hydrocarbon chain, and

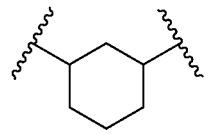 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., $-(CH_2)_4-$). A hydrocarbon chain may also be unsaturated and include one or more $C=C$ and/or $C\equiv C$ bonds anywhere in the hydrocarbon chain. For instance, $-CH=CH-(CH_2)_2-$, $-CH_2-C\equiv C-CH_2-$, and $-C\equiv C-CH=CH-$ are all examples of a unsubstituted and unsaturated hydrocarbon chain. In certain embodiments, the hydrocarbon chain is unsubstituted (e.g., $-C\equiv C-$ or $-(CH_2)_4-$). In certain embodiments, the hydrocarbon chain is substituted (e.g., $-CH(C_2H_5)-$ and $-CF_2-$). Any two substituents on the hydrocarbon chain may be joined to form an optionally substituted carbocyclyl, optionally substituted heterocyclyl, optionally substituted aryl, or optionally substituted heteroaryl ring. For instance,

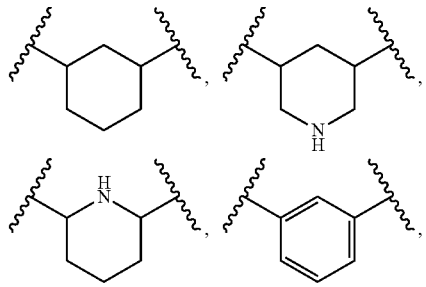

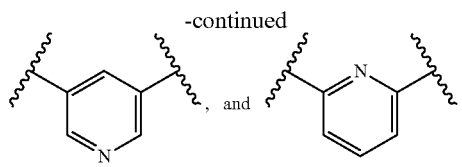

are all examples of a hydrocarbon chain. In contrast, in certain embodiments,

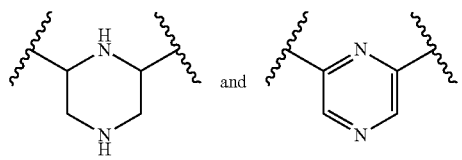 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

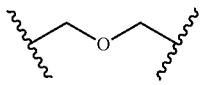

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4} \text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

Compounds Useful in the Methods

In certain embodiments, a compound useful in a method described herein is of Formula (I):

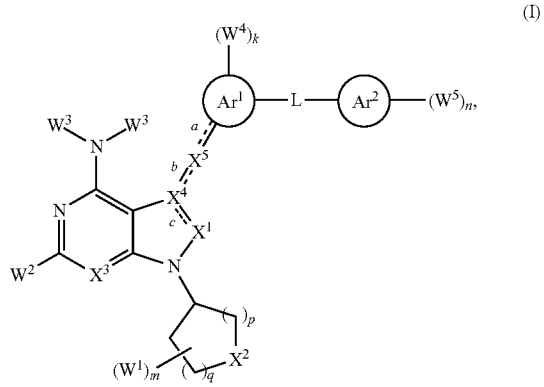

(I)

or a pharmaceutically acceptable salt, solvate, hydrate, polymorph, co-crystal, tautomer, stereoisomer, isotopically labeled derivative, or prodrug thereof, wherein: $Ar^1$ is absent, substituted or unsubstituted carbocyclyl, substituted or unsubstituted heterocycyl, substituted or unsubstituted aryl, or substituted or unsubstituted heteroaryl;

each instance of $W^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic ring, or substituted or unsubstituted heteroaryl ring;

k is 0, 1, 2, 3, or 4, as valency permits;

L is absent, —O—, —S—, —$NR^b$—, —C($R^c$)$_2$—, —$NR^bC$(=O)—, —C(=O)$NR^b$—, —OC(=O)—, —C(=O)O—, or a substituted or unsubstituted, $C_{1-6}$ hydrocarbon chain, optionally wherein one or more chain atoms of the hydrocarbon chain are independently replaced with —O—, —S—, —$NR^b$—, =N—, —N=, or —C(=O)—;

each instance of $R^b$ is independently hydrogen, substituted or unsubstituted $C_{1-6}$ alkyl, or a nitrogen protecting group;

$Ar^2$ is substituted or unsubstituted aryl or substituted or unsubstituted heteroaryl;

each instance of $W^5$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^aC$(=O)$R^a$, —$NR^aC$(=O)$OR^a$, —$NR^aC$(=O)N($R^a$)$_2$, —OC(=O)$R^a$, —OC(=O)$OR^a$, or —OC(=O)N($R^a$)$_2$;

n is 0, 1, 2, 3, 4, or 5, as valency permits;

bond a is a single or double bond, as valency permits;

$X^5$ is absent, —O—, —S—, —$NR^b$—, =N—, —N=, —C($R^c$)$_2$—, —$NR^bC$(=O)—, —C(=O)$NR^b$—, —OC(=O)—, —C(=O)O—, or a substituted or unsubstituted, $C_{1-6}$ hydrocarbon chain, optionally wherein one or more chain atoms of the hydrocarbon chain are independently replaced with —O—, —S—, —$NR^b$—, =N—, —N=, or —C(=O)—;

bond b is a single or double bond, as valency permits;

$X^4$ is C, $CR^c$, or N;

bond c is a single or double bond, as valency permits;

$X^1$ is $CR^c$, N, —C(=O)—, —S(=O)$_2$—, or —P(=O)($R^a$)—;

each instance of $R^c$ is independently hydrogen, halogen, substituted or unsubstituted $C_{1-6}$ alkyl, or —$OR^d$;

each instance of $R^d$ is independently hydrogen, substituted or unsubstituted $C_{1-6}$ alkyl, or an oxygen protecting group;

$X^2$ is —C($R^e$)$_2$— or —N($R^f$)—;

each instance of $R^e$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^f$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, or a nitrogen protecting group;

each instance of W$^1$ is independently halogen, substituted or unsubstituted C$_{1-6}$ alkyl, or —OR$^d$, or two instances of W$^1$ at the same carbon atom are joined to form =O;

m is 0, 1, 2, 3, 4, 5, 6, 7, 8, 9, 10, or 11, as valency permits;
p is 1 or 2;
q is 1 or 2;
X$^3$ is CR$^h$ or N;
R$^h$ is hydrogen, halogen, substituted or unsubstituted C$_{1-6}$ alkyl, or —OR$^d$;
W$^2$ is hydrogen, halogen, substituted or unsubstituted C$_{1-6}$ alkyl, or —OR$^d$;
each instance of W$^3$ is independently hydrogen, substituted or unsubstituted C$_{1-6}$ alkyl, or a nitrogen protecting group.

In certain embodiments, a compound useful in a method described herein is of Formula (II):

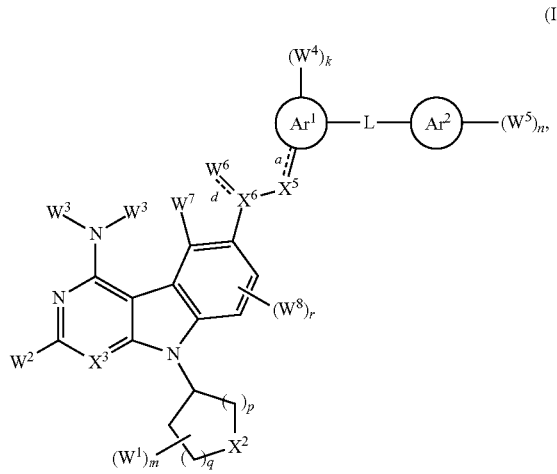

(II)

or a pharmaceutically acceptable salt, solvate, hydrate, polymorph, co-crystal, tautomer, stereoisomer, isotopically labeled derivative, or prodrug thereof, wherein:

Ar$^1$ is absent, substituted or unsubstituted carbocyclyl, substituted or unsubstituted heterocycyl, substituted or unsubstituted aryl, or substituted or unsubstituted heteroaryl;

each instance of W$^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted heterocyclic ring, or substituted or unsubstituted heteroaryl ring;

k is 0, 1, 2, 3, or 4, as valency permits;

L is absent, —O—, —S—, —NR$^b$—, —C(R$^c$)$_2$—, —NR$^b$C(=O)—, —C(=O)NR$^b$—, —OC(=O)—, —C(=O)O—, or a substituted or unsubstituted, C$_{1-6}$ hydrocarbon chain, optionally wherein one or more chain atoms of the hydrocarbon chain are independently replaced with —O—, —S—, —NR$^b$—, =N—, —N=, or —C(=O)—;

each instance of R$^b$ is independently hydrogen, substituted or unsubstituted C$_{1-6}$ alkyl, or a nitrogen protecting group;

Ar$^2$ is substituted or unsubstituted aryl or substituted or unsubstituted heteroaryl;

each instance of W$^5$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

n is 0, 1, 2, 3, 4, or 5, as valency permits;
bond a is a single or double bond, as valency permits;
X$^5$ is absent, —O—, —S—, —NR$^b$—, =N—, —N=, —C(R$^c$)$_2$—, —NR$^b$C(=O)—, —C(=O)NR$^b$—, —OC(=O)—, —C(=O)O—, or a substituted or unsubstituted, C$_{1-6}$ hydrocarbon chain, optionally wherein one or more chain atoms of the hydrocarbon chain are independently replaced with —O—, —S—, —NR$^b$—, =N—, —N=, or —C(=O)—;

each instance of R$^c$ is independently hydrogen, halogen, substituted or unsubstituted C$_{1-6}$ alkyl, or —OR$^d$;

each instance of R$^d$ is independently hydrogen, substituted or unsubstituted C$_{1-6}$ alkyl, or an oxygen protecting group;

X$^2$ is —C(R$^e$)$_2$— or —N(R$^f$)—;

each instance of R$^e$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^f$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, or a nitrogen protecting group;

each instance of W$^1$ is independently halogen, substituted or unsubstituted C$_{1-6}$ alkyl, or —OR$^d$, or two instances of W$^1$ at the same carbon atom are joined to form =O;

m is 0, 1, 2, 3, 4, 5, 6, 7, 8, 9, 10, or 11, as valency permits;
p is 1 or 2;
q is 1 or 2;
X$^3$ is CR$^h$ or N;
R$^h$ is hydrogen, halogen, substituted or unsubstituted C$_{1-6}$ alkyl, or —OR$^d$;
W$^2$ is hydrogen, halogen, substituted or unsubstituted C$_{1-6}$ alkyl, or —OR$^d$;
each instance of W$^3$ is independently hydrogen, substituted or unsubstituted C$_{1-6}$ alkyl, or a nitrogen protecting group;
X$^6$ is absent, C, CR$^c$, or N;
bond d is absent, a single bond, or a double bond, as valency permits;
W$^6$ is absent, or W$^6$ and W$^7$ are joined to form substituted or unsubstituted carbocyclyl, substituted or unsubstituted heterocyclyl, substituted or unsubstituted aryl, or substituted or unsubstituted heteroaryl;
W$^7$ is hydrogen, halogen, substituted or unsubstituted C$_{1-6}$ alkyl, or —OR$^d$;
each instance of W8 is independently halogen, substituted or unsubstituted C$_{1-6}$ alkyl, or —OR$^d$; and
r is 0, 1, or 2.

In certain embodiments, Ar$^1$ is absent. In certain embodiments, Ar$^1$ is substituted or unsubstituted carbocyclyl (e.g., substituted or unsubstituted, 3- to 7-membered, monocyclic carbocyclyl). In certain embodiments, Ar$^1$ is substituted or unsubstituted cyclopropyl, substituted or unsubstituted cyclobutyl, substituted or unsubstituted cyclopentyl, or substituted or unsubstituted cyclohexyl. In certain embodiments, Ar$^1$ is substituted or unsubstituted heterocyclyl (e.g., substituted or unsubstituted, 3- to 7-membered, monocyclic heterocyclyl, wherein one, two, or three atoms in the heterocyclic ring system are independently nitrogen, oxygen, or sulfur). In certain embodiments, Ar$^1$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, Ar$^1$ is substituted or unsubstituted aryl (e.g., substituted or unsubstituted 6- to 14-membered aryl). In certain embodiments, Ar$^1$ is unsubstituted phenyl. In certain embodiments, Ar$^1$ is substituted phenyl. In certain embodiments, Ar$^1$ is substituted or unsubstituted heteroaryl. In certain embodiments, Ar$^1$ is substituted or unsubstituted, 5- to 6-membered, monocyclic heteroaryl, wherein one, two, three, or four atoms in the heteroaryl ring system are independently nitrogen, oxygen, or sulfur. In certain embodiments, Ar$^1$ is substituted or unsubstituted, 9- to 10-membered, bicyclic heteroaryl, wherein one, two, three, or four atoms in the heteroaryl ring system are independently nitrogen, oxygen, or sulfur.

When two or more instances of W$^4$ are present in a compound described herein, any two instances of W$^4$ may be the same or different from each other. In certain embodiments, at least one instance of W$^4$ is halogen (e.g., F, Cl, Br, or I). In certain embodiments, at least one instance of W$^4$ is substituted or unsubstituted alkyl. In certain embodiments, at least one instance of W$^4$ is substituted or unsubstituted C$_{1-6}$ alkyl. In certain embodiments, at least one instance of W$^4$ is Me. In certain embodiments, at least one instance of W$^4$ is substituted methyl, Et, substituted ethyl, Pr, substituted propyl, Bu, or substituted butyl. In certain embodiments, at least one instance of W$^4$ is substituted or unsubstituted alkenyl (e.g., substituted or unsubstituted C$_{2-6}$ alkenyl). In certain embodiments, at least one instance of W$^4$ is substituted or unsubstituted alkynyl (e.g., substituted or unsubstituted C$_{2-6}$ alkynyl). In certain embodiments, at least one instance of W$^4$ is substituted or unsubstituted carbocyclyl (e.g., substituted or unsubstituted, 3- to 7-membered, monocyclic carbocyclyl). In certain embodiments, at least one instance of W$^4$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of W$^4$ is substituted or unsubstituted heterocyclyl (e.g., substituted or unsubstituted, 3- to 7-membered, monocyclic heterocyclyl, wherein one, two, or three atoms in the heterocyclic ring system are independently nitrogen, oxygen, or sulfur). In certain embodiments, at least one instance of W$^4$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of W$^4$ is substituted or unsubstituted aryl (e.g., substituted or unsubstituted, 6- to 10-membered aryl). In certain embodiments, at least one instance of W$^4$ is unsubstituted phenyl. In certain embodiments, at least one instance of W$^4$ is substituted phenyl. In certain embodiments, at least one instance of W$^4$ is substituted or unsubstituted heteroaryl. In certain embodiments, at least one instance of W$^4$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of W$^4$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of W$^4$ is —OR$^a$ (e.g., —OH, —O(substituted or unsubstituted alkyl), or —O(substituted or unsubstituted phenyl)). In certain embodiments, at least one instance of W$^4$ is —SR$^a$ (e.g., —SH, —S(substituted or unsubstituted alkyl), or —S(substituted or unsubstituted phenyl)). In certain embodiments, at least one instance of W$^4$ is —N(R$^a$)$_2$ (e.g., —NH$_2$, —NH(substituted or unsubstituted alkyl), or —N(substituted or unsubstituted alkyl)-(substituted or unsubstituted alkyl)). In certain embodiments, at least one instance of W$^4$ is —CN or —SCN. In certain embodiments, at least one instance of W$^4$ is —NO$_2$. In certain embodiments, at least one instance of W$^4$ is —C(=NR$^a$)R$^a$, —C(=NR$^a$)OR$^a$, or —C(=NR$^a$)N(R$^a$)$_2$. In certain embodiments, at least one instance of W$^4$ is —C(=O)R$^a$ (e.g., —C(=O)(substituted or unsubstituted alkyl) or —C(=O)(substituted or unsubstituted phenyl)). In certain embodiments, at least one instance of W$^4$ is —C(=O)OR$^a$ (e.g., —C(=O)OH, —C(=O)O(substituted or unsubstituted alkyl), or —C(=O)O(substituted or unsubstituted phenyl)). In certain embodiments, at least one instance of W$^4$ is —C(=O)N(R$^a$)$_2$ (e.g., —C(=O)NH$_2$, —C(=O)NH (substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $W^4$ is —NR$^a$C(=O)R$^a$(e.g., —NHC(=O)(substituted or unsubstituted alkyl) or —NHC(=O)(substituted or unsubstituted phenyl)). In certain embodiments, at least one instance of $W^4$ is —NR$^a$C(=O)OR$^a$. In certain embodiments, at least one instance of $W^4$ is —NR$^a$C(=O)N(R$^a$)$_2$ (e.g., —NHC(=O)NH$_2$, —NHC(=O)NH(substituted or unsubstituted alkyl)). In certain embodiments, at least one instance of $W^4$ is —OC(=O)R$^a$ (e.g., —OC(=O)(substituted or unsubstituted alkyl) or —OC(=O)(substituted or unsubstituted phenyl)), —OC(=O)OR$^a$ (e.g., —OC(=O)O(substituted or unsubstituted alkyl) or —OC(=O)O(substituted or unsubstituted phenyl)), or —OC(=O)N(R$^a$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

When two or more instances of R$^a$ are present in a compound described herein, any two instances of R$^a$ may be the same or different from each other. In certain embodiments, at least one instance of R$^a$ is H. In certain embodiments, each instance of R$^a$ is H. In certain embodiments, at least one instance of R$^a$ is substituted or unsubstituted alkyl (e.g., substituted or unsubstituted $C_{1-6}$ alkyl (e.g., Me)). In certain embodiments, at least one instance of R$^a$ is substituted or unsubstituted acyl, substituted or unsubstituted alkenyl (e.g., substituted or unsubstituted $C_{2-6}$ alkenyl), or substituted or unsubstituted alkynyl (e.g., substituted or unsubstituted $C_{2-6}$ alkynyl). In certain embodiments, at least one instance of R$^a$ is substituted or unsubstituted carbocyclyl (e.g., substituted or unsubstituted, 3- to 7-membered, monocyclic carbocyclyl), substituted or unsubstituted heterocyclyl (e.g., substituted or unsubstituted, 3- to 7-membered, monocyclic heterocyclyl, wherein one, two, or three atoms in the heterocyclic ring system are independently nitrogen, oxygen, or sulfur), substituted or unsubstituted aryl (e.g., substituted or unsubstituted phenyl), or substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur). In certain embodiments, at least one instance of R$^a$ is a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of R$^a$ are joined to form a substituted or unsubstituted heterocyclic or substituted or unsubstituted heteroaryl ring.

In certain embodiments, k is 0. In certain embodiments, k is 1, 2, 3, or 4, as valency permits.

In certain embodiments, when L is -(an unsymmetrical divalent moiety)-, the bond on the left-hand side of "-(an unsymmetrical divalent moiety)-" is directly attached to Ar$^1$, and the bond on the right-hand side of "-(an unsymmetrical divalent moiety)-" is directly attached to Ar$^2$. In certain embodiments, L is absent. In certain embodiments, L is —O—. In certain embodiments, L is —S—. In certain embodiments, L is —NR$^b$— (e.g., —NH—, —N(substituted or unsubstituted $C_{1-6}$ alkyl)-, or —N(nitrogen protecting group)-). In certain embodiments, L is —C(R$^c$)$_2$— (e.g., —CH$_2$—). In certain embodiments, L is —NR$^b$C(=O)— (e.g., —NHC(=O)—, —N(substituted or unsubstituted $C_{1-6}$ alkyl)C(=O)—, or —N(nitrogen protecting group)C(=O)—) or —C(=O)NR$^b$— (e.g., —C(=O)NH—, —C(=O)N(substituted or unsubstituted $C_{1-6}$ alkyl)-, or —C(=O)N(nitrogen protecting group)-). In certain embodiments, L is —OC(=O)— or —C(=O)O—. In certain embodiments, L is a substituted or unsubstituted, $C_{1-6}$ hydrocarbon chain, optionally wherein one or more chain atoms of the hydrocarbon chain are independently replaced with —O—, —S—, —NR$^b$—, =N—, —N=, or —C(=O)—.

When two or more instances of R$^b$ are present in a compound described herein, any two instances of R$^b$ may be the same or different from each other. In certain embodiments, at least one instance of R$^b$ is H. In certain embodiments, each instance of R$^b$ is H. In certain embodiments, at least one instance of R$^b$ is substituted or unsubstituted $C_{1-6}$ alkyl (e.g., Me). In certain embodiments, at least one instance of R$^b$ is a nitrogen protecting group (e.g., Bn, Boc, Cbz, Fmoc, trifluoroacetyl, triphenylmethyl, acetyl, or Ts).

In certain embodiments, Ar$^2$ is substituted or unsubstituted aryl (e.g., substituted or unsubstituted 6- to 14-membered aryl). In certain embodiments, Ar$^2$ is unsubstituted phenyl. In certain embodiments, Ar$^2$ is substituted phenyl. In certain embodiments, Ar$^2$ is substituted or unsubstituted heteroaryl. In certain embodiments, Ar$^2$ is substituted or unsubstituted, 5- to 6-membered, monocyclic heteroaryl, wherein one, two, three, or four atoms in the heteroaryl ring system are independently nitrogen, oxygen, or sulfur. In certain embodiments, Ar$^2$ is substituted or unsubstituted, 9- to 10-membered, bicyclic heteroaryl, wherein one, two, three, or four atoms in the heteroaryl ring system are independently nitrogen, oxygen, or sulfur.

When two or more instances of $W^5$ are present in a compound described herein, any two instances of $W^5$ may be the same or different from each other. In certain embodiments, at least one instance of $W^5$ is halogen (e.g., F, Cl, Br, or I). In certain embodiments, at least one instance of $W^5$ is substituted or unsubstituted alkyl. In certain embodiments, at least one instance of $W^5$ is substituted or unsubstituted $C_{1-6}$ alkyl. In certain embodiments, at least one instance of $W^5$ is Me. In certain embodiments, at least one instance of $W^5$ is substituted methyl, Et, substituted ethyl, Pr, substituted propyl, Bu, or substituted butyl. In certain embodiments, at least one instance of $W^5$ is substituted or unsubstituted alkenyl (e.g., substituted or unsubstituted $C_{2-6}$ alkenyl). In certain embodiments, at least one instance of $W^5$ is substituted or unsubstituted alkynyl (e.g., substituted or unsubstituted $C_{2-6}$ alkynyl). In certain embodiments, at least one instance of $W^5$ is substituted or unsubstituted carbocyclyl (e.g., substituted or unsubstituted, 3- to 7-membered, monocyclic carbocyclyl). In certain embodiments, at least one instance of $W^5$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of $W^5$ is substituted or unsubstituted heterocyclyl (e.g., substituted or unsubstituted, 3- to 7-membered, monocyclic heterocyclyl, wherein one, two, or three atoms in the heterocyclic ring system are independently nitrogen, oxygen, or sulfur). In certain embodiments, at least one instance of $W^5$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $W^5$ is substituted or unsubstituted aryl (e.g., substituted or unsubstituted, 6- to 10-membered aryl). In certain embodiments, at least one instance of $W^5$ is unsubstituted phenyl. In certain embodiments, at least one instance of $W^5$ is substituted phenyl. In certain embodiments, at least one instance of $W^5$ is substituted or unsubstituted heteroaryl. In certain embodiments, at least one instance of $W^5$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of $W^5$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of $W^5$ is —$OR^a$ (e.g., —OH, —O(substituted or unsubstituted alkyl), or —O(substituted or unsubstituted phenyl)). In certain embodiments, at least one instance of $W^5$ is —$SR^a$ (e.g., —SH, —S(substituted or unsubstituted alkyl), or —S(substituted or unsubstituted phenyl)). In certain embodiments, at least one instance of $W^5$ is —$N(R^a)_2$ (e.g., —$NH_2$, —NH(substituted or unsubstituted alkyl), or —N(substituted or unsubstituted alkyl)-(substituted or unsubstituted alkyl)). In certain embodiments, at least one instance of $W^5$ is —CN or —SCN. In certain embodiments, at least one instance of $W^5$ is —$NO_2$. In certain embodiments, at least one instance of W is —$C(=NR^a)R^a$, —$C(=NR^a)OR^a$, or —$C(=NR^a)N(R^a)_2$. In certain embodiments, at least one instance of $W^5$ is —$C(=O)R^a$ (e.g., —C(=O)(substituted or unsubstituted alkyl) or —C(=O)(substituted or unsubstituted phenyl)). In certain embodiments, at least one instance of $W^5$ is —$C(=O)OR^a$ (e.g., —C(=O)OH, —C(=O)O(substituted or unsubstituted alkyl), or —C(=O)O(substituted or unsubstituted phenyl)). In certain embodiments, at least one instance of $W^5$ is —$C(=O)N(R^a)_2$ (e.g., —$C(=O)NH_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $W^5$ is —$NR^aC(=O)R^a$(e.g., —NHC(=O)(substituted or unsubstituted alkyl) or —NHC(=O)(substituted or unsubstituted phenyl)). In certain embodiments, at least one instance of $W^5$ is —$NR^aC(=O)OR^a$. In certain embodiments, at least one instance of $W^5$ is —$NR^aC(=O)N(R^a)_2$ (e.g., —$NHC(=O)NH_2$, —NHC(=O)NH(substituted or unsubstituted alkyl)). In certain embodiments, at least one instance of $W^5$ is —$OC(=O)R^a$ (e.g., —OC(=O)(substituted or unsubstituted alkyl) or —OC(=O)(substituted or unsubstituted phenyl)), —$OC(=O)OR^a$ (e.g., —OC(=O)O(substituted or unsubstituted alkyl) or —OC(=O)O(substituted or unsubstituted phenyl)), or —$OC(=O)N(R^a)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

In certain embodiments, n is 0. In certain embodiments, n is 1, 2, 3, 4, or 5, as valency permits.

In certain embodiments, when $X^5$ is ==(an unsymmetrical divalent moiety)==, the bond == on the left-hand side of "==(an unsymmetrical divalent moiety)==" is directly attached to $X^4$, and the bond == on the right-hand side of "==(an unsymmetrical divalent moiety)==" is directly attached to $Ar^1$. In certain embodiments, $X^5$ is absent. In certain embodiments, $X^5$ is —O—. In certain embodiments, $X^5$ is —S—. In certain embodiments, $X^5$ is —$NR^b$— (e.g., —NH—, —N(substituted or unsubstituted $C_{1-6}$ alkyl)-, or —N(nitrogen protecting group)-). In certain embodiments, $X^5$ is =N— or —N=. In certain embodiments, $X^5$ is —$C(R^c)_2$— (e.g., —$CH_2$—). In certain embodiments, $X^5$ is —$NR^bC(=O)$— (e.g., —NHC(=O)—, —N(substituted or unsubstituted $C_{1-6}$ alkyl)C(=O)—, or —N(nitrogen protecting group)C(=O)—) or —$C(=O)NR^b$— (e.g., —C(=O)NH—, —C(=O)N(substituted or unsubstituted $C_{1-6}$ alkyl)-, or —C(=O)N(nitrogen protecting group)-). In certain embodiments, $X^5$ is —OC(=O)— or —C(=O)O—. In certain embodiments, $X^5$ is a substituted or unsubstituted, $C_{1-6}$ hydrocarbon chain, optionally wherein one or more chain atoms of the hydrocarbon chain are independently replaced with —O—, —S—, —$NR^b$—, =N—, —N=, or —C(=O)—. In certain embodiments, $X^5$ is =CH— or —CH=. In certain embodiments, $X^5$ is a substituted or unsubstituted, $C_2$ hydrocarbon chain. In certain embodiments, $X^5$ is —C≡C—. In certain embodiments, $X^5$ is unsubstituted ethylene or unsubstituted vinylene. In certain $X^5$ is =N—V—, wherein V is absent, —$C(R^c)_2$—, —C(=O)—, —O—, or —$N(R^b)$—. In certain embodiments, $X^5$ is =N—$CH_2$—, =N—C(=O)—, =N—O—, or =N—NH—. In certain embodiments, $X^5$ is a substituted or unsubstituted, $C_3$ hydrocarbon chain. In certain embodiments, $X^5$ is —C≡C—$CH_2$—. In certain embodiments, $X^5$ is unsubstituted n-propylene, —CH=CH—$CH_2$—, —$CH_2$—CH=CH—, or —$CH_2$—C≡C—. In certain embodiments, $X^5$ is a substituted or unsubstituted, $C_4$ hydrocarbon chain, optionally one or two chain atoms of the hydrocarbon chain are independently replaced with —O—, —S—, —$NR^b$—, =N—, —N=, or —C(=O)—. In certain embodiments, $X^5$ is —C≡C—$CH_2$—O—. In certain embodiments, $X^5$ is —C≡C—$CH_2$—S—, —C≡C—$CH_2$—$NR^b$—, —C≡C—$CH_2$—$CH_2$—, —CH=CH—$CH_2$—O—, —CH=CH—$CH_2$—S—, —CH=CH—$CH_2$—$NR^b$—, —CH=CH—$CH_2$—$CH_2$—, —$CH_2$—$CH_2$—$CH_2$—O—, —$CH_2$—$CH_2$—$CH_2$—S—, —$CH_2$—$CH_2$—$CH_2$—$NR^b$—, or —$CH_2$—$CH_2$—$CH_2$—$CH_2$—. In certain embodiments, $X^5$ is a substituted or unsubstituted, $C_{5-6}$ hydrocarbon chain, optionally one, two, or three chain atoms of the hydrocarbon chain are independently replaced with —O—, —S—, —$NR^b$—, =N—, —N=, or —C(=O)—. In certain embodiments, $X^5$ is =N—V—C(=O)—$CH_2$—O—, wherein V is absent, —$C(R^c)_2$—, —C(=O)—, —O—, or —$N(R^b)$—. In certain embodiments, $X^5$ is =N—C(=O)—$CH_2$—O—, =N—$CH_2$—C(=O)—$CH_2$—O—, =N—O—C(=O)—$CH_2$—O—, or =N—NH—C(=O)—$CH_2$—O—.

In certain embodiments, $X^4$ is C. In certain embodiments, $X^4$ is $CR^c$. In certain embodiments, $X^4$ is CH. In certain embodiments, $X^4$ is N.

In certain embodiments, $X^1$ is $CR^c$. In certain embodiments, $X^1$ is CH. In certain embodiments, $X^1$ is N. In certain embodiments, $X^1$ is —C(=O)—. In certain embodiments, $X^1$ is —$S(=O)_2$—. In certain embodiments, $X^1$ is —$P(=O)(R^a)$— (e.g., —P(=O)(substituted or unsubstituted $C_{1-6}$ alkyl)- (e.g., —P(=O)(Me)-)).

When two or more instances of $R^c$ are present in a compound described herein, any two instances of $R^c$ may be the same or different from each other. In certain embodiments, at least one instance of $R^c$ is H. In certain embodiments, each instance of $R^c$ is H. In certain embodiments, at least one instance of $R^c$ is halogen (e.g., F, Cl, Br, or I). In certain embodiments, at least one instance of $R^c$ is substituted or unsubstituted $C_{1-6}$ alkyl (e.g., Me). In certain embodiments, at least one instance of $R^c$ is —OR$^d$ (e.g., —OH or —OMe).

When two or more instances of $R^d$ are present in a compound described herein, any two instances of $R^d$ may be the same or different from each other. In certain embodiments, at least one instance of $R^d$ is H. In certain embodiments, each instance of $R^d$ is H. In certain embodiments, at least one instance of $R^d$ is substituted or unsubstituted $C_{1-6}$ alkyl (e.g., Me). In certain embodiments, at least one instance of $R^d$ is an oxygen protecting group (e.g., silyl, TBDPS, TBDMS, TIPS, TES, TMS, MOM, THP, t-Bu, Bn, allyl, acetyl, pivaloyl, or benzoyl).

In certain embodiments, $X^2$ is —C($R^e$)$_2$—. In certain embodiments, $X^2$ is —CH($R^e$)—. In certain embodiments, $X^2$ is —CH$_2$—. In certain embodiments, $X^2$ is —N($R^f$)—. In certain embodiments, $X^2$ is —NH—.

The two instances of $R^e$ may be the same or different from each other. In certain embodiments, at least one instance of $R^e$ is H. In certain embodiments, each instance of $R^e$ is H. In certain embodiments, at least one instance of $R^e$ is halogen (e.g., F, Cl, Br, or I). In certain embodiments, at least one instance of $R^e$ is substituted or unsubstituted alkyl. In certain embodiments, at least one instance of $R^e$ is substituted or unsubstituted $C_{1-6}$ alkyl. In certain embodiments, at least one instance of $R^e$ is Me. In certain embodiments, at least one instance of $R^e$ is substituted methyl, Et, substituted ethyl, Pr, substituted propyl, Bu, or substituted butyl. In certain embodiments, at least one instance of $R^e$ is substituted or unsubstituted alkenyl (e.g., substituted or unsubstituted $C_{2-6}$ alkenyl). In certain embodiments, at least one instance of $R^e$ is substituted or unsubstituted alkynyl (e.g., substituted or unsubstituted $C_{2-6}$ alkynyl). In certain embodiments, at least one instance of $R^e$ is substituted or unsubstituted carbocyclyl (e.g., substituted or unsubstituted, 3- to 7-membered, monocyclic carbocyclyl). In certain embodiments, at least one instance of $R^e$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of $R^e$ is substituted or unsubstituted heterocyclyl. In certain embodiments, at least one instance of $R^e$ is substituted or unsubstituted, 3- to 7-membered, monocyclic heterocyclyl, wherein one, two, or three atoms in the heterocyclic ring system are independently nitrogen, oxygen, or sulfur. In certain embodiments, at least one instance of $R^e$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl. In certain embodiments, at least one instance of $R^e$ is substituted or unsubstituted piperazinyl (e.g., substituted or unsubstituted 1-piperazinyl). In certain

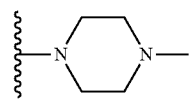 [SMILES: *N1CCN(C)CC1]

(substituted or unsubstituted $C_{1-6}$ alkyl)

(e.g., 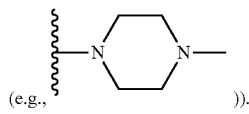 )).

In certain embodiments, at least one instance of $R^e$ is

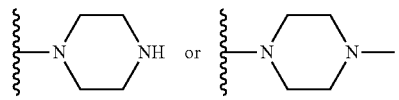

(nitrogen protecting group). In certain embodiments, at least one instance of $R^e$ is substituted or unsubstituted aryl (e.g., substituted or unsubstituted, 6- to 10-membered aryl). In certain embodiments, at least one instance of $R^e$ is unsubstituted phenyl. In certain embodiments, at least one instance of $R^e$ is substituted phenyl. In certain embodiments, at least one instance of $R^e$ is substituted or unsubstituted heteroaryl. In certain embodiments, at least one instance of $R^e$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of $R^e$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of $R^e$ is —OR$^a$ (e.g., —OH, —O(substituted or unsubstituted alkyl), or —O(substituted or unsubstituted phenyl)). In certain embodiments, at least one instance of $R^e$ is —SR$^a$ (e.g., —SH, —S(substituted or unsubstituted alkyl), or —S(substituted or unsubstituted phenyl)). In certain embodiments, at least one instance of $R^e$ is —N(R$^a$)$_2$ (e.g., —NH$_2$, —NH(substituted or unsubstituted alkyl), or —N(substituted or unsubstituted alkyl)-(substituted or unsubstituted alkyl)). In certain embodiments, at least one instance of $R^e$ is —CN or —SCN. In certain embodiments, at least one instance of $R^e$ is —NO$_2$. In certain embodiments, at least one instance of $R^e$ is —C(=NR$^a$)R$^a$, —C(=NR$^a$)OR$^a$, or —C(=NR$^a$)N(R$^a$)$_2$. In certain embodiments, at least one instance of $R^e$ is —C(=O)R$^a$. In certain embodiments, at least one instance of $R^e$ is —C(=O) (substituted or unsubstituted alkyl), —C(=O)(substituted or unsubstituted alkynyl), or —C(=O)(substituted or unsubstituted phenyl). In certain embodiments, at least one instance of $R^e$ is —C(=O)(substituted or unsubstituted alkenyl) (e.g., —C(=O)(substituted or unsubstituted $C_{2-6}$ alkenyl)). In certain embodiments, at least one instance of $R^e$ is —C(=O)(vinyl). In certain embodiments, at least one instance of $R^e$ is —C(=O)OR$^a$ (e.g., —C(=O)OH, —C(=O)O(substituted or unsubstituted alkyl), or —C(=O)O(substituted or unsubstituted phenyl)). In certain embodiments, at least one instance of $R^e$ is —C(=O)N(R$^a$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $R^e$ is —NR$^a$C(=O)R$^a$ (e.g., —NHC(=O)(substituted or unsubstituted alkyl) or —NHC(=O)(substituted or unsubstituted phenyl)). In certain embodiments, at least one instance of $R^e$ is —NR$^a$C(=O)OR$^a$. In certain embodiments, at least one instance of $R^e$ is —NR$^a$C(=O)N(R$^a$)$_2$ (e.g., —NHC(=O) NH$_2$, —NHC(=O)NH(substituted or unsubstituted alkyl)). In certain embodiments, at least one instance of $R^e$ is —OC(=O)R$^a$ (e.g., —OC(=O)(substituted or unsubstituted alkyl) or —OC(=O)(substituted or unsubstituted phenyl)), —OC(=O)OR$^a$ (e.g., —OC(=O)O(substituted or unsubstituted alkyl) or —OC(=O)O(substituted or unsubstituted phenyl)), or —OC(=O)N($R^a$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

In certain embodiments, $R^f$ is H. In certain embodiments, $R^f$ is substituted or unsubstituted alkyl. In certain embodiments, $R^f$ is substituted or unsubstituted $C_{1-6}$ alkyl. In certain embodiments, R is Me. In certain embodiments, R is substituted methyl, Et, substituted ethyl, Pr, substituted propyl, Bu, or substituted butyl. In certain embodiments, $R^f$ is substituted or unsubstituted alkenyl (e.g., substituted or unsubstituted $C_{2-6}$ alkenyl). In certain embodiments, $R^f$ is substituted or unsubstituted alkynyl (e.g., substituted or unsubstituted $C_{2-6}$ alkynyl). In certain embodiments, $R^f$ is substituted or unsubstituted carbocyclyl (e.g., substituted or unsubstituted, 3- to 7-membered, monocyclic carbocyclyl). In certain embodiments, $R^f$ is substituted or unsubstituted cyclopropyl, substituted or unsubstituted cyclobutyl, substituted or unsubstituted cyclopentyl, or substituted or unsubstituted cyclohexyl. In certain embodiments, $R^f$ is substituted or unsubstituted heterocyclyl. In certain embodiments, $R^f$ is substituted or unsubstituted, 3- to 7-membered, monocyclic heterocyclyl, wherein one, two, or three atoms in the heterocyclic ring system are independently nitrogen, oxygen, or sulfur. In certain embodiments, $R^f$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl. In certain embodiments, $R^f$ is substituted or unsubstituted piperazinyl (e.g., substituted or unsubstituted 1-piperazinyl). In certain embodiments, $R^f$ is

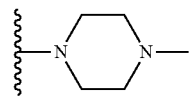

(substituted or unsubstituted $C_{1-6}$ alkyl)

(e.g., 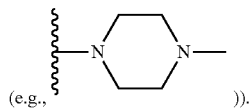 )).

In certain embodiments, $R^f$ is

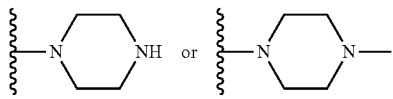

(nitrogen protecting group). In certain embodiments, $R^f$ is substituted or unsubstituted aryl (e.g., substituted or unsubstituted, 6- to 10-membered aryl). In certain embodiments, $R^f$ is unsubstituted phenyl. In certain embodiments, $R^f$ is substituted phenyl. In certain embodiments, $R^f$ is substituted or unsubstituted heteroaryl. In certain embodiments, $R^f$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^f$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^f$ is —C(=$NR^a$)$R^a$, —C(=$NR^a$)$OR^a$, or —C(=$NR^a$)N($R^a$)$_2$. In certain embodiments, $R^f$ is —C(=O)$R^a$. In certain embodiments, $R^f$ is —C(=O)(substituted or unsubstituted alkyl), —C(=O)(substituted or unsubstituted alkynyl), or —C(=O)(substituted or unsubstituted phenyl). In certain embodiments, $R^f$ is —C(=O)(substituted or unsubstituted alkenyl) (e.g., —C(=O)(substituted or unsubstituted $C_{2-6}$ alkenyl)). In certain embodiments, $R^f$ is —C(=O)(vinyl). In certain embodiments, R is —C(=O)$OR^a$ (e.g., —C(=O)OH, —C(=O)O(substituted or unsubstituted alkyl), or —C(=O)O(substituted or unsubstituted phenyl)). In certain embodiments, $R^f$ is —C(=O)N($R^a$)$_2$ (e.g., —C(=O)NH$_2$, —C(=O)NH(substituted or unsubstituted alkyl), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^f$ is a nitrogen protecting group (e.g., Bn, Boc, Cbz, Fmoc, trifluoroacetyl, triphenylmethyl, acetyl, or Ts).

When two or more instances of $W^1$ are present in a compound described herein, any two instances of $W^1$ may be the same or different from each other. In certain embodiments, at least one instance of $W^1$ is halogen (e.g., F, Cl, Br, or I). In certain embodiments, at least one instance of $W^1$ is substituted or unsubstituted $C_{1-6}$ alkyl (e.g., Me). In certain embodiments, at least one instance of $W^1$ is —$OR^d$ (e.g., —OH or —OMe). In certain embodiments, two instances of $W^1$ at the same carbon atom are joined to form =O. In certain embodiments, two instances of $W^1$ at one carbon atom are joined to form =O, and another two instances of $W^1$ at another carbon atom are joined to form =O.

In certain embodiments, m is 0. In certain embodiments, m is 1, 2, 3, 4, 5, 6, 7, 8, 9, 10, or 11, as valency permits.

In certain embodiments, p is 1. In certain embodiments, p is 2.

In certain embodiments, q is 1. In certain embodiments, q is 2.

In certain embodiments, $X^3$ is $CR^h$. In certain embodiments, $X^3$ is CH. In certain embodiments, $X^3$ is N.

In certain embodiments, $R^h$ is H. In certain embodiments, $R^h$ is halogen (e.g., F, Cl, Br, or I). In certain embodiments, $R^h$ is substituted or unsubstituted $C_{1-6}$ alkyl (e.g., Me). In certain embodiments, $R^h$ is —$OR^d$ (e.g., —OH or —OMe).

In certain embodiments, W is H. In certain embodiments, W is halogen (e.g., F, Cl, Br, or I). In certain embodiments, $W^2$ is substituted or unsubstituted $C_{1-6}$ alkyl (e.g., Me). In certain embodiments, W is —$OR^d$ (e.g., —OH or —OMe).

The two instances of $W^3$ may be the same or different from each other. In certain embodiments, at least one instance of $W^3$ is H. In certain embodiments, each instance of $W^3$ is H. In certain embodiments, at least one instance of $W^3$ is substituted or unsubstituted $C_{1-6}$ alkyl (e.g., Me). In certain embodiments, at least one instance of $W^3$ is a nitrogen protecting group (e.g., Bn, Boc, Cbz, Fmoc, trifluoroacetyl, triphenylmethyl, acetyl, or Ts).

In certain embodiments, $X^6$ is absent. In certain embodiments, $X^6$ is C. In certain embodiments, $X^6$ is $CR^c$ (e.g., CH). In certain embodiments, $X^6$ is N.

In certain embodiments, bond d is absent. In certain embodiments, bond d is a single bond or a double bond.

In certain embodiments, $W^6$ is absent. In certain embodiments, each one of $X^6$, $W^6$, and bonds d and e is absent.

In certain embodiments, $W^6$ and $W^7$ are joined to form substituted or unsubstituted carbocyclyl (e.g., substituted or unsubstituted, 3- to 7-membered, monocyclic carbocyclyl). In certain embodiments, $W^6$ and $W^7$ are joined to form substituted or unsubstituted cyclopropyl, substituted or unsubstituted cyclobutyl, substituted or unsubstituted cyclopentyl, or substituted or unsubstituted cyclohexyl. In certain embodiments, $W^6$ and $W^7$ are joined to form substituted or unsubstituted heterocyclyl (e.g., substituted or unsubstituted, 3- to 7-membered, monocyclic heterocyclyl, wherein one, two, or three atoms in the heterocyclic ring system are independently nitrogen, oxygen, or sulfur). In certain embodiments, $W^6$ and $W^7$ are joined to form substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $W^6$ and $W^7$ are joined to form substituted or unsubstituted aryl (e.g., substituted or unsubstituted phenyl). In certain embodiments, $W^6$ and $W^7$ are joined to form substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen).

In certain embodiments, $W^7$ is H. In certain embodiments, $W^7$ is halogen (e.g., F, Cl, Br, or I). In certain embodiments, $W^7$ is substituted or unsubstituted $C_{1-6}$ alkyl (e.g., Me). In certain embodiments, $W^7$ is —$OR^d$ (e.g., —OH or —OMe).

When two instances of $W^8$ are present in a compound described herein, the two instances of $W^8$ may be the same or different from each other. In certain embodiments, at least one instance of $W^8$ is halogen (e.g., F, Cl, Br, or I). In certain embodiments, at least one instance of $W^8$ is substituted or unsubstituted $C_{1-6}$ alkyl (e.g., Me). In certain embodiments, at least one instance of $W^8$ is —$OR^d$ (e.g., —OH or —OMe).

In certain embodiments, r is 0. In certain embodiments, r is 1. In certain embodiments, r is 2.

In certain embodiments, L is —O—; m is 0; $W^2$ is H; and each instance of $W^3$ is H.

In certain embodiments, k is 0; n is 0; m is 0; W is H; and each instance of $W^3$ is H.

In certain embodiments, k is 0; L is —O—; n is 0; m is 0; $W^2$ is H; and each instance of $W^3$ is H.

In certain embodiments, k is 0; L is —O—; n is 0; $X^1$ is CH; m is 0; $W^2$ is H; and each instance of $W^3$ is H.

In certain embodiments, k is 0; L is —O—; n is 0; $X^1$ is N; m is 0; $W^2$ is H; and each instance of $W^3$ is H.

In certain embodiments, the compound of Formula (I) is of the formula:

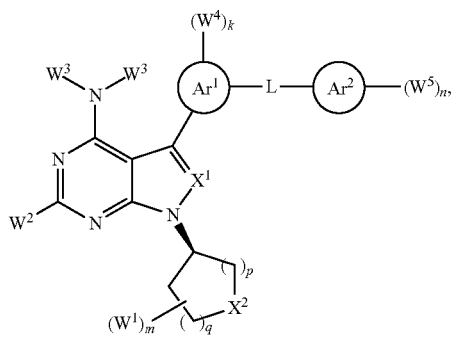

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

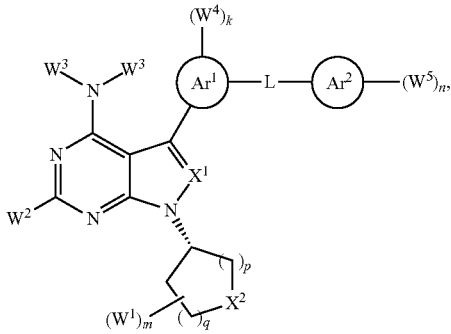

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

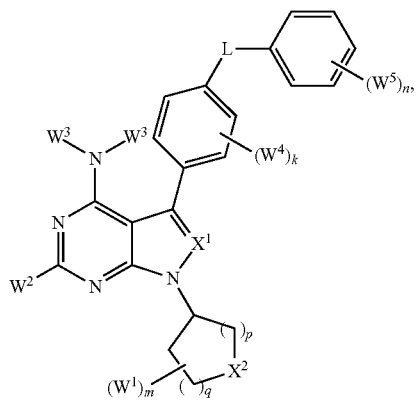

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

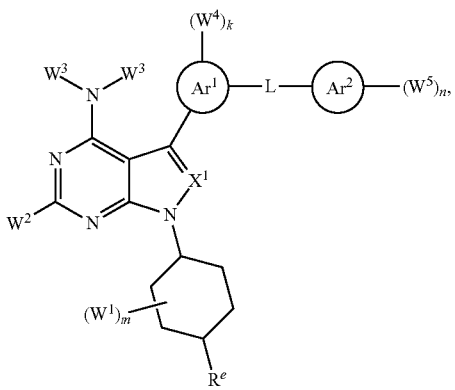

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

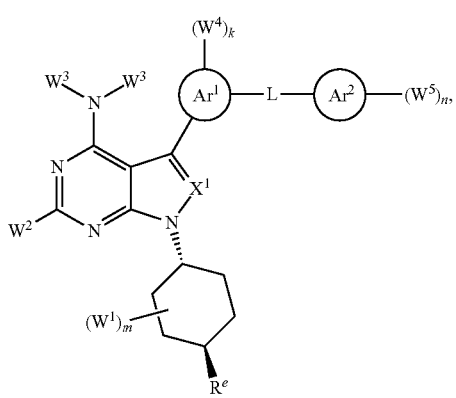

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

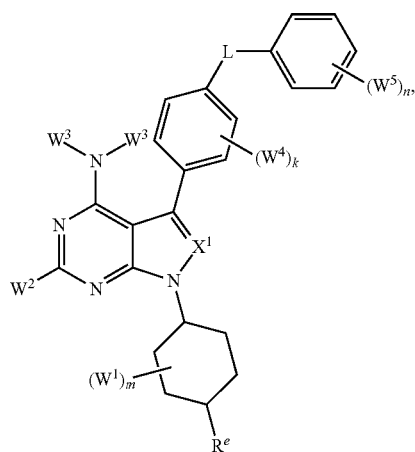

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

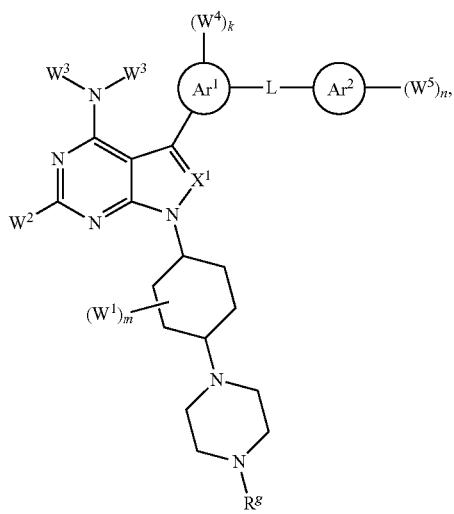

or a pharmaceutically acceptable salt, solvate, hydrate, polymorph, co-crystal, tautomer, stereoisomer, isotopically labeled derivative, or prodrug thereof, wherein $R^g$ is H, substituted or unsubstituted $C_{1-6}$ alkyl, or a nitrogen protecting group. In certain embodiments, $R^g$ is H. In certain embodiments, $R^g$ is substituted or unsubstituted $C_{1-6}$ alkyl. In certain embodiments, $R^g$ is Me. In certain embodiments, $R^g$ is substituted methyl, Et, substituted ethyl, Pr, substituted propyl, Bu, or substituted butyl. In certain embodiments, $R^g$ is a nitrogen protecting group (e.g., Bn, Boc, Cbz, Fmoc, trifluoroacetyl, triphenylmethyl, acetyl, or Ts).

In certain embodiments, the compound of Formula (I) is of the formula:

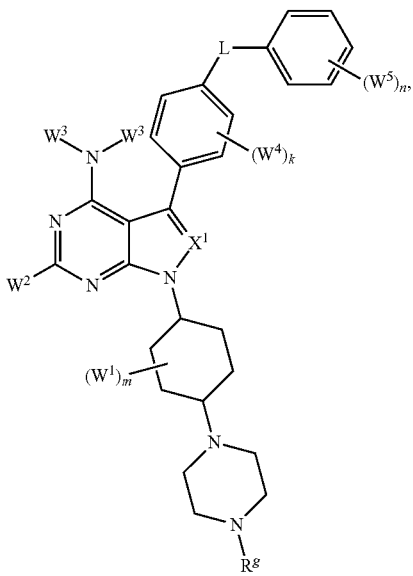

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

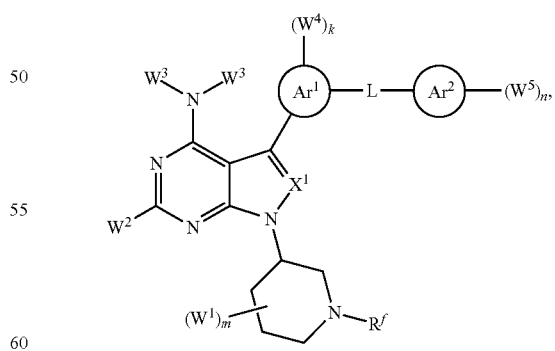

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

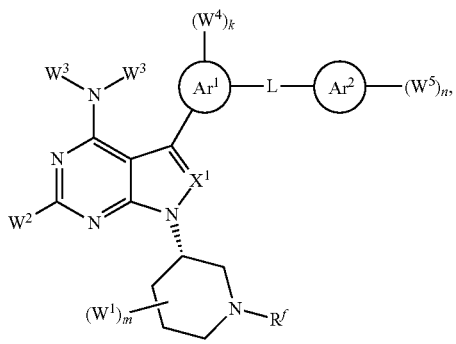

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

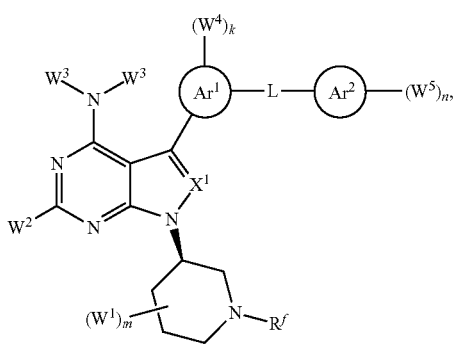

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

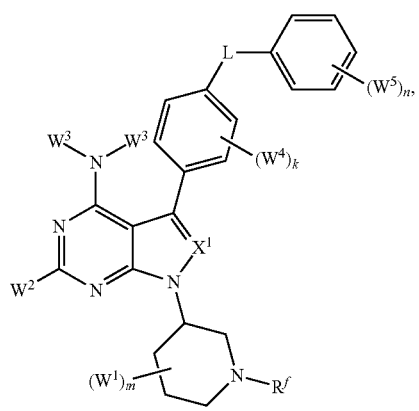

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

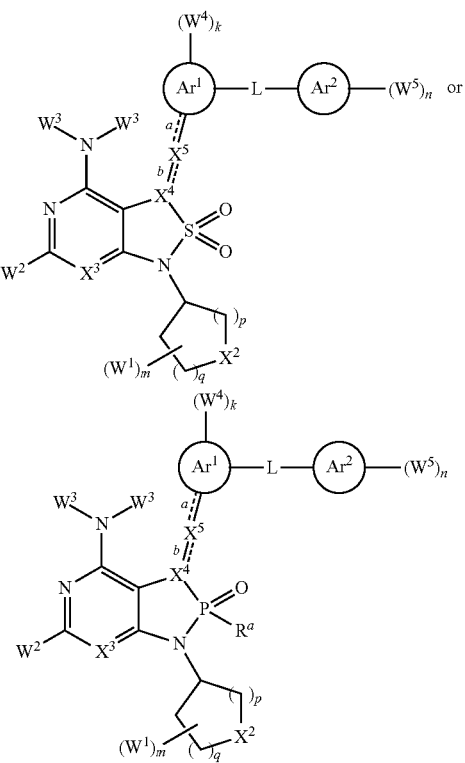

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

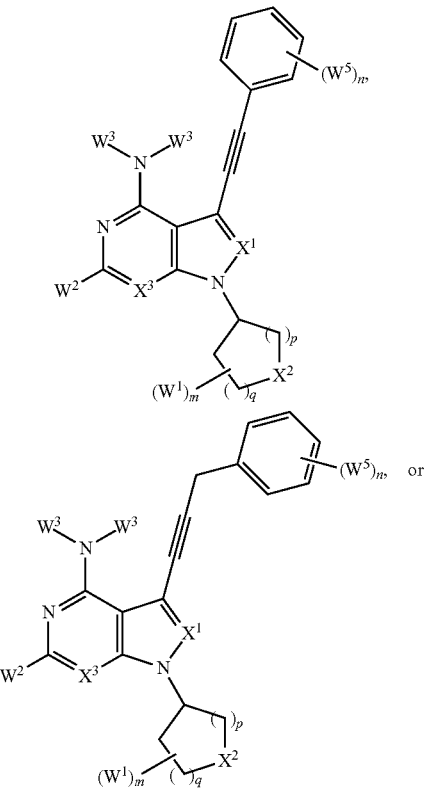

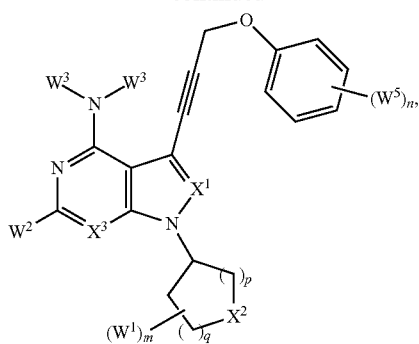

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

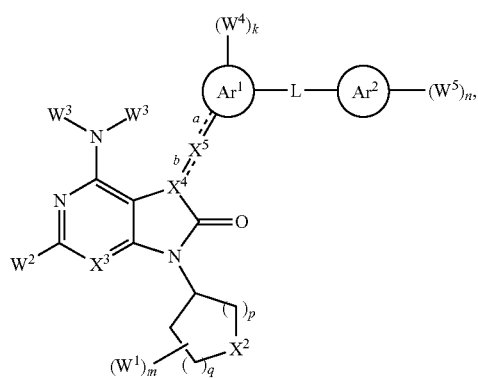

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

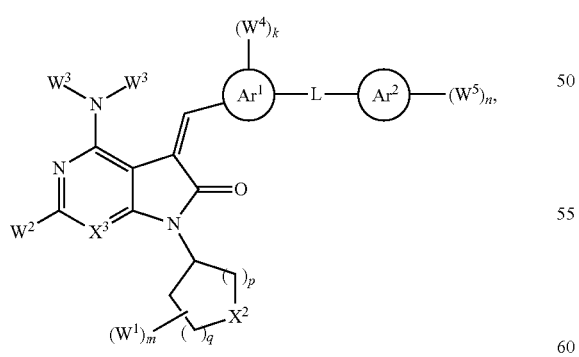

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

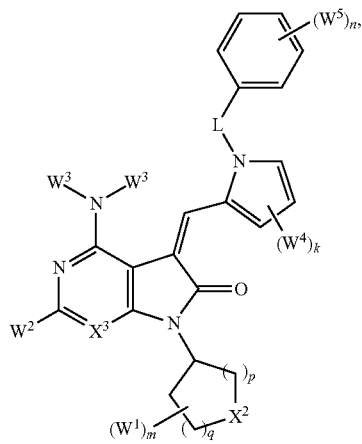

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

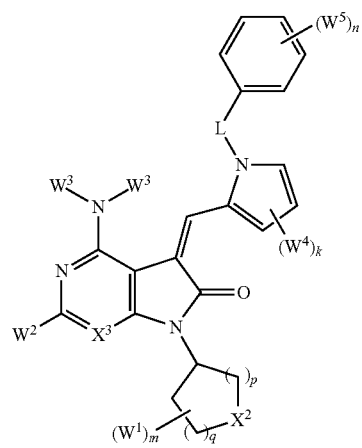

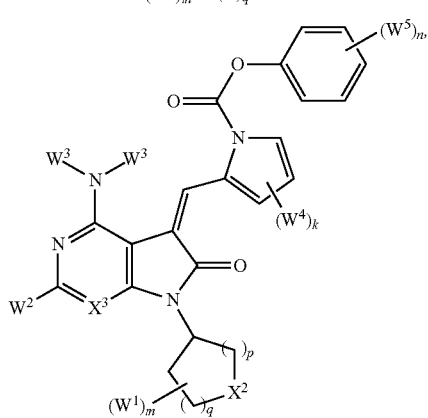

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

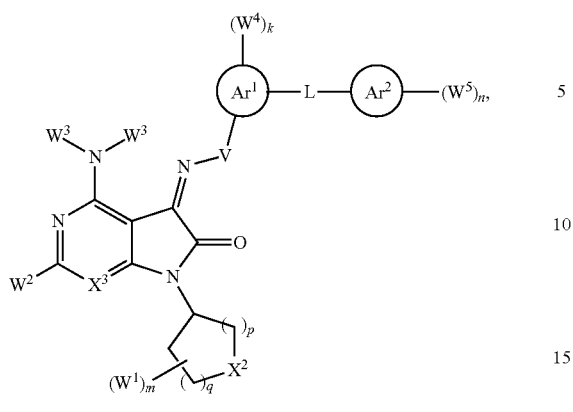

or a pharmaceutically acceptable salt, solvate, hydrate, polymorph, co-crystal, tautomer, stereoisomer, isotopically labeled derivative, or prodrug thereof, wherein V is absent, —C(R$^c$)$_2$—, —C(=O)—, —O—, or —N(R$^b$)—.

In certain embodiments, the compound of Formula (I) is of the formula:

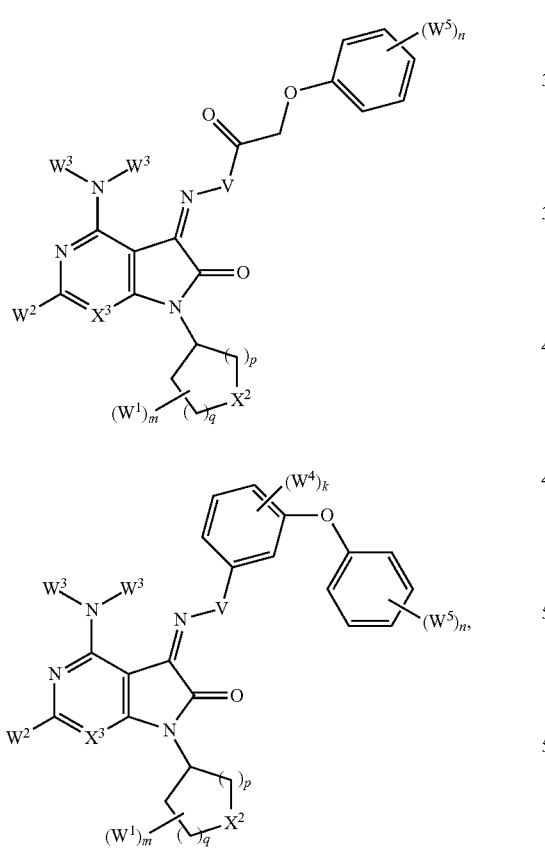

or a pharmaceutically acceptable salt, solvate, hydrate, polymorph, co-crystal, tautomer, stereoisomer, isotopically labeled derivative, or prodrug thereof, wherein V is absent, —C(R$^c$)$_2$—, —C(=O)—, —O—, or —N(R$^b$)—.

In certain embodiments, the compound of Formula (I) is of the formula:

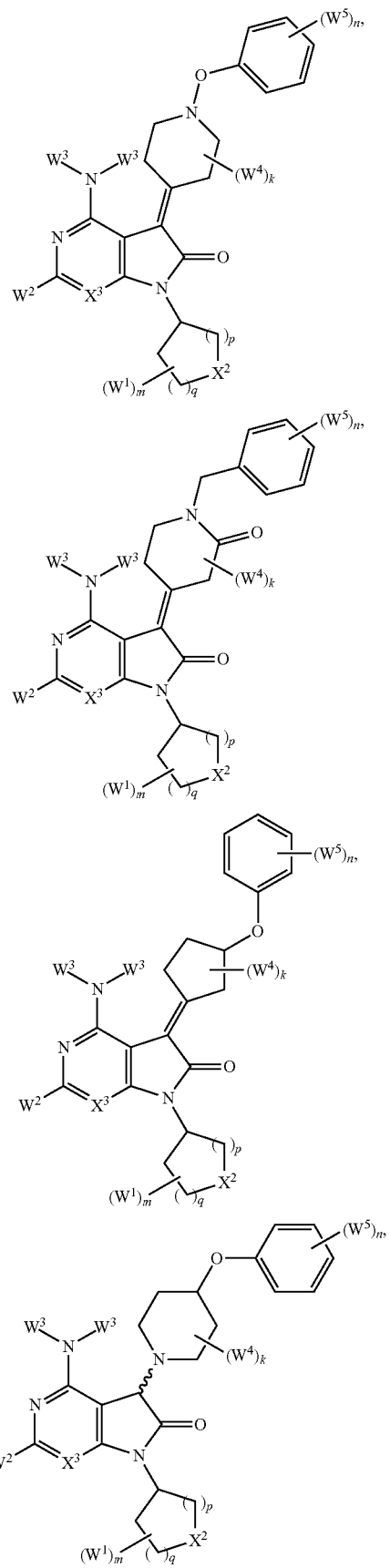

-continued

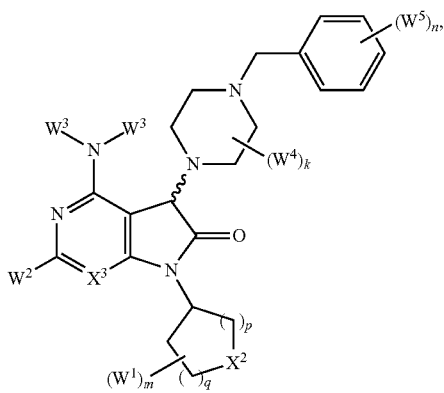

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

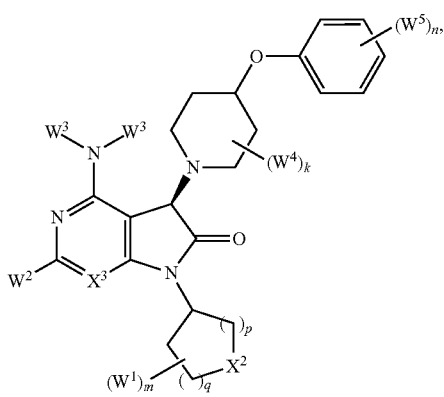

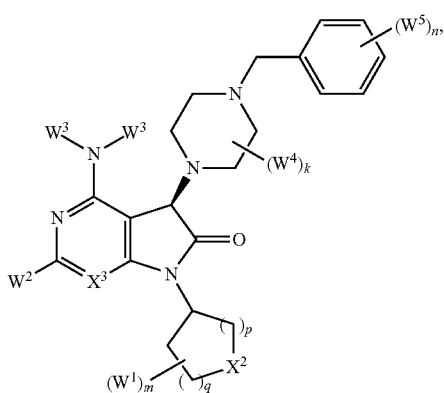

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

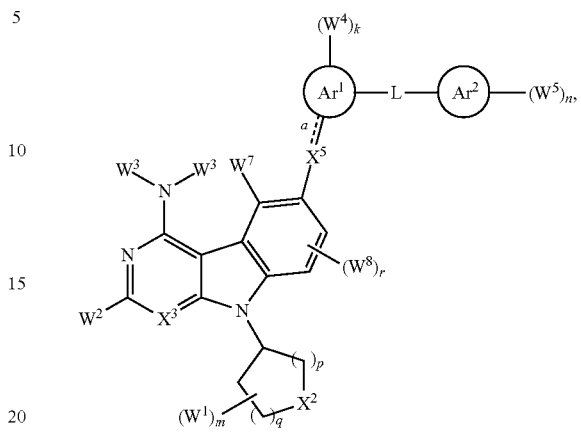

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

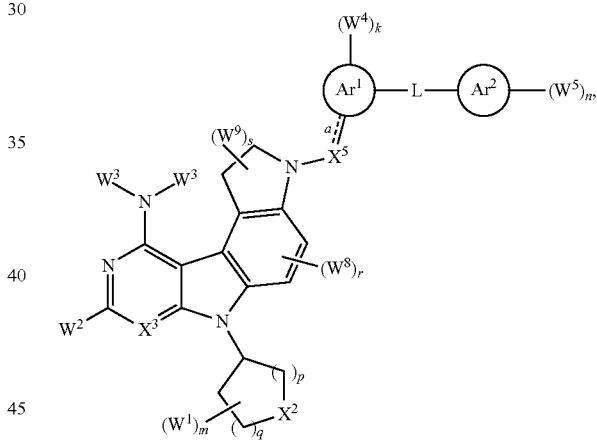

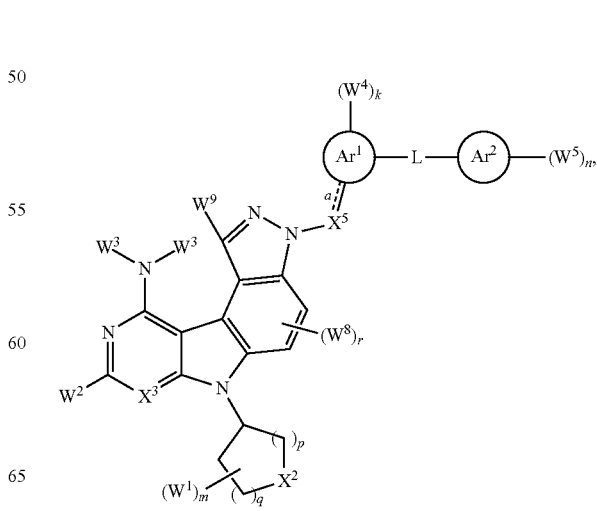

-continued

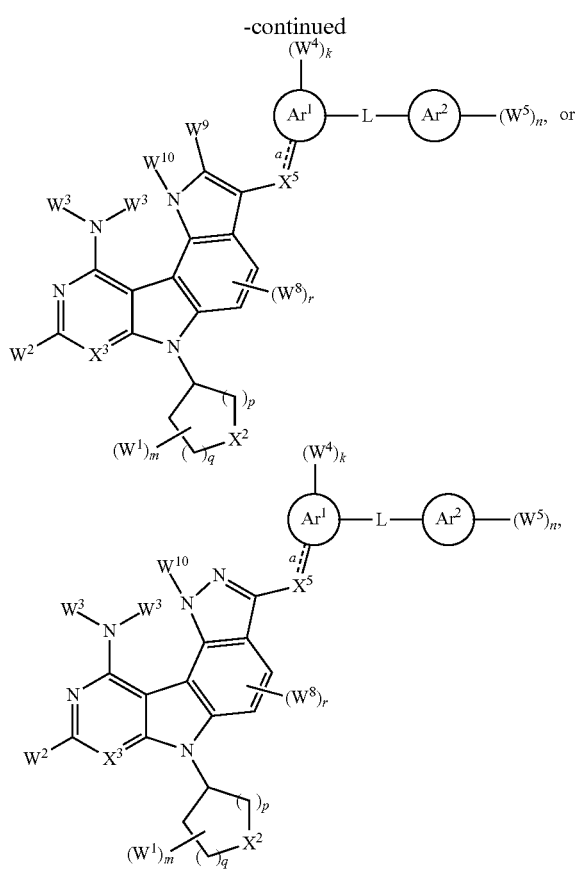

or a pharmaceutically acceptable salt, solvate, hydrate, polymorph, co-crystal, tautomer, stereoisomer, isotopically labeled derivative, or prodrug thereof, wherein:

each instance of W9 is independently halogen, substituted or unsubstituted $C_{1-6}$ alkyl, or —$OR^d$;

s is 0, 1, 2, 3, or 4; and $W^{10}$ is hydrogen, substituted or unsubstituted $C_{1-6}$ alkyl, or a nitrogen protecting group. Exemplary compounds of Formula (I) include, but are not limited to:

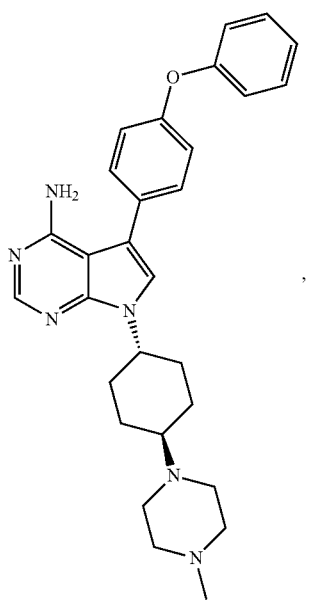

1 and pharmaceutically acceptable salts, solvates, hydrates, polymorphs, co-crystals, tautomers, stereoisomers, isotopically labeled derivatives, and prodrugs thereof.

In certain embodiments, the exemplary compound of Formula (I) is A419259 (trihydrochloride of compound 1), or a solvate, hydrate, polymorph, co-crystal, tautomer, stereoisomer, isotopically labeled derivative, or prodrug thereof.

Exemplary compounds of Formula (I) further include, but are not limited to:

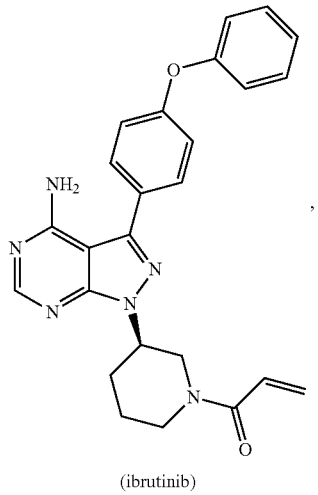 [SMILES: C=CC(=O)N1CCC[C@@H](n2nc(-c3ccc(Oc4ccccc4)cc3)c3c(N)ncnc32)C1]

(ibrutinib)

and pharmaceutically acceptable salts, solvates, hydrates, polymorphs, co-crystals, tautomers, stereoisomers, isotopically labeled derivatives, and prodrugs thereof.

In certain embodiments, a compound of Formula (I) is not ibrutinib, or a pharmaceutically acceptable salt thereof.

In certain embodiments, a compound of Formula (I), or a pharmaceutically acceptable salt, solvate, hydrate, polymorph, co-crystal, tautomer, stereoisomer, isotopically labeled derivative, or prodrug thereof (e.g., a compound of Formula (I), or a pharmaceutically acceptable salt thereof) is a selective HCK inhibitor.

In certain embodiments, a compound of Formula (II), or a pharmaceutically acceptable salt, solvate, hydrate, polymorph, co-crystal, tautomer, stereoisomer, isotopically labeled derivative, or prodrug thereof (e.g., a compound of Formula (II), or a pharmaceutically acceptable salt thereof) is a selective HCK inhibitor.

The present invention is further illustrated by the following Example, which in no way should be construed as further limiting. The entire contents of all of the references (including literature references, issued patents, published patent applications, and co pending patent applications) cited throughout this application are hereby expressly incorporated by reference.

EXAMPLES

Example 1

Materials and Methods
Primary Cells and Cell Lines

Primary WM cells (CD19+) were isolated from bone marrow (BM) aspirates, and peripheral blood mononuclear cells (PBMC) were collected from healthy donors (HD) after informed written consent. Primary WM lymphoplasmacytic cells (LPC) and cell lines were genotyped for MYD88 mutations as previously described.[2,4] MYD88$^{L265P}$ BCWM.1 and MWCL-1 WM cells; TMD-8, HBL-1, and OCI-Ly3 and MYD88$^{S222R}$ SU-DHL2 DLBCL cells; and MYD88 wild-type (MYD88$^{WT}$) OCI-Ly7 and OCI-Ly19 DLBCL cells; Ramos Burkitt's cells; and RPMI-8226 and MM.1S myeloma cells were used.

Lentiviral Transduction Experiments

MYD88$^{WT}$ or MYD88$^{L265P}$ proteins were over-expressed in BCWM.1 and MWCL-1 cells following lentiviral transduction as previously described.[7] The over-expression of proteins coding for wild-type HCK (HCK$^{WT}$) or HCK harboring a mutated gatekeeper residue (HCK$^{T333M}$) at amino acid position 333 (338 based on c-SRC numbering)[16] was accomplished by lentiviral transduction of HCK$^{WT}$ or HCK$^{T333M}$ (r. 1235C>T in NM_002110.3) sequences in a pLVX-EF1α-IRES-Puro vector (Clontech Laboratories, Mountain View Calif.). Knockdown of HCK or IL6ST (GP130) was performed using an inducible the lentiviral shRNA expression vector pLKO-Tet-On containing a tetracycline regulated expression cassette (Addgene, Cambridge Mass.). Following lentiviral transduction of BCWM.1 and MWCL-1 cells, stable cell lines were selected with 0.5~1.0 µg/ml puromycin in tetracycline-free medium. For the induced knockdown of HCK or IL6ST, tetracycline (0.8 µg/ml) was added to culture media. For HCK knockdown, lentiviral vectors were designed to target 5'-GCTGT-GATTTGGAAGGGAA-3' (HCK shRNA1; SEQ ID NO: 1) and 5'-GGATAGCGAGACCACTAAA-3' (HCK shRNA2; SEQ ID NO: 2). IL6ST knockdown targeted 5'-GGAG-CAATATACTATCATA-3' (IL6ST shRNA1; SEQ ID NO: 3) and 5'-GGAACTGTCTAGTATCTTA-3' (IL6ST shRNA2; SEQ ID NO: 4). A scrambled shRNA vector was used for control purposes.

Cell Viability Assessments

Apoptosis analysis was performed using Annexin V/Propidium iodide staining with the Apoptosis Detection Kit I (BD Pharmingen, San Jose Calif.). Cells (1×10$^6$/well) were treated in 24 well plates for 18 hours with inhibitors or corresponding controls. A minimum of 10,000 events were acquired using a BD™ FACSCanto II flow cytometer, and analyzed with BD FACS DIVA Software. For WM patient cells, BMMC (2×10$^6$/well) were treated with inhibitors, and CD19-APC-cy7 antibody (BD Pharmingen) was used with Annexin V antibody to analyze WM cell apoptosis. Alamar-Blue® cell viability assay (Life Technologies, Carlsbad Calif.) was used to assess cell death following inducible HCK knockdown. For these experiments, transduced cells (1×10$^5$/ml) were cultured with tetracycline, and aliquoted every other day on days 1-11. AlamarBlue® solution (¹⁄₁₀ total volume) was added to cells and incubated for 2 hours. Aliquoted plates were read in a SpectraMax M3 plate reader (Molecular Devices, Sunnyvale, Calif.). Relative cell survival was calculated as percentage of fluorescence relative to scrambled control. The CellTiter-Glo® Luminescent cell viability assay (Promega, Madison Wis.) was used to assess the dose-response of inhibitors. Cells were seeded into 384 well plates with the EL406 Combination Washer Dispenser (BioTek Instruments, Inc.) and inhibitors injected into the cells culture media with the JANUS Automated Workstation (PerkinElmer Inc., Waltham Mass.). Cells were treated with serial diluted inhibitors (20-0.0006 M) for 72 hours at 37° C. Luminescent measurement was performed using the 2104 Envision® Multilabel Reader (PerkinElmer Inc.).

RT-PCR and Quantitative-PCR

Total RNA were isolated using AllPrep DNA/RNA Mini Kit (QIAGEN), and cDNA synthesized by SuperScript® III First-Strand Synthesis SuperMix (Life Technologies). Quantitative detection of mRNA levels for HCK, IL6 and IL6R was performed using TaqMan® Gene Expression Assays with TaqMan® Gene Expression Master Mix per manufacturer's instructions using the ABI Prism 7500 Sequence Detection System (Applied Biosystems).

PhosFlow Analysis

PhosFlow analysis was performed to delineate HCK phosphorylation. Cells were fixed with BD PhosFlow Fix Buffer I at 37° C. for 10 min. Cells were then centrifuged (300×g for 5 min) and washed twice with PhosFlow Perm/Wash Buffer I (BD Pharmingen). Cells were then stained with HCK (pTyr$^{411}$) antibody (Abcam, Cambridge Mass.) alone (for cell lines) or with anti-CD20-APC-Cy7 (BD Pharmingen) for primary WM cells. Following staining, cells were incubated in the dark for 30 min at room temperature, then washed thrice with BD PhosFlow Perm/Wash Buffer I, followed by anti-Rabbit IgG DyLight®-649 secondary antibody (Abcam), and incubated for an additional 20 min. Cells were then washed twice with BD PhosFlow Perm/Wash Buffer I and flow analysis performed using a BD™ FACSCanto II Flow Cytometer.

Immunoblotting

Immunoblotting was performed following gene over-expression, knockdown or kinase pulldown with biotinylated probes using antibodies for HCK, AKT-pT308, AKT, ERK1/2-pT202/pY204, ERK1/2, PLCγ1-pY783, PLCγ2-pY1217, PLCγ2, BTK-pY223, BTK, IRAK4-pT345/S346, IRAK4, SRC, LYN (Cell Signaling Technologies, Danvers Mass.), PI3K-p85β-pY464 (LifeSpan Biosciences, Seattle Wash.), PI3K-p85β, PLCγ1, IL6ST (Santa Cruz Biotechnology, Dallas Tex.) in primary WM cells, and cell lines. Staining with GAPDH antibodies was used for determination of protein loading (Santa Cruz Biotechnology).

Ibrutinib Probe Assay and Kinase Active-Site Inhibition Assay

For Ibrutinib probe assay, BCWM.1, MWCL-1 or TMD-8 cells (2×10$^7$) were treated with ibrutinib-biotin or CC-292-biotin (2 µM) for 1 hour. Cells then washed with PBS twice, and lysed with co-IP buffer (Invitrogen, Grand Island N.Y.). Two mg of protein from lysed cells was then incubated with 50 al of Pierce Streptavidin Magnetic Beads (Thermo Fisher Scientific, Cambridge Mass.) at 4° C. for 1 hour, then washed with TBST (0.1% Tween-20) thrice, and proteins eluted with SDS-PAGE sample buffer. For Kinase active-site inhibition assay, BCWM.1 cells (2×10$^7$) were pre-treated with DMSO, ibrutinib, CC-292 or A419259 (MedChem Express, Monmouth Junction N.J.) at various concentrations for 1 hour. Cells then were lysed and kinases were pulled down with ATP-biotin using Pierce™ Kinase Enrichment Kit (Thermo Fisher Scientific) per manufacturer's instructions. Kinases were eluted with SDS-PAGE sample buffer and detected by western blot.

Docking Study

The docking studies were performed using AutoDock-Tools 1.56[17], AutoDock VINA[18] and Open Babel[19] software. The lowest calculated Gibbs energy (ΔG) of the predicted binding modes indicates stronger binding affinity, and binding modes with ΔG lower than −10 kcal are highly probable to be true.

Statistical Analysis

The statistical significance of differences was analyzed using One-way ANOVA with Tukey's multiple comparisons test by Prism software. Differences were considered significant when $p<0.05$.

Results
HCK Transcription is Driven by Mutated MYD88

Figure 1B:
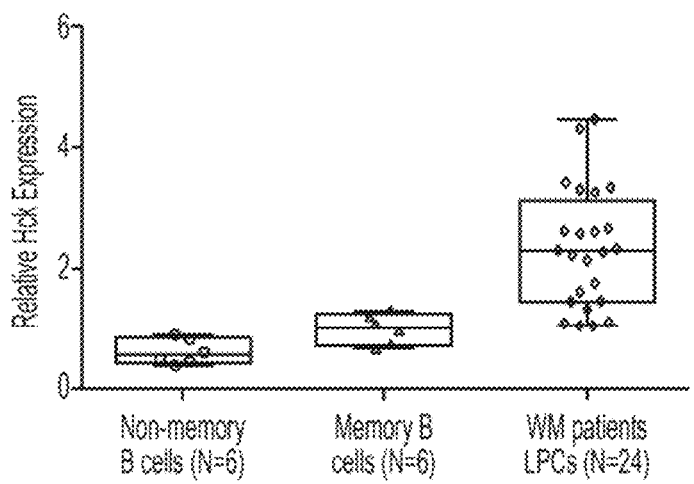
Figure 1C:
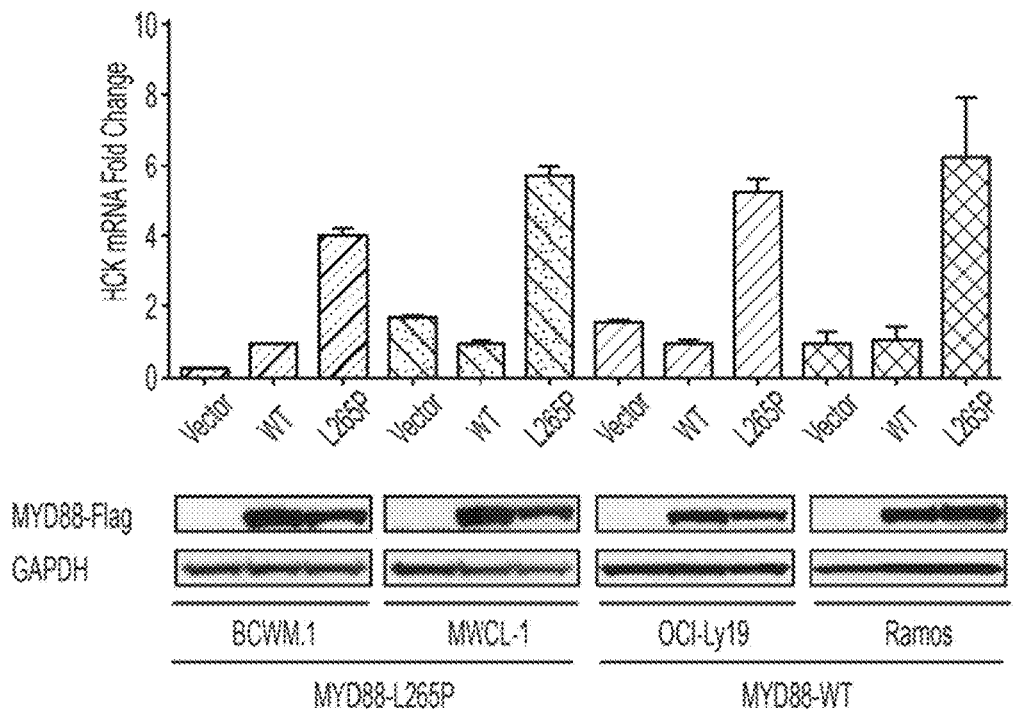

To clarify if HCK expression was aberrant in MYD88 mutated cells, we first assessed HCK transcription in MYD88 mutated WM and DLBCL cell lines by TaqMan® Gene Expression Assay. The results showed that HCK was markedly transcribed in MYD88$^{L265P}$ expressing WM (BCWM.1, MWCL-1) and DLBCL (TMD-8, HBL-1, OCI-Ly3) cells, but absent or at very low levels in MYD88$^{WT}$ (OCI-Ly7, OCI-Ly19, Ramos, MM1.S and RPMI-8226) cells by quantitative RT-PCR (FIG. 1A). Expression of the HCK transcript was also enhanced in SU-DHL2 cells that carry the MYD88$^{S222R}$ activating mutation. Western blot analysis confirmed enhanced HCK protein expression in MYD88 mutated cell lines (data not shown). We next investigated the mRNA levels of HCK in MYD88$^{L265P}$ genotyped CD19-sorted primary WM cells using a TaqMan® Gene Expression Assay. We compared HCK expression levels to both sorted healthy donor derived non-memory (CD19$^+$CD27$^+$) and memory (CD19$^+$CD27$^+$) B-cells, given that the later represent the B-cell population from where most cases of WM are likely derived.[20,21] The HCK transcript was elevated in MYD88$^{L265P}$ WM cells versus either healthy donor non-memory or memory B-cells (FIG. 1B). CXCR4 mutation status did not impact HCK Tyr$^{411}$ phosphorylation (p=0.90 for CXCR4 wild-type versus WHIM mutated patients). To clarify if mutated MYD88 was responsible for enhanced HCK expression, we over-expressed MYD88$^{L265P}$ or MYD88$^{WT}$ protein in MYD88$^{L265P}$ BCWM.1 and MWCL-1 cells, and MYD88$^{WT}$ OCI-Ly9 and Ramos cells, and assessed for differences in HCK transcription. By Western blot analysis, similar levels of exogenous MYD88 protein were detectable in MYD88$^{L265P}$ or MYD88$^{WT}$ transduced cells (FIG. 1C). The results of these studies showed significantly higher levels of HCK transcript in all four cell lines following over-expression of MYD88$^{L265P}$ versus MYD88$^{WT}$ protein (FIG. 1C).

Figure 2A:
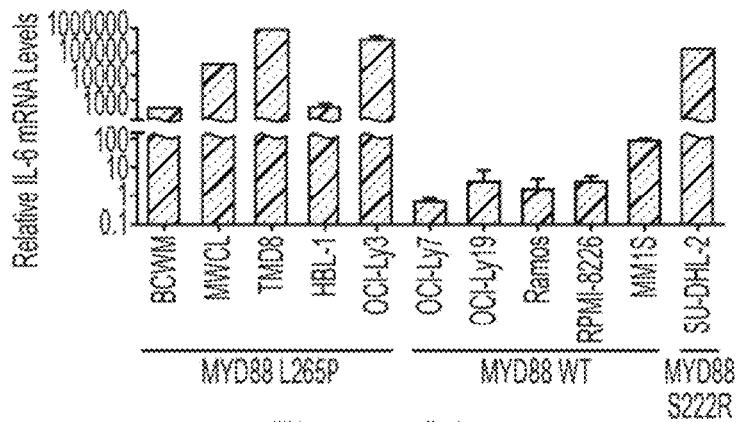
FIGS. 2A-2F show that IL6 but not IL6R transcription is induced by mutated MYD88.
Figure 2B:
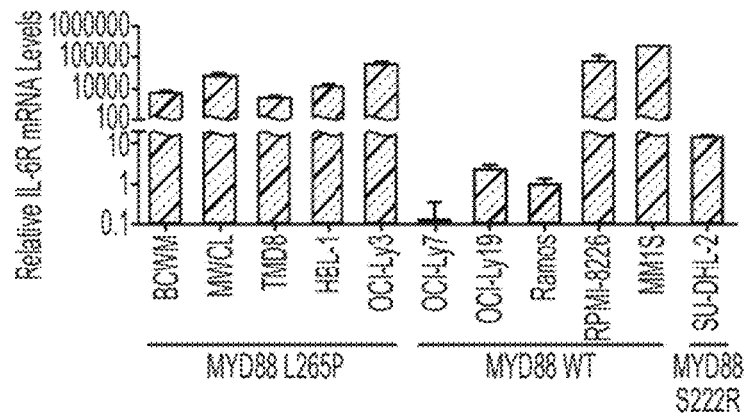
Figure 2C:
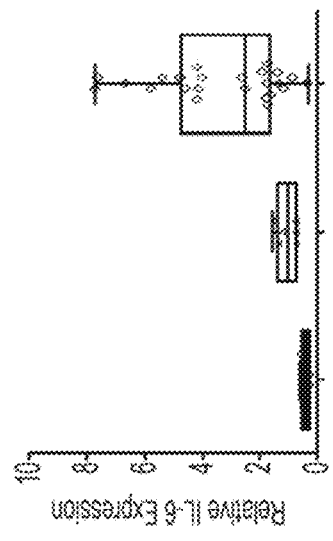
Figure 2D:
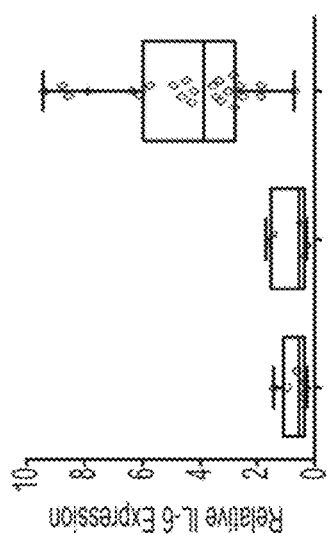
Figure 2E:
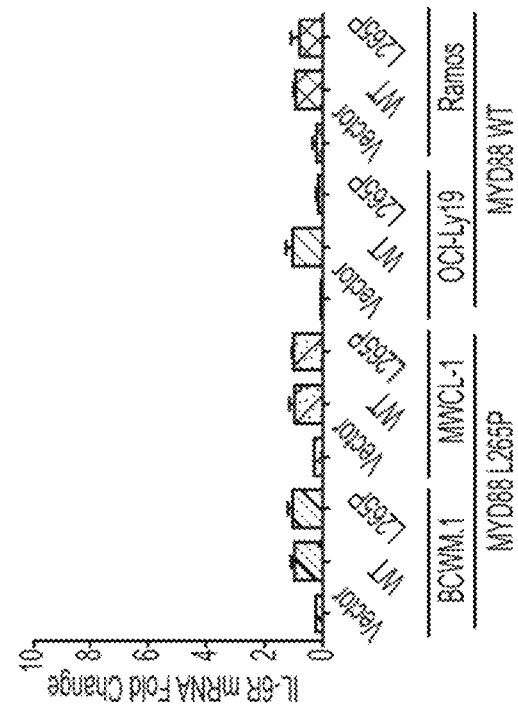
Figure 2F:
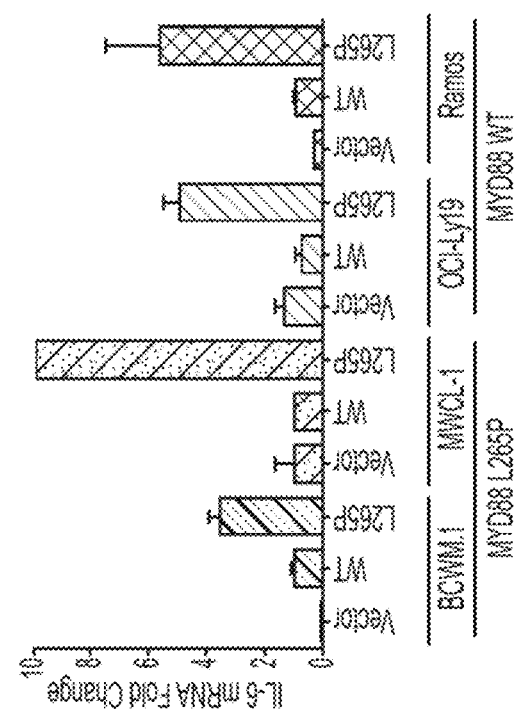

IL6 but not IL6R transcription is induced by mutated MYD88 Since previous work showed that HCK was activated by IL6 via IL6R/IL6ST, we investigated the regulatory role of mutated MYD88 on IL6 and IL6R expression.[13,14] By quantitative RT-PCR, IL6 transcription was markedly higher in MYD88$^{L265P}$ expressing WM (BCWM.1, MWCL-1) and DLBCL (TMD-8, HBL-1, OCI-Ly3), as well as MYD88$^{S122R}$ expressing SU-DHL2 cells versus MYD88$^{WT}$ (OCI-Ly7, OCI-Ly19, Ramos, MM1.S and RPMI-8226) cells (FIG. 2A). Similarly, IL6R transcription was increased in MYD88 mutated cell lines. Among MYD88$^{WT}$ malignant B-cells, IL6R transcription was low or absent, though was highly expressed in MYD88$^{WT}$ malignant plasma cells (FIG. 2B). By TaqMan® Gene Expression Assay, higher IL6 (FIG. 2C) and IL6R (FIG. 2D) transcription were found in MYD88$^{L265P}$ WM samples versus healthy donor non-memory (CD19$^+$CD27$^+$) and memory (CD19$^+$CD27$^+$) B-cells. Given these findings, we next sought to clarify if MYD88$^{L265P}$ was a driver for IL6 and IL6R transcription. Over-expression of the MYD88$^{L265P}$ protein induced marked IL6 (FIG. 2E), but not IL6R (FIG. 2F) transcription in MYD88$^{L265P}$ (BCWM.1, MWCL-1) and MYD88$^{WT}$ (OCI-Ly9 and Ramos) cells. Conversely, over-expression of MYD88$^{WT}$ protein had little or no impact on IL6 or IL6R transcription.

HCK is Hyperactive in MYD88 Mutated Cells, and its Activation is Triggered by IL6

Figure 3A:
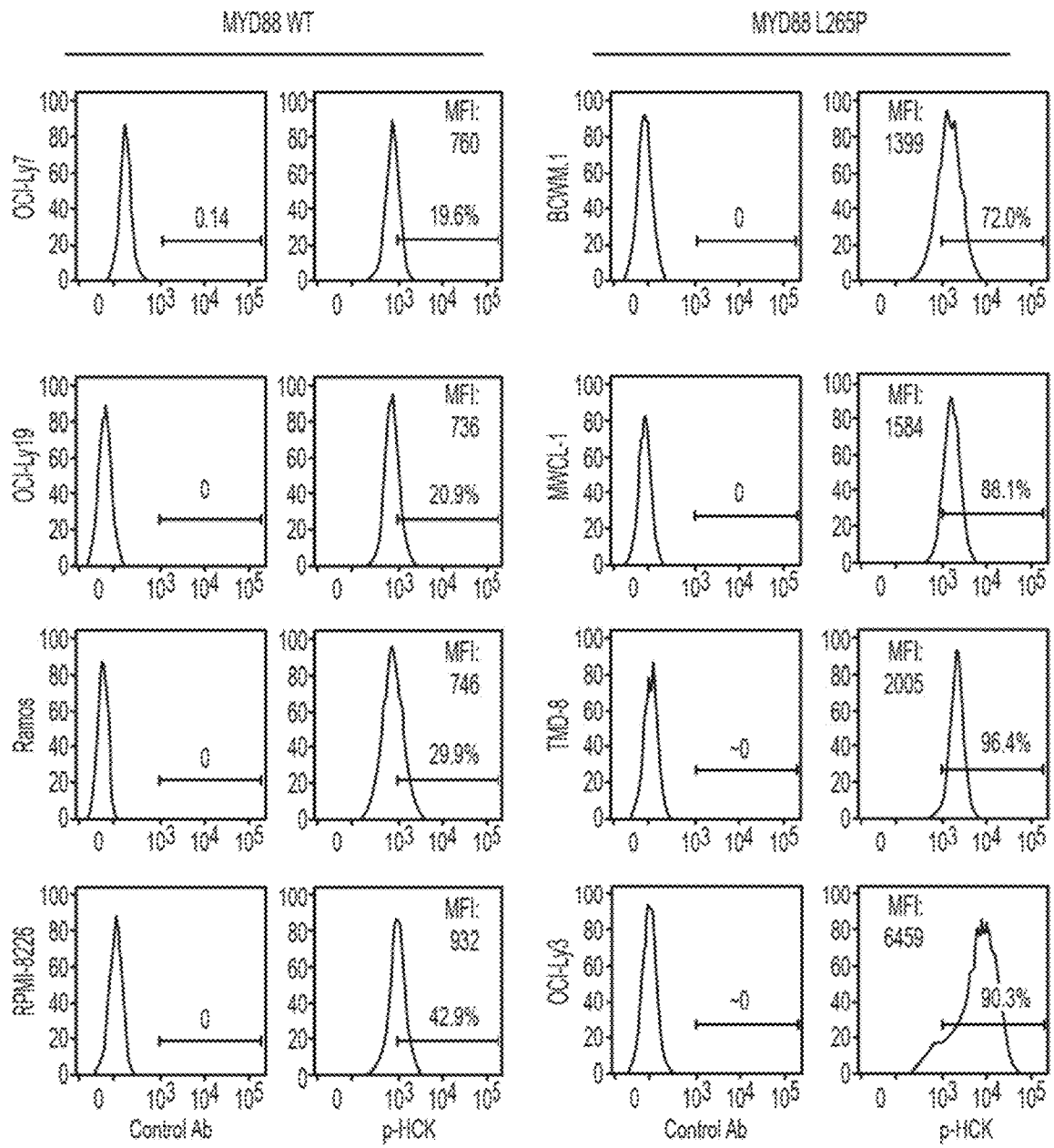
FIGS. 3A-3D show that HCK is hyperactive in MYD88 mutated cells, and its activation is triggered by IL6.
Figure 3B:
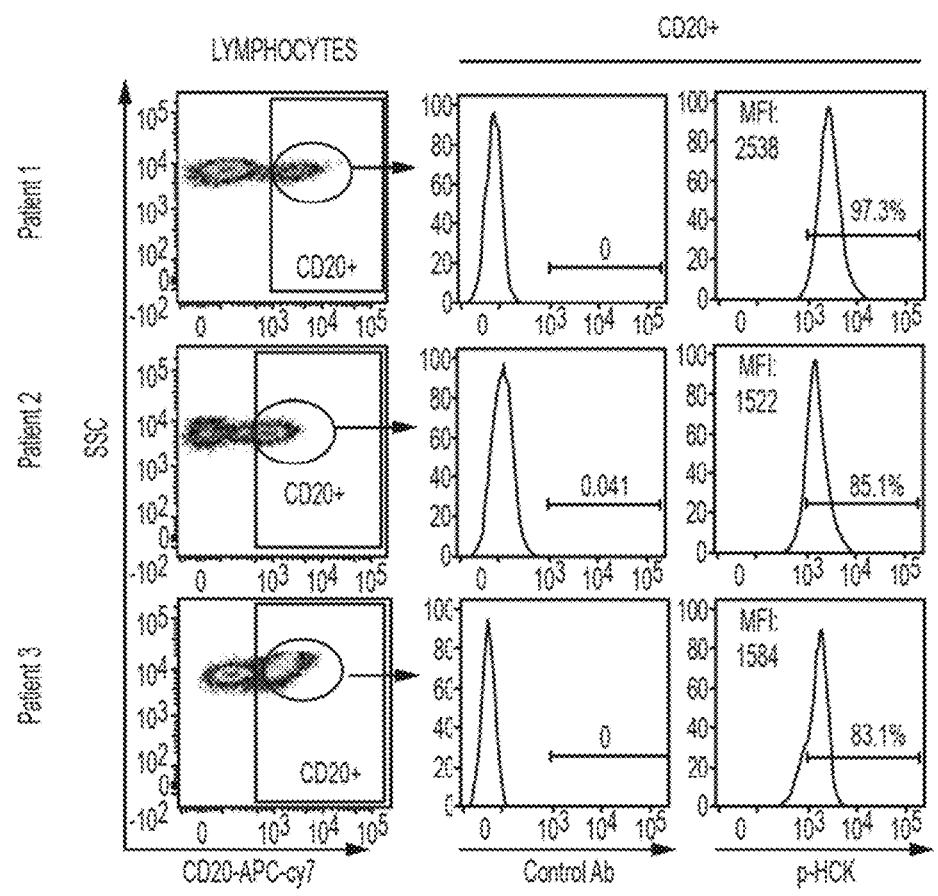
Figure 3B:
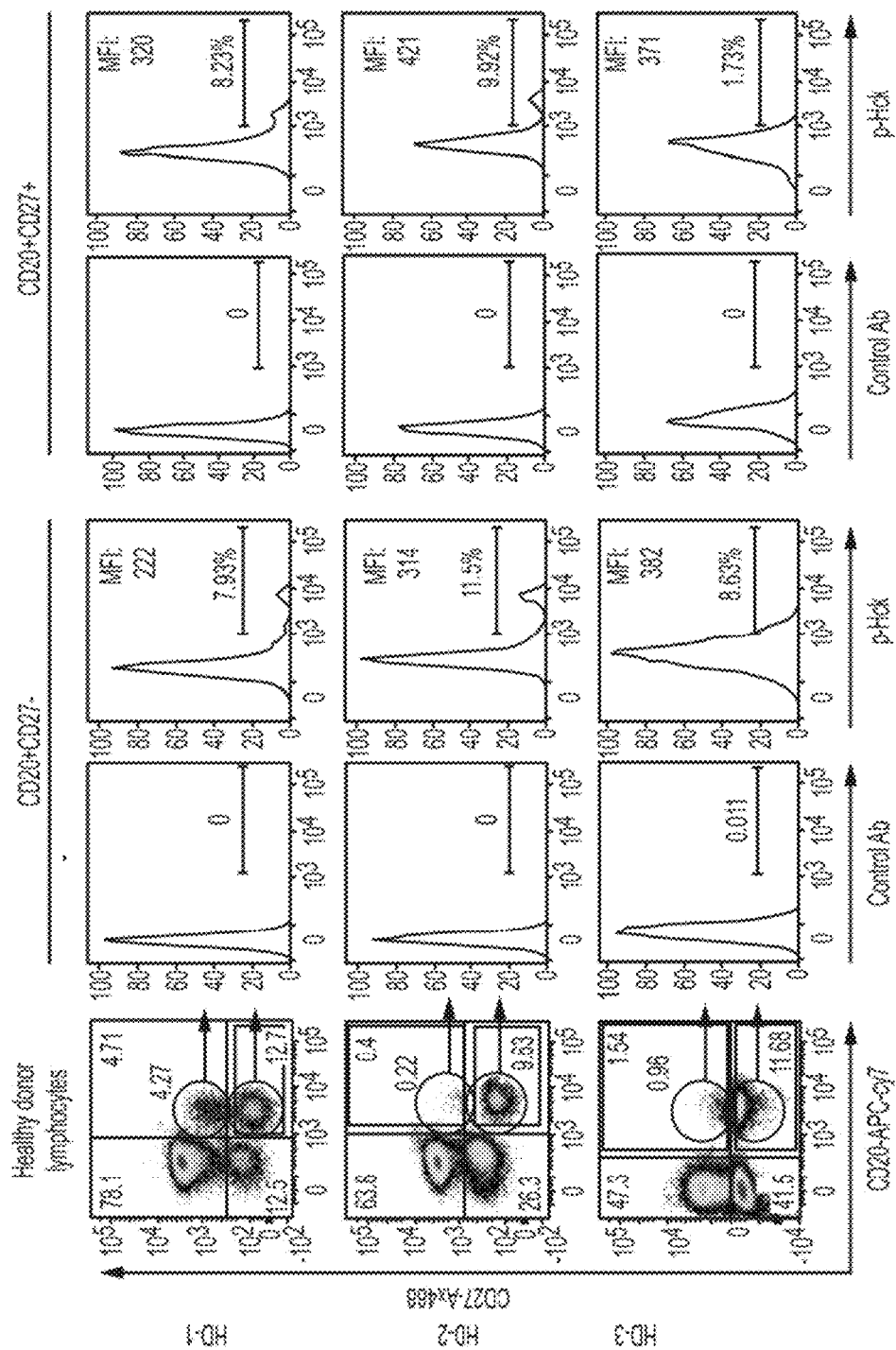
Figure 3B:
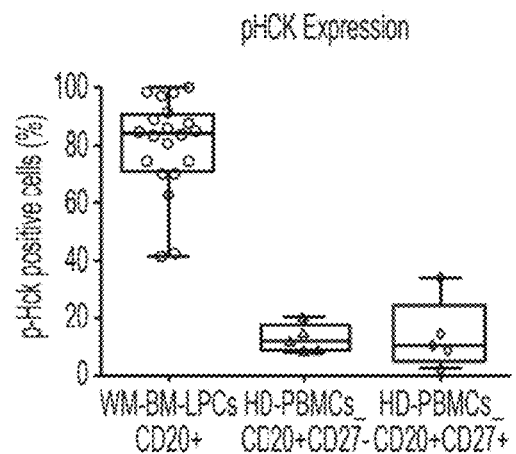
Figure 3C:
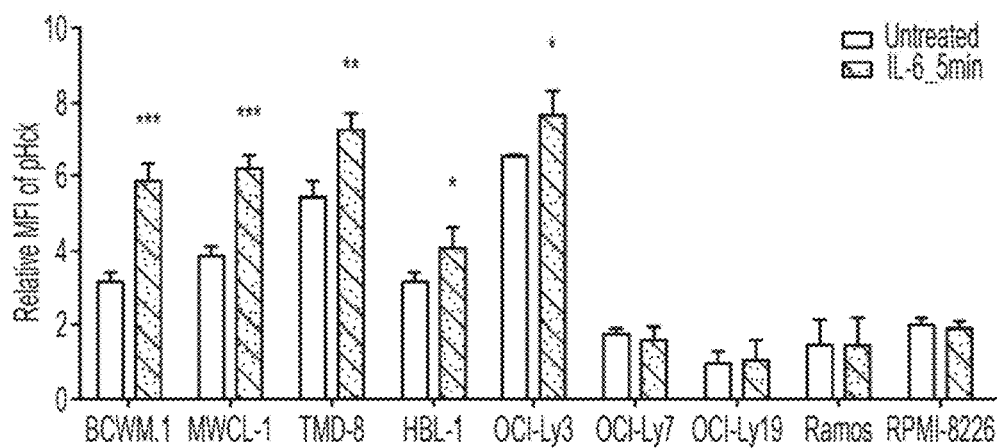
Figure 3C:
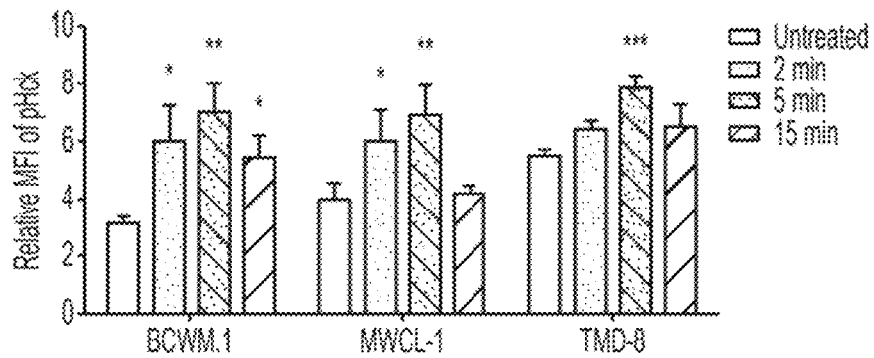
Figure 3C:
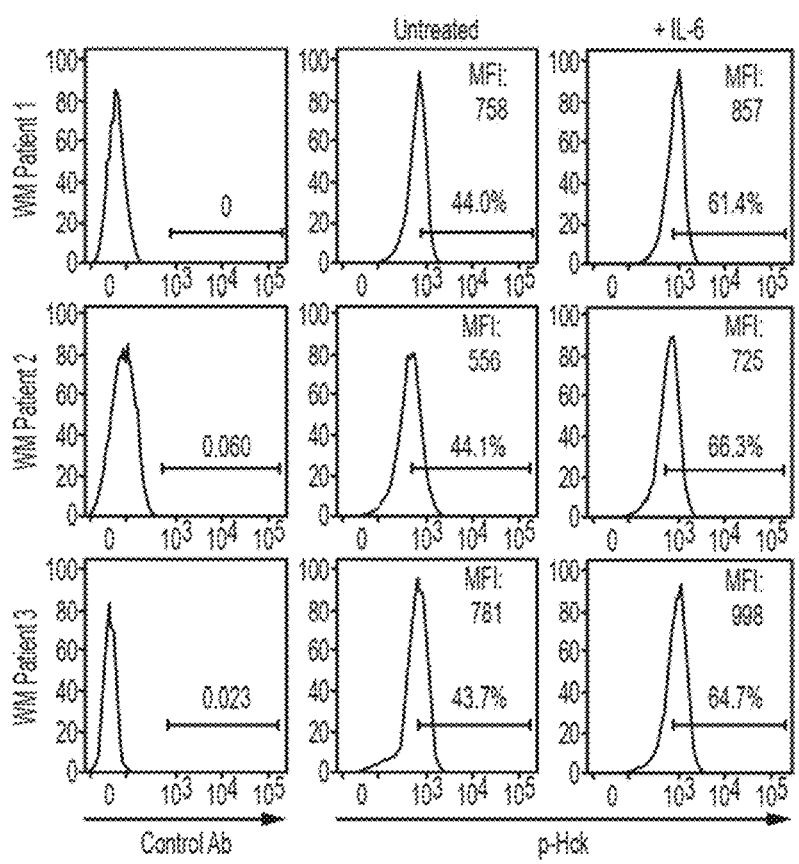
Figure 3D:
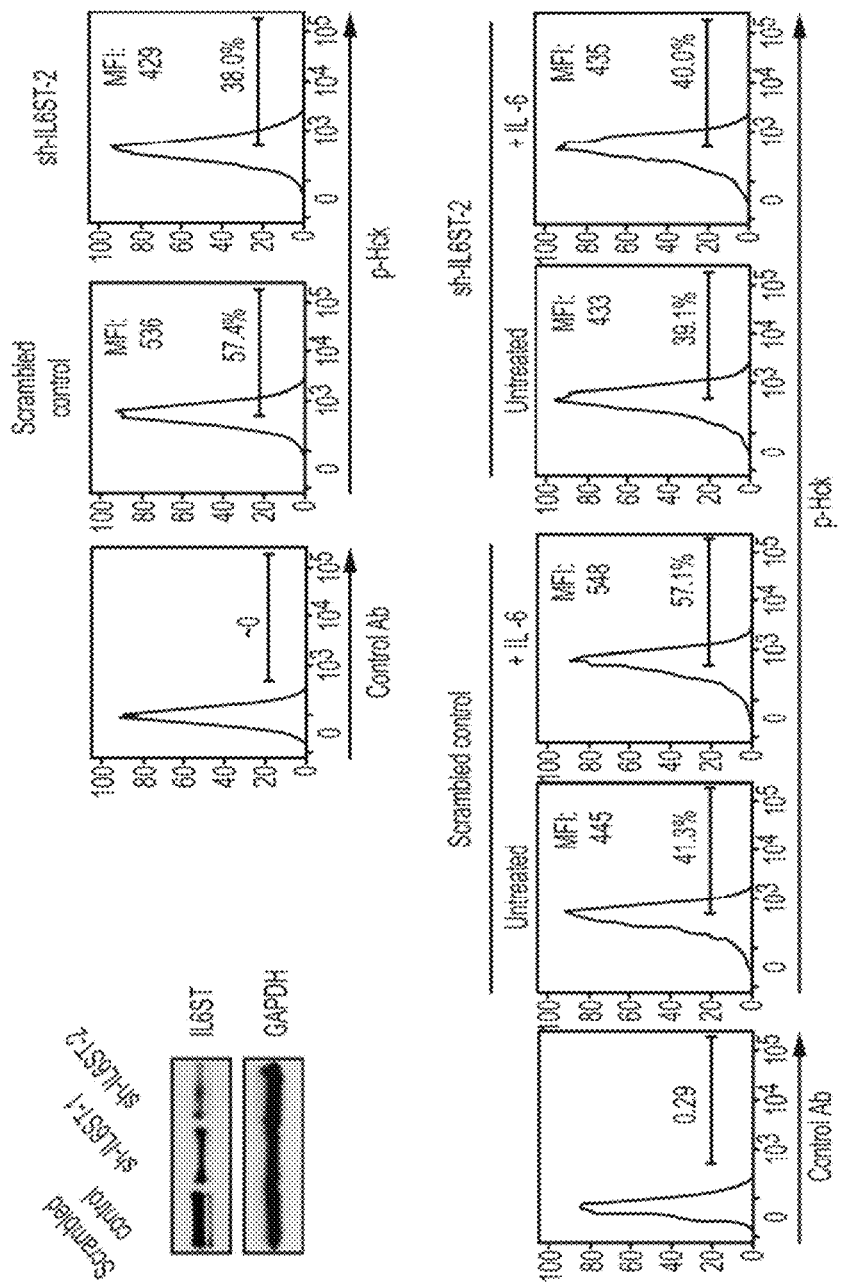

Given the above findings, we next investigated the activation state of HCK in MYD88 mutated WM and DLBCL cell lines, and primary WM cells. By PhosFlow analysis, HCK showed consistently high phosphorylation levels at the Tyr$^{411}$ activation site in mutated MYD88 versus wild-type MYD88 cells (FIG. 3A). Significantly higher levels of HCK Tyr$^{411}$ phosphorylation were also observed in primary WM patient samples versus healthy donor non-memory and memory B-cells (FIG. 3B). CXCR4 mutation status was available for 18 of 20 primary WM patient samples, and did not impact HCK Tyr$^{411}$ phosphorylation (p=0.65 for CXCR4 wild-type versus WHIM mutated patients). Treatment of mutated MYD88 WM and DLBCL cell lines and primary WM lymphoplasmacytic cells (LPCs) with IL6 augmented HCK activation, with a peak induction of Tyr$^{411}$ phosphorylation at 5 minutes following IL6 administration in mutated MYD88 cells (FIG. 3C). In contrast, little or no effect on HCK Tyr$^{411}$ phosphorylation was observed following IL6 stimulation in MYD88$^{WT}$ cells. Knockdown of IL6ST attenuated HCK activation in the presence or absence of IL6, whereas transduction with a control vector had little or no impact on HCK activation in MYD88 mutated BCWM.1 cells (FIG. 3D). Lastly, HCK transcription was not significantly altered following incubation with either IL6 (1-10 ng/mL) or an IL6 blocking antibody (1-10 μg/mL) for two hours in BCWM.1 and MWCL-1 cells using RT-PCR (data not shown).

HCK is a Determinant of Survival in MYD88 Mutated Cells

We next evaluated the impact of HCK expression on survival in MYD88 mutated BCWM.1 and MWCL-1 WM and TMD-8 and HBL-1 ABC DLBCL cells. Successful knockdown of HCK was accomplished by lentiviral transduction using inducible shRNA vectors (FIG. 4A). The results of these studies showed that knockdown of HCK in all 4 MYD88 mutated cell lines by either of two shRNA vectors resulted in sustained reduction in tumor cell viability over the 11 day evaluation period in contrast to cells transduced with a control vector (FIG. 4B).

HCK Triggers Pro-Survival Signaling in MYD88 Mutated WM Cells

Figure 5A:
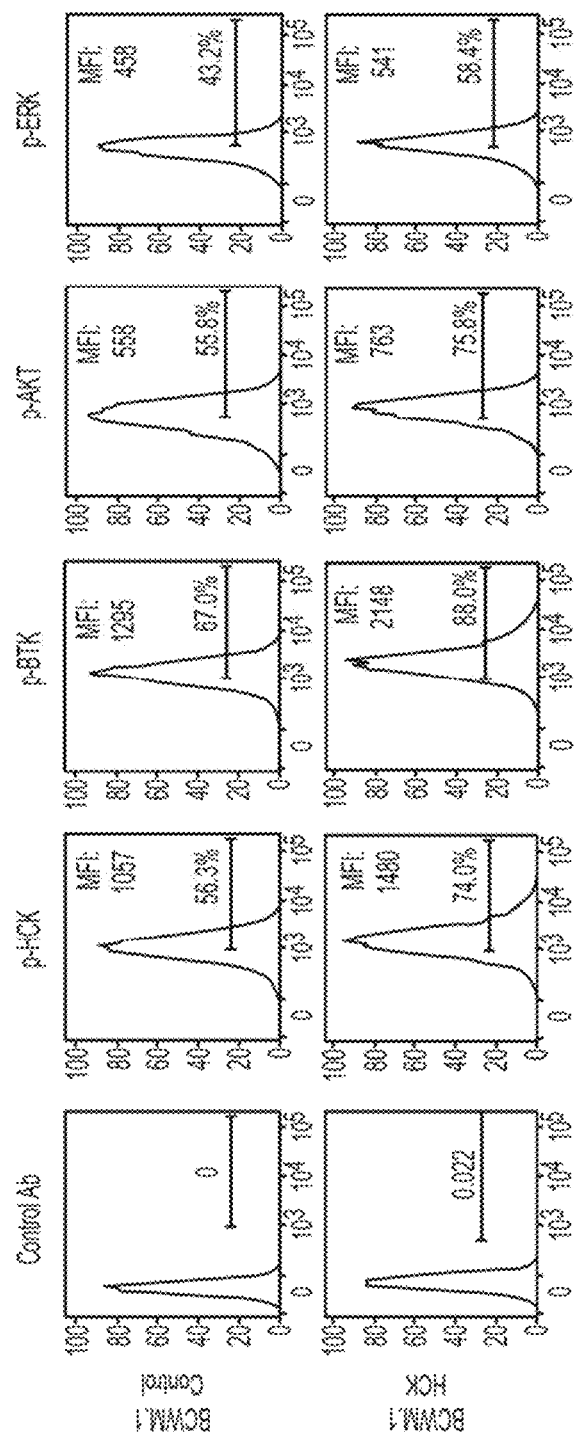
FIGS. 5A-5C show that HCK triggers pro-survival signaling in MYD88 mutated WM cells.
Figure 5A:
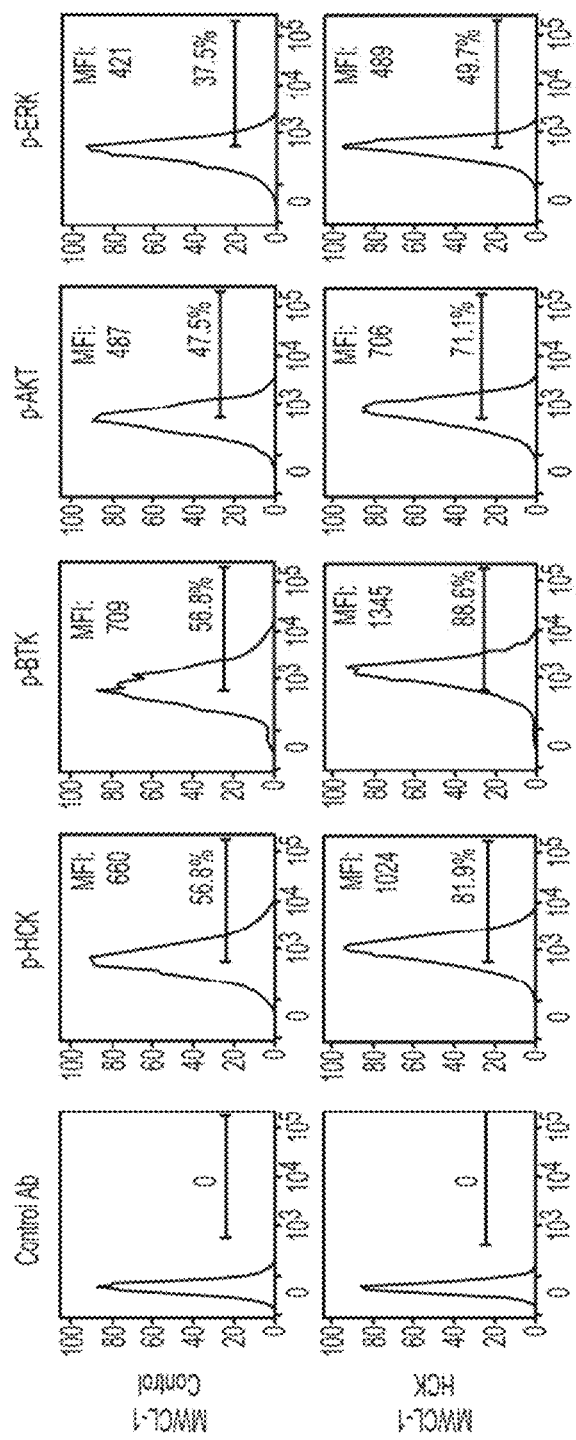
Figure 5B:
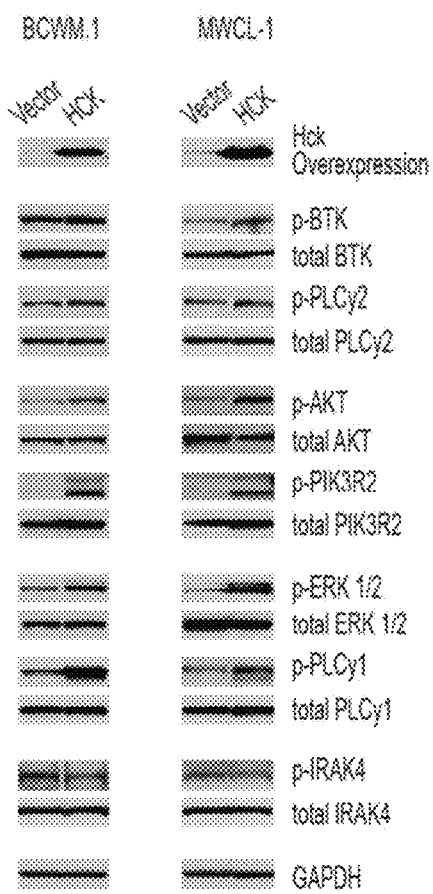
Figure 5C:
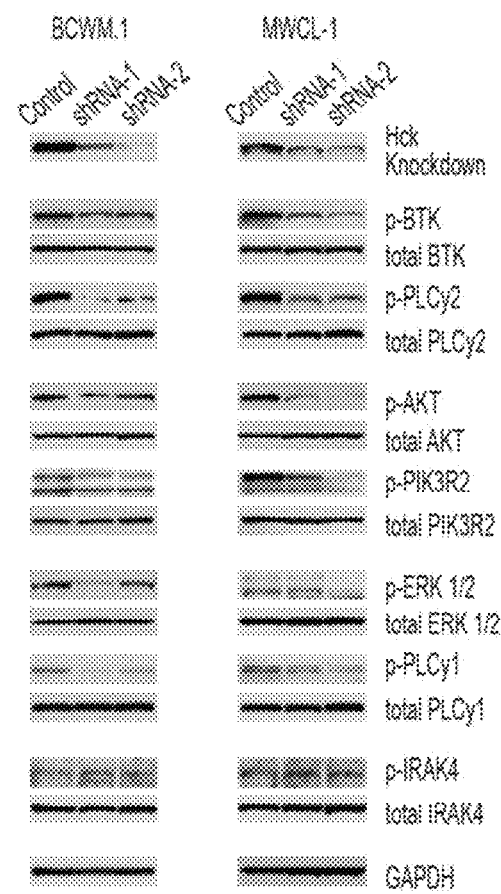

In view of the above findings, we next interrogated HCK dependent survival signaling in MYD88 mutated WM cells. We focused our efforts on PI3K/AKT, MAPK and BTK signaling pathways given their established importance in WM survival, as well as previous work implicating HCK as an upstream regulator for their signaling.[22-25] Transduction of HCK in IL6 producing BCWM.1 and MWCL-1 cells led to higher HCK protein levels by Western blot analysis and detection of activated HCK (Tyr$^{411}$) by PhosFlow analysis (FIG. 5A, 5B). Transduction of HCK in BCWM.1 and MWCL-1 cells also triggered PI3K/AKT (pPIK3R2, pAKT), MAPK (pPLCγ1, pERK1/2), and BTK (pBTK, pPLCγ2) signaling (FIG. 5B), whereas knockdown of HCK in BCWM.1 and MWCL-1 cells showed a reciprocal pattern, with diminished PI3K/AKT, MAPK and BTK signaling (FIG. 5C). IRAK4 activation was not impacted by either HCK over-expression or knockdown. Total protein levels for these signaling molecules, and GAPDH remained unchanged in these experiments.

Ibrutinib Binds to the ATP-Binding Pocket of HCK and Blocks ATP Binding

Figure 6A:
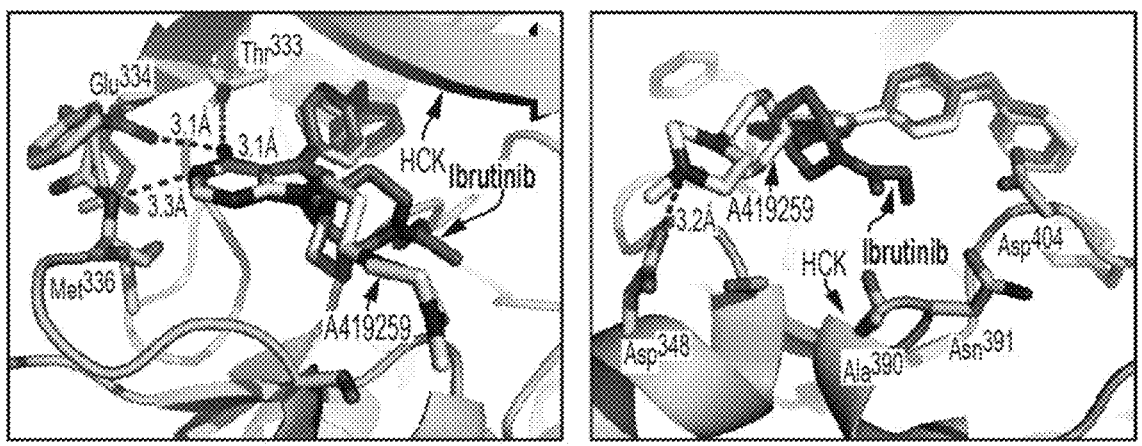
FIGS. 6A-6C show that ibrutinib binds to the ATP-binding pocket of HCK and blocks ATP binding.
Figure 6B:
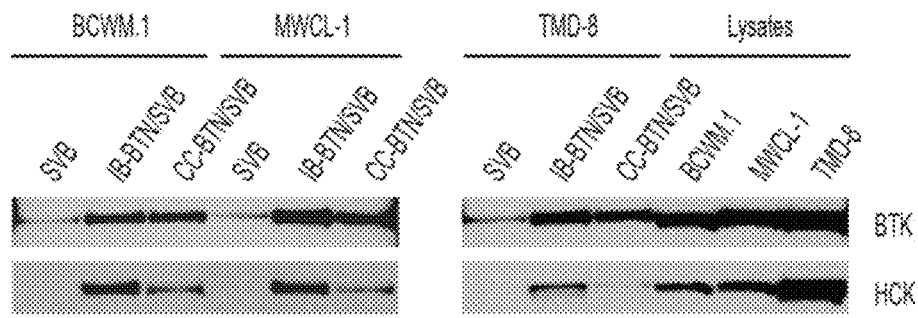
Figure 6C:
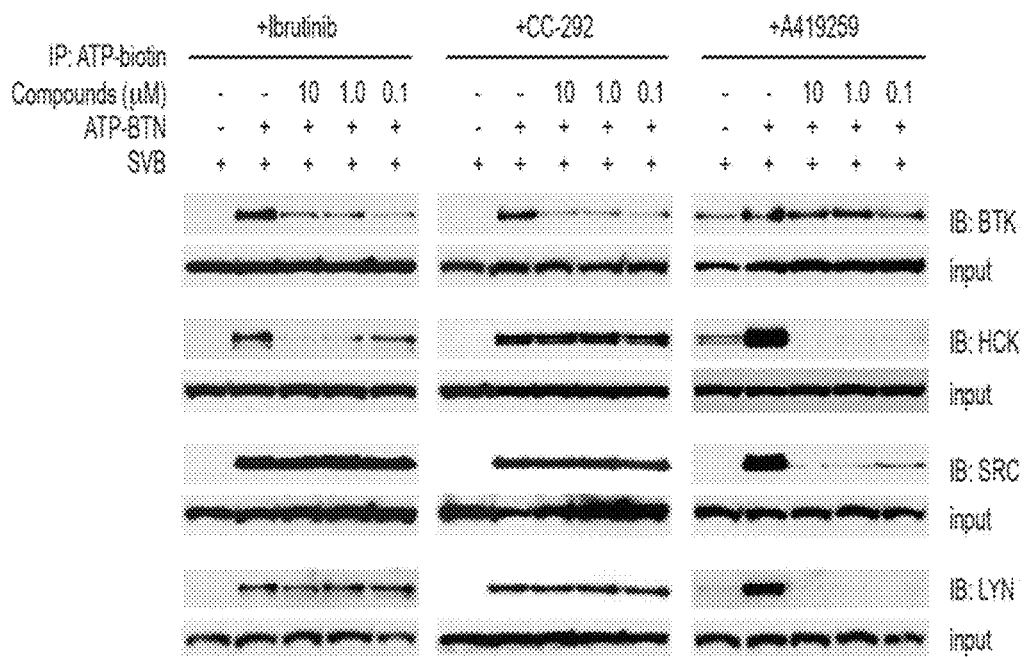

Kinase selectivity profiling has established that in addition to being a covalent inhibitor of BTK, ibrutinib is also a potent non-covalent inhibitor of several SRC family members including HCK, YES and LCK.[11] We focused our attention on investigating the potential functional significance of HCK to ibrutinib's pharmacology due to its structural similarity with A419259, a HCK inhibitor with established activity in murine tumor models.[16] Indeed both ibrutinib and A419259 were developed based on the 4-amino-5,7-substituted pyrrolopyrimidine scaffold of the classical SRC-family inhibitor: PP1.[26] To create a model for how ibrutinib might bind to HCK we performed a molecular docking studies of ibrutinib into the co-crystal structure of HCK with A419259 (RK-20449) (PDB 3VS3)[27] (FIG. 6A). As expected, the docking study predicts that ibrutinib recognizes the ATP-binding pocket of HCK with an almost identical pose as A419259 with a calculated affinity energy ($\Delta G$) of −10.5 kcal/mol. Similar to A419259, ibrutinib's 4-amino group, forms a H-bond to the carbonyl groups of the gatekeeper residue Thr$^{333}$ (Thr$^{338}$ based on c-SRC numbering)[16] and also with Glu$^{334}$ of HCK; its 3-nitrogen atom, as an H-bond acceptor, interacts with the backbone amino group of Met$^{336}$ of HCK (FIG. 6A). The 4-phenoxyphenyl substituent at 5-position of ibrutinib, which is also identical to the 5-substituent of A419259, extends into the inner ATP-hydrophobic pocket of HCK. The pyrrolidine group at the 7-position of ibrutinib, the only distinctive substituent protect kinases from subsequent labeling with a reactive ATP-biotin probe is determined.[29] Living cells were treated with either ibrutinib, CC-292 or A419259, followed by lysis treatment with ATP-biotin and western blotting for BTK, HCK and other SRC family kinases. Consistent with the biochemical kinase assays, Ibrutinib and A419259, but not CC-292 blocked ATP binding to HCK in a dose-dependent manner, while ibrutinib and CC-292 but not A419259 blocked ATP binding to BTK in BCWM.1 WM cells. Consistent with its known activity, A419259 also blocked ATP binding to the SRC family members SRC and LYN. Conversely, ibrutinib and CC-292 did not block ATP binding to either SRC or LYN (FIG. 6C).

KiNativ profiling was performed for A419259, Ibrutinib and CC-292 on LYN inhibition in two WM cell lines, BCWM.1 and MWCL-1. The results demonstrate engagement of LYN and SRC by A419259 in WM cell lines (Table 1). These results also suggest a biologically important role for LYN and SRC in Waldenstrom's Macroglobulinemia.

TABLE 1

KiNativ profiling for A419259, Ibrutinib and CC-292 on LYN inhibition

| Kinase | Reference | Description | Sequence | Labeling Site | A419259, 1 µM BCW M.1 | A419259, 1 µM MW CL-1 | Ibrutinib, 1 µM BCW M.1 | Ibrutinib, 1 µM MW CL-1 | CC-292, 1 µM BCW M.1 | CC-292, 1 µM MW CL-1 |
|---|---|---|---|---|---|---|---|---|---|---|
| LYN | UniRef 100_P0 7948 | Tyrosine-protein kinase Lyn n = 1 Tax = Homo sapiens RepID = LYN_HUMAN | VAVKTLKPGTMSVQA FLEEANLMK (SEQ ID NO: 5) | Lys1 | >99 | >99 | 60.5 | 80.6 | 15.7 | 14.2 |
| FYN, SRC, YES | UniRef 100_P0 6241 | Proto-oncogene tyrosine-protein kinase Fyn n = 2 Tax = Homo sapiens RepID = FYN_HUMAN | QGAKFPIKWTAPEAA LYGR (SEQ ID NO: 6) | Activation Loop | >99 | 98.1 | 63.4 | 72.1 | 10.5 | −0.4 |

Labeling Site Key
Lys1                    Conserved Lysine 1
Lys2                    Conserved Lysine 2
ATP Loop                ATP binding loop,
Activation Loop         Activation loop
ATP                     ATP site in non-canonical kinase (e.g. lipid kinase)
Protein Kinase Domain   Other lysine within kinase domain, possible not in ATP binding site
Other                   Labeling of residue outside of the protein kinase domain, possibly not in ATP binding site related to A419259, is predicted to interact with Ala$^{390}$, Asn$^{391}$ or Asp$^{404}$ of HCK, whereas the 7-substituent of A419259 protrudes outward the ATP-pocket and interacts with Asp$^{348}$ (FIG. 6A).

To confirm HCK target engagement in cells by ibrutinib, we synthesized a biotin modified version of ibrutinib. For comparative purposes we also prepared a biotin-modified version of CC-292, a pyrimidine-based covalent BTK inhibitor.[28] Both ibrutinib and CC-292 use an acrylamide-moiety to form a covalent bond to Cys$^{481}$ and are potent kinase inhibitors of BTK (reported apparent IC$_{50}$≤0.5 nM).[11,28] Ibrutinib reversibly inhibits the kinase activity of HCK with an IC$_{50}$ of 3.7 nM, while CC-292 is a very weak HCK inhibitor with an IC50 of 14.6 µM which is well above the observed physiological concentrations of this drug.[11,28] As expected, biotinylated ibrutinib and CC-292 pulled down BTK in mutated MYD88 expressing BCWM.1, MWCL-1 and TMD-8 cells demonstrating their ability to directly bind to BTK (FIG. 6B). Biotinylated ibrutinib, but not CC-292 pulled down HCK in MYD88 mutated BCWM.1, MWCL-1 and TMD-8 cells thereby confirming binding of ibrutinib to HCK (FIG. 6B).

To confirm target engagement in living cells, we performed KiNativ profiling where the ability of inhibitors to Furthermore, without wishing to be bound by theory, addition of LYN to HCK inhibition may be important for targeting B-cell malignancies. LYN is a component of B-cell receptor (BCR) signaling which may be involved in pro-growth and survival signaling in MYD88 as well as non-MYD88 mutated diseases, such as WM/LPL, ABC DLBCL, and CLL.

Figure 7A:
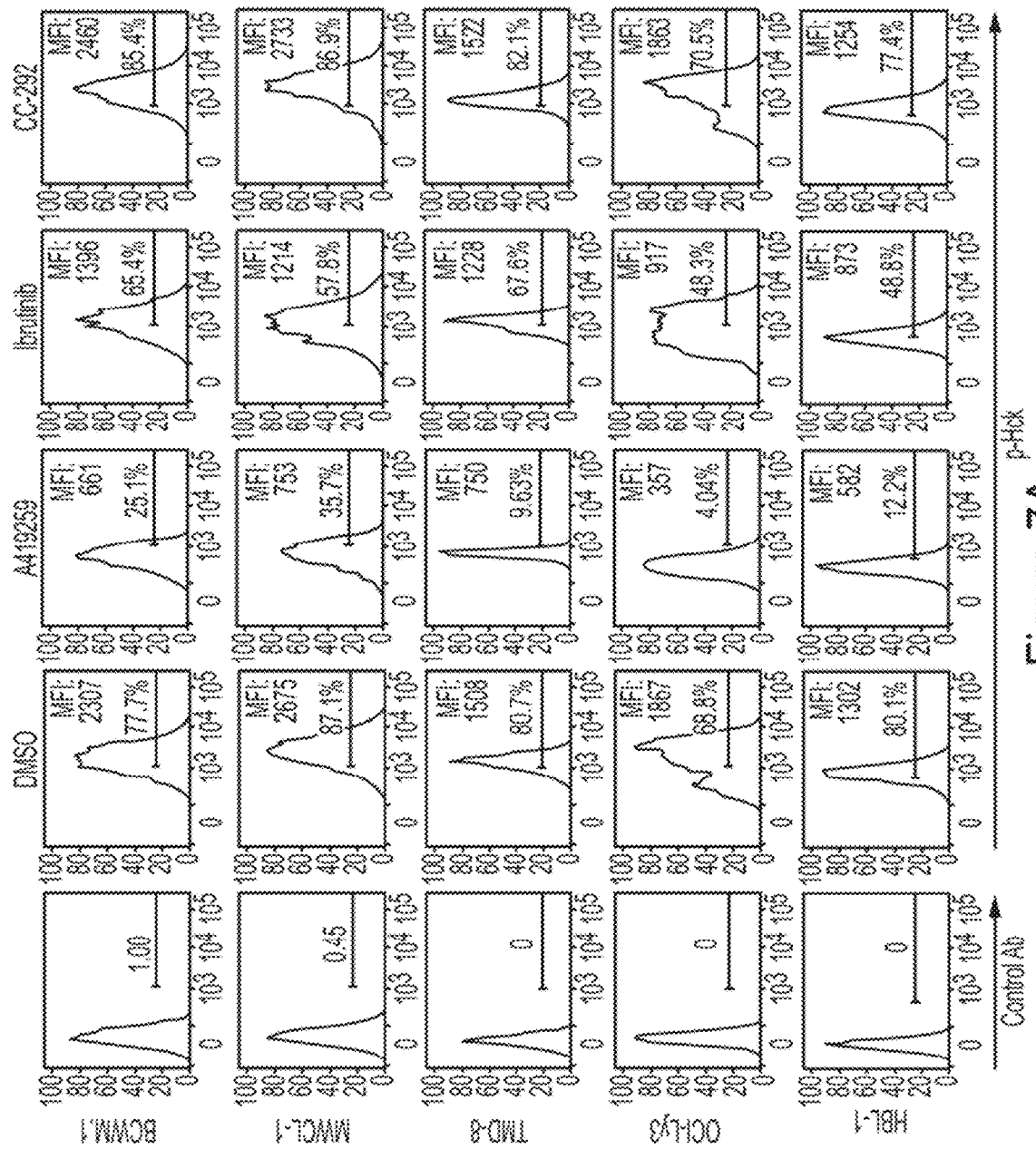
FIGS. 7A-7D show that HCK activity is blocked by A419259 and impacts survival of MYD88 mutated WM cells.
Figure 7A:
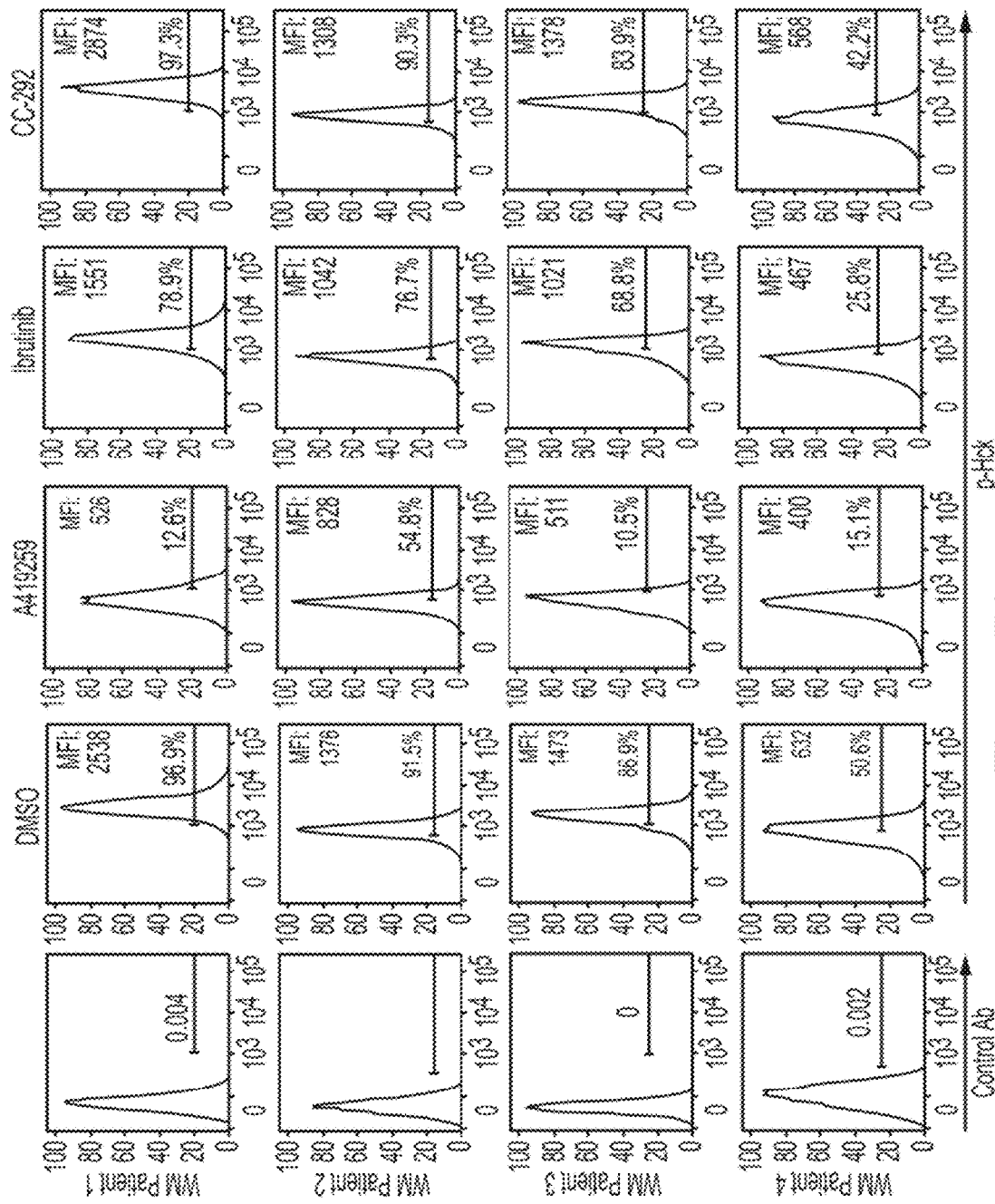
Figure 7B:
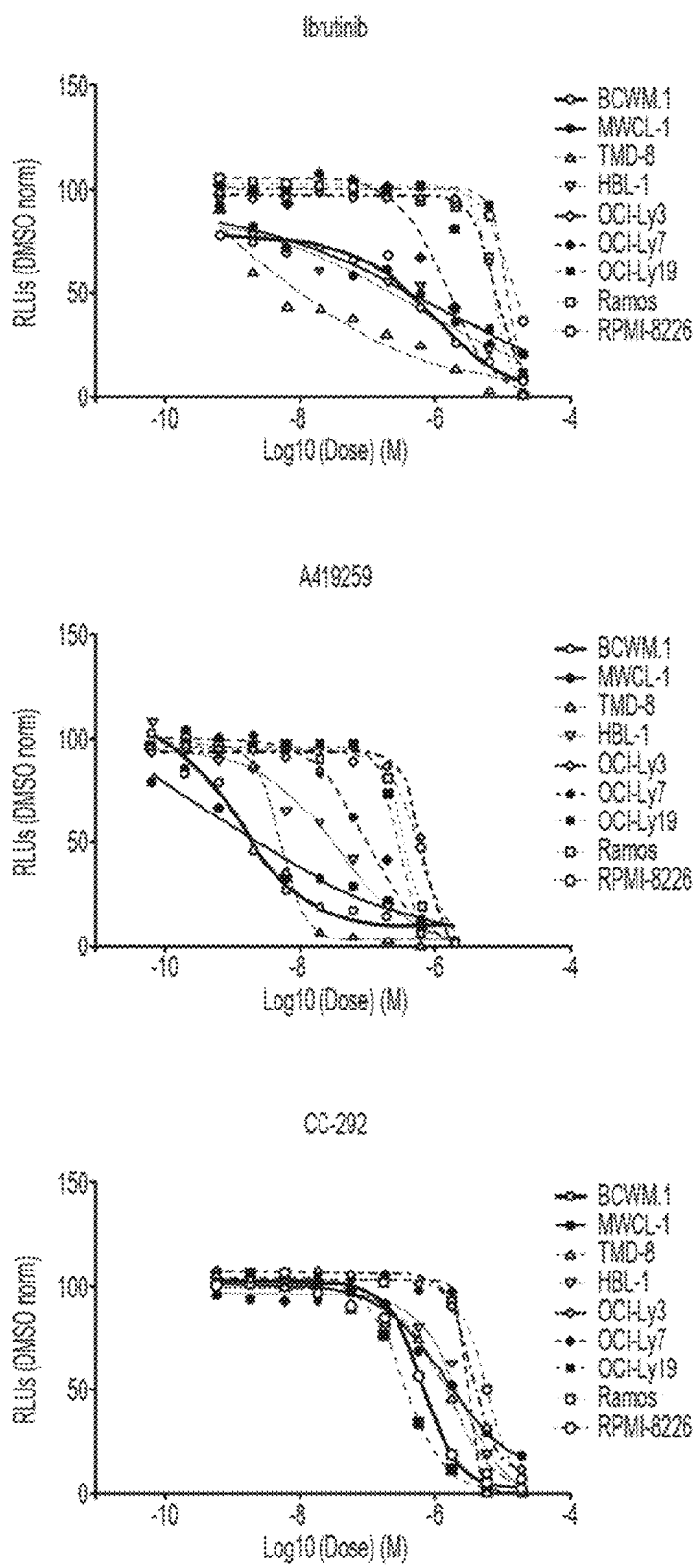
Figure 7C:
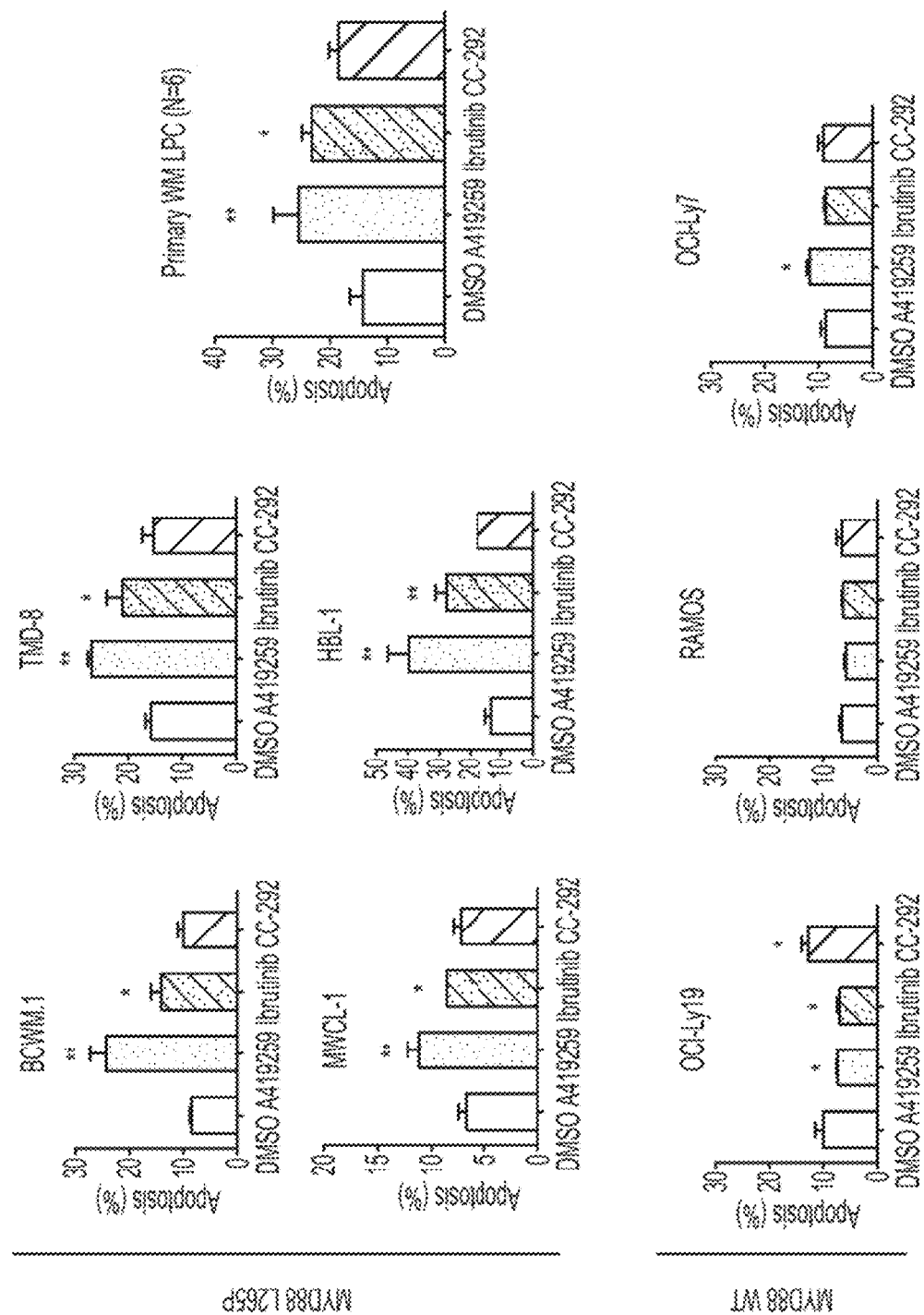
Figure 7D:
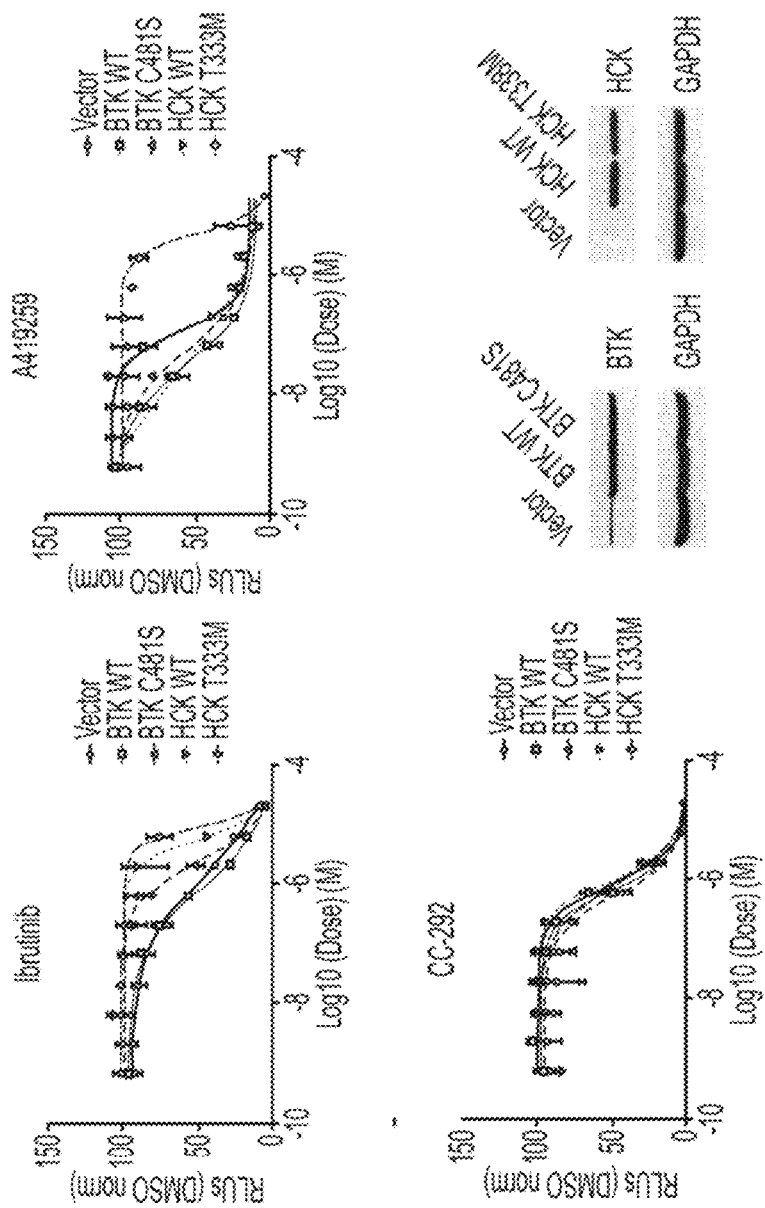

HCK Activity is Blocked by Ibrutinib and Impacts Survival of MYD88 Mutated WM Cells To assess the impact of ibrutinib and A419259 on HCK related activity in MYD88 mutated WM and ABC DLBCL tumor cells, we performed PhosFlow studies and assessed changes in HCK activation (Tyr$^{411}$). We also evaluated tumor cell viability by the CellTiter-Glo® Luminescent cell viability assay, and apoptosis by propidium iodide and Annexin V staining to determine if HCK inhibition contributed to WM cell death. We observed that ibrutinib, and even more so A419259, reduced HCK Tyr$^{411}$ phosphorylation in MYD88 L265P expressing WM and ABC DLBCL cell lines, as well as primary WM LPC. In contrast, CC-292 had little or no impact on HCK Tyr$^{411}$ phosphorylation (FIG. 7A). Decreased dose-dependent viability was also observed for ibrutinib and more so for A419259 that was more pronounced in mutated MYD88 expressing WM and ABC DLBCL cell lines, and primary WM cells versus MYD88$^{WT}$ cells (FIG. 7B). In contrast, the BTK inhibitor CC-292 that lacks HCK kinase inhibition showed higher EC$_{50}$ (>1 log-fold) for the mutated MYD88 cell lines, with the exception of OCI-Ly3 cells that carry a NF-κB activating CARD11 mutation.[5] Increased apoptotic changes were also observed in the mutated MYD88 cell lines and primary WM cells that showed decreased viability following ibrutinib, and more so A419259. In contrast, CC-292 had little or no impact on apoptosis in the mutated MYD88 cells (FIG. 7C). In as well, we observed little or no apoptotic activity for ibrutinib, A419259 or CC-292 apoptosis in MYD88$^{WT}$ cell lines or healthy donor B-cells (data not shown). To investigate whether ibrutinib or A419259 induced killing of WM cells was a consequence of BTK and/or HCK inhibition, we transduced MYD88$^{L265P}$ expressing BCWM.1 WM cells with a lentiviral control vector or vectors expressing wild-type BTK; BTK with a mutation of the cysteine required for irreversible inhibition (BTK$^{C481S}$); wild-type HCK; or HCK with the gatekeeper mutation Thr$^{333}$ (Thr$^{338}$ based on c-SRC numbering).16 Transduction of BCWM.1 WM cells with the BTK cysteine mutant (BTK$^{C481S}$) but not the vector control or wild-type BTK resulted in decreased ibrutinib and CC-292 mediated killing of BCWM.1 WM cells (<1 log-fold shift) (FIG. 7D). In contrast, treatment with HCK inhibitor A419259 showed no survival change versus vector control transduced cells (FIG. 7D).

Transduction of BCWM.1 WM cells with the HCK gatekeeper mutant (HCK$^{T333M}$; HCK$^{T338M}$ based on c-SRC numbering[16]) resulted in an >2 log-fold decrease in tumor cell killing. Over-expression of wild-type HCK also resulted in one log-fold decrease in ibrutinib mediated tumor cell killing when compared to control vector transduced BCWM.1 WM cells (FIG. 7D). Transduction of BCWM.1 cells with the HCK$^{T333M}$ gatekeeper mutant also contributed to a >2 log-fold decreased A419259 mediated tumor cell killing, while over-expression of wild-type HCK showed a one log-fold log decrease in WM cell killing (FIG. 7D). No substantial change in tumor cell killing following CC-292 treatment was observed in BCWM.1 cells transduced to express HCK$^{T333M}$ or wild-type HCK (FIG. 7D).

Figure 8A:
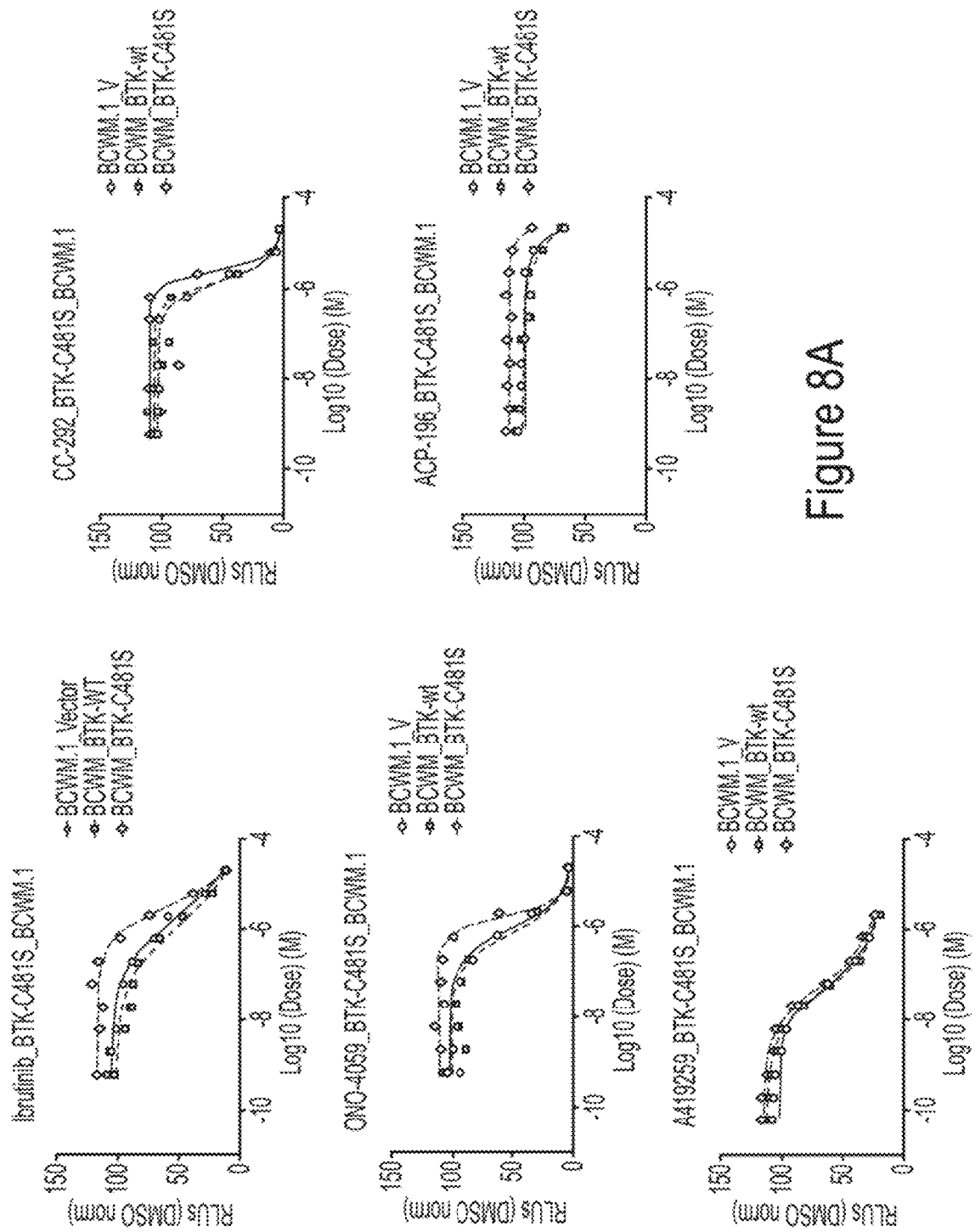
FIGS. 8A and 8B show that A419259 decreases cell viability in cells that are resistant to BTK inhibitors caused by BTK$^{C481S}$ mutation.
Figure 8B:
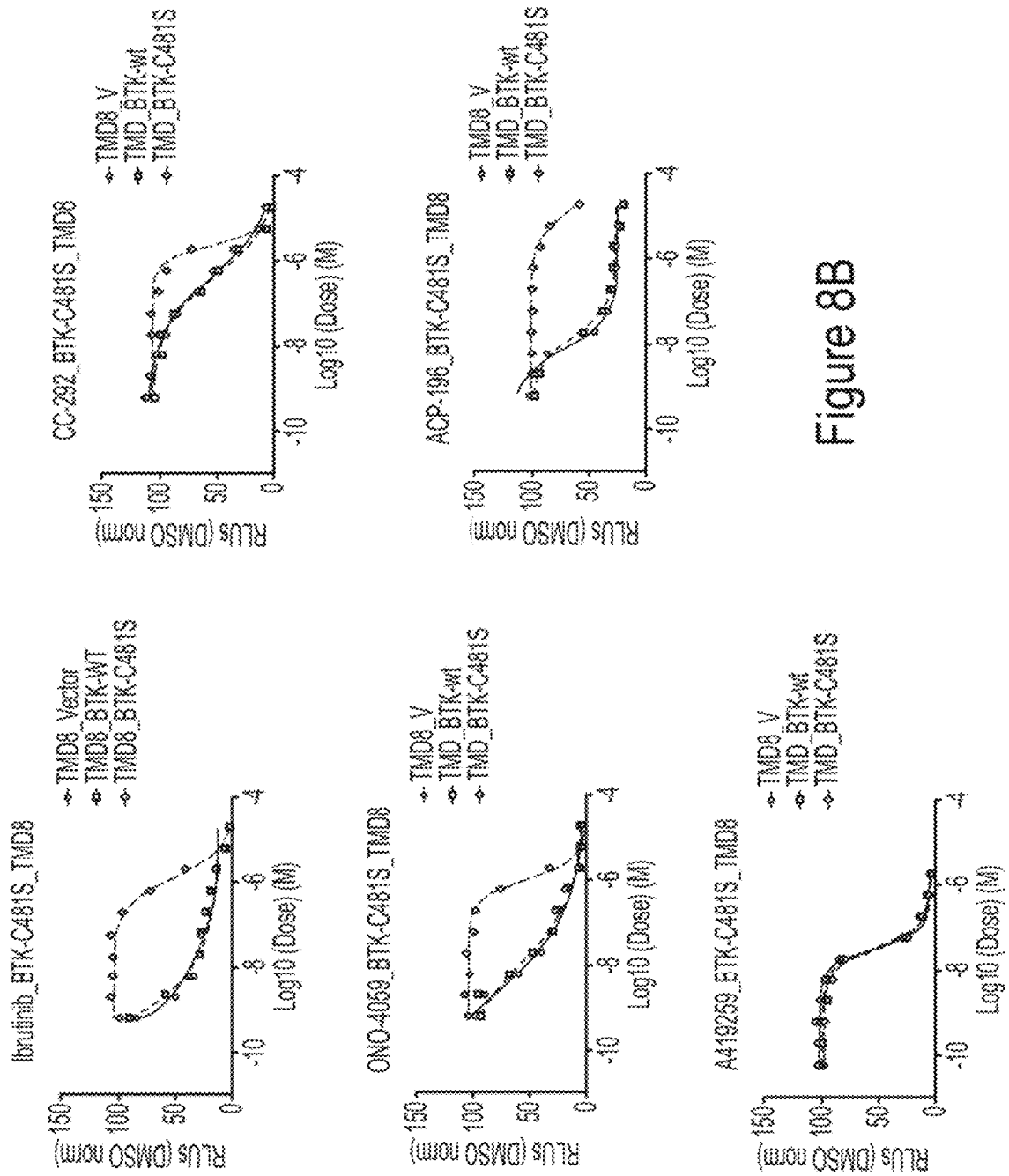

Similar findings were observed in an experiment in which BCWM.1 WM cells were transfected with wild-type BTK- or BTK$^{C481S}$-encoding vectors or a control vector, and treated with an HCK inhibitor A419259 or a BTK inhibitor, ibrutinib, CC-292, ONO-4059 or ACP-196. Measurement of cell viability for different doses of compounds are depicted in FIG. 8A. It was observed that BTK inhibitors ibrutinib, CC-292, ONO-4059 and ACP-196 showed a reduced potency in BTK$^{C481S}$ expressing cells compared to wild-type BTK expressing cells or cells transfected with the control vector. In contrast, HCK inhibitor A419259 did not show a decrease in its potency or efficacy for tumor cell killing in BTK$^{C481S}$ expressing cells compared to wild-type BTK expressing cells or cells transfected with the control vector (FIG. 8A). Similar results were observed when such an experiment was performed in the ABC DLBCL cell line TMD-8 (FIG. 8B). The BTK$^{C481S}$ mutation decreased the potency of the BTK inhibitors ibrutinib, CC-292, ONO-4059 and ACP-196 in killing tumor cells. A419259 showed no change in potency or efficacy for killing tumor cells compared to cells expression wild-type BTK or those transfected with the control vector (FIG. 8B).

These data support the use of HCK inhibitors, e.g., A419259, for the treatment of patients, including WM and/or ABC DLBCL patients that are resistant to BTK inhibitors (e.g., ibrutinib).

Example 2

Described below are experiments using cells derived from patients with WM and CLL that are resistant to ibrutinib treatment.

Figure 9:
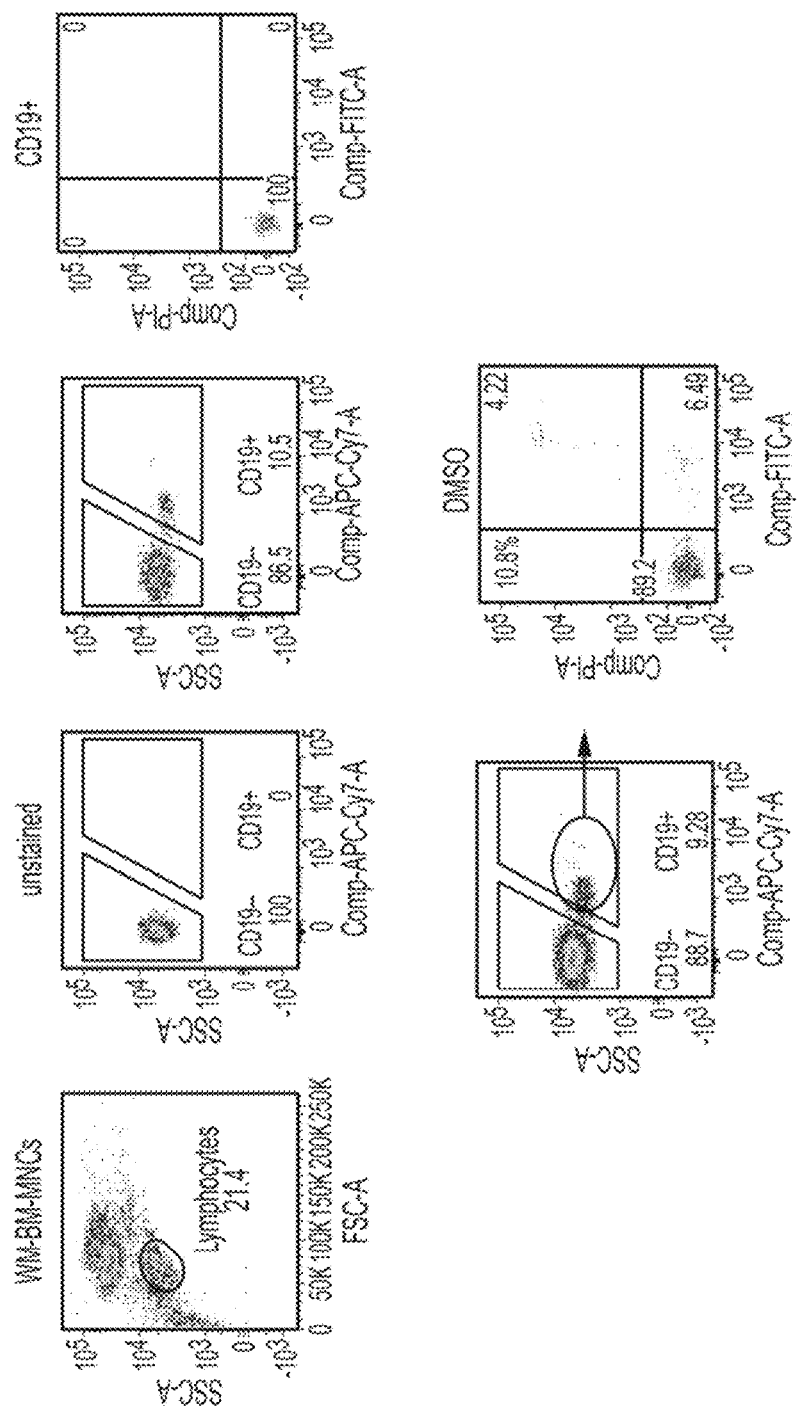
FIG. 9 shows that A419259 kills tumor cells isolated from a WM patient resistant to ibrutinib treatment. The figure shows analysis of apoptosis (indicated by the percentage) in CD19+ bone marrow cells after treatment with A419259, ibrutinib or DMSO (as a vehicle control).
Figure 9:
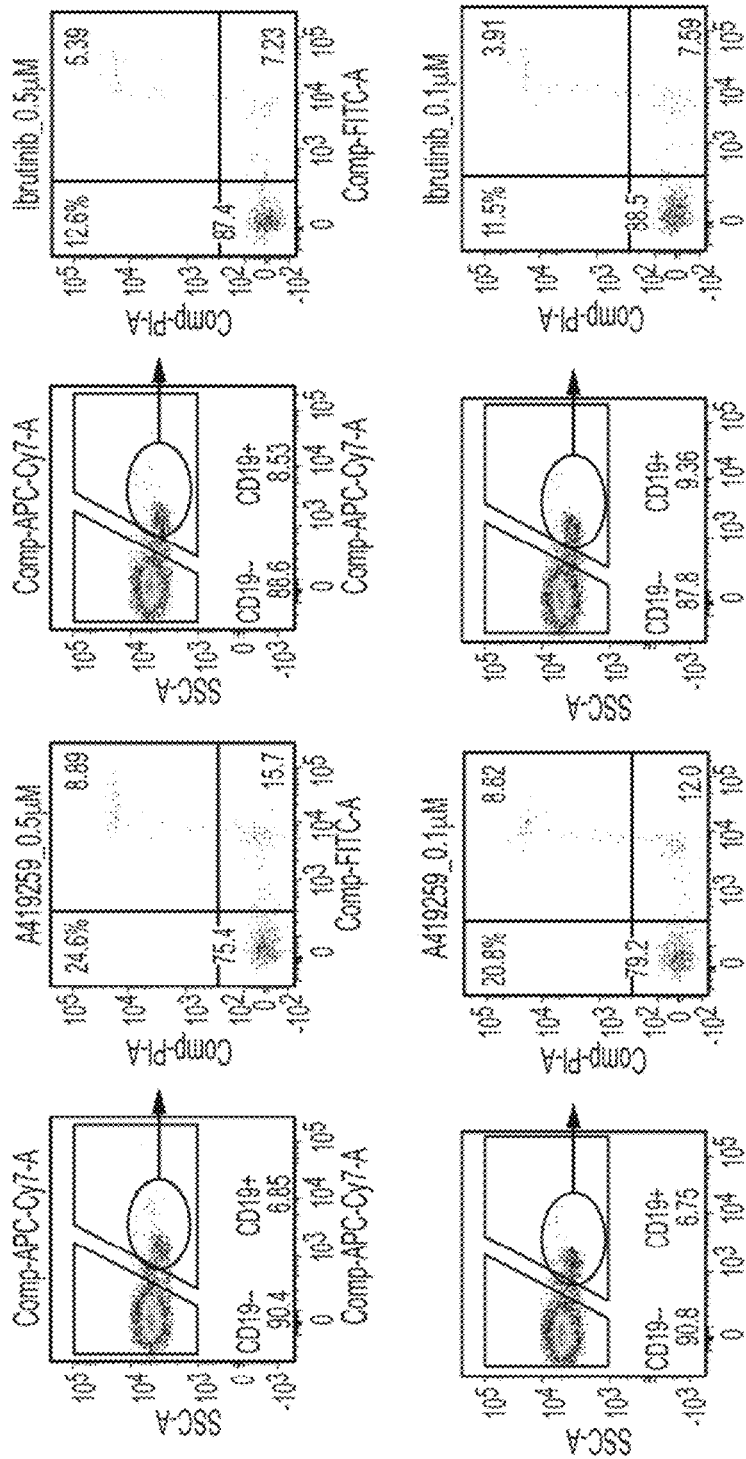
Figure 10:
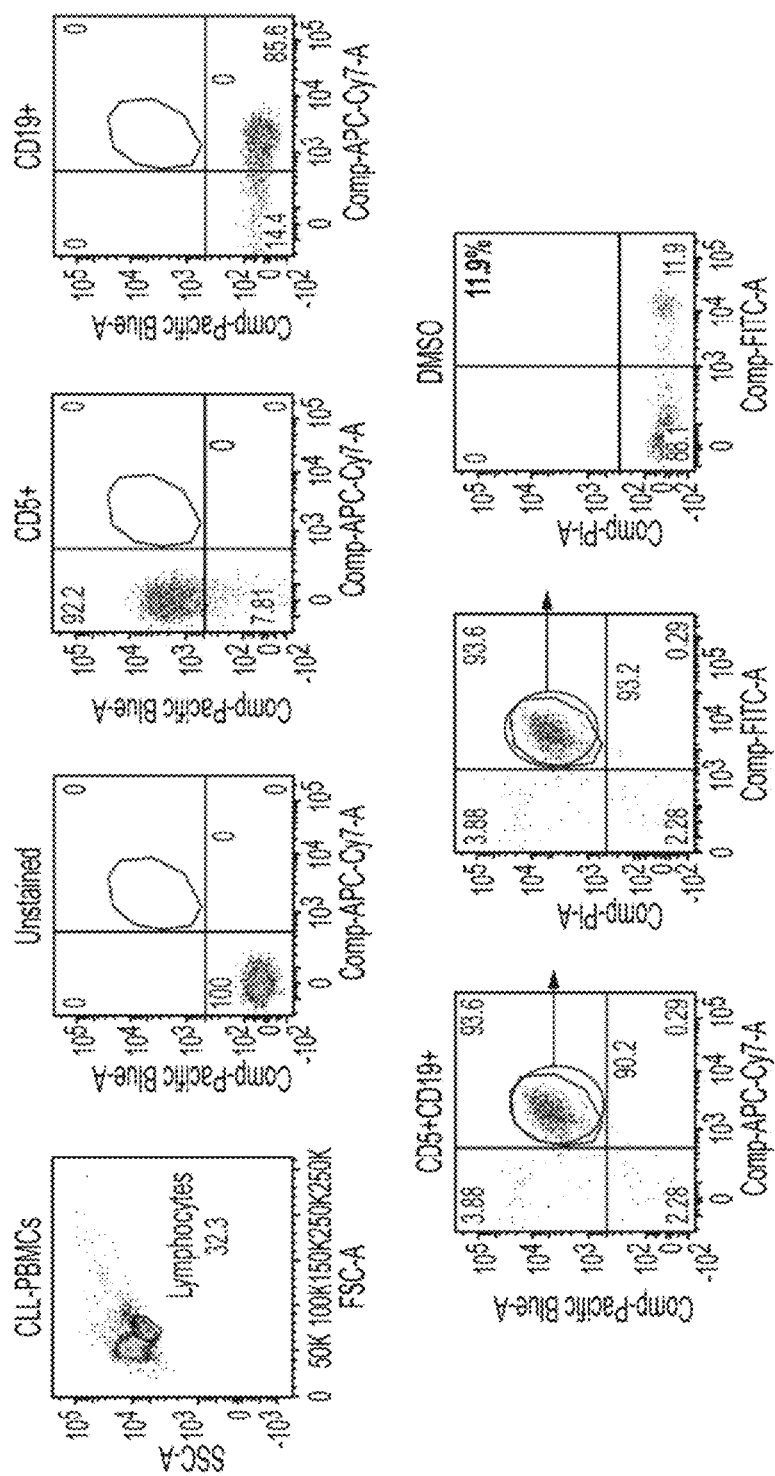
FIG. 10 shows that A419259 kills tumor cells isolated from a chronic lymphocytic leukemia (CLL) patient resistant to ibrutinib treatment. The figure shows analysis of apoptosis (indicated by the percentage) in CD5+CD19+ PBMC cells after treatment with A419259, ibrutinib or DMSO (as a vehicle control).
Figure 10:
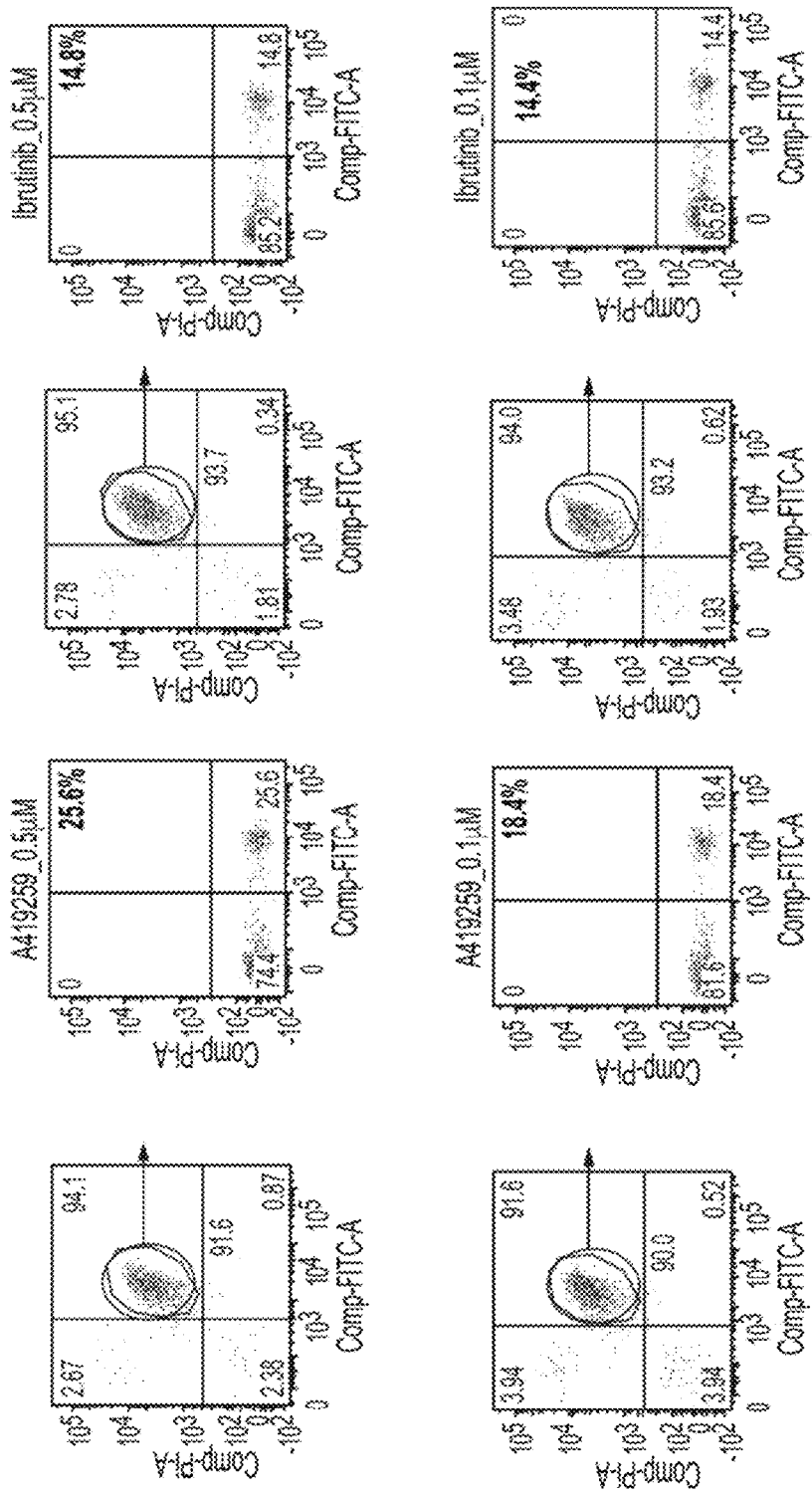

FIG. 9 describes data from an experiment in which CD19+ bone marrow cells were isolated from a WM patient resistant to ibrutinib, cultured, treated with A419259, ibrutinib or DMSO (as a vehicle control), and analyzed for percentage of apoptotic cells using flow cytometry. Treatment with 0.1 and 0.5 μM ibrutinib resulted in almost the same percentage of apoptotic cells as DMSO treatment. In contrast, treatment with 0.1 and 0.5 μM A419259 resulted in a substantially larger apoptotic cell population (20.8 and 24.6%, respectively).

In a similar ex vivo experiment using CD5+CD19+ PBMC cells isolated from a patient with CLL and resistant to ibrutinib treatment, DMSO treatment resulted in 11.9% apoptotic cells, and treatment with 0.1 and 0.5 μM ibrutinib resulted in 14.4 and 14.8% apoptotic cells, respectively. In comparison, treatment with 0.1 and 0.5 μM A419259 resulted in 18.4 and 25.6% apoptotic cells.

These data support the use of HCK inhibitors, e.g., A419259, for treating WM and CLL patients, including those who are resistant to treatment with BTK inhibitors such as ibrutinib.

REFERENCES

1. Treon S P, Xu L, Yang G, Zhou Y, Liu X, Cao Y, et al: MYD88 L265P somatic mutation in Waldenstrom's macroglobulinemia. N Engl J Med 2012; 367(15):826-33.2.
2. Xu L, Hunter Z, Yang G, Zhou Y, Cao Y, Liu X, et al. MYD88 L265P in Waldenstrom macroglobulinemia, immunoglobulin M monoclonal gammopathy, and other B-cell lymphoproliferative disorders using conventional and quantitative allele-specific polymerase chain reaction. Blood 2013; 121:2051-8.
3. Varettoni M, Arcaini L, Zibellini S, Boveri E, Rattotti S, Riboni R, et al. Prevalence and clinical significance of the MYD88 L265P somatic mutation in Waldenstrom macroglobulinemia, and related lymphoid neoplasms. Blood 2013; 121: 2522-8.
4. Treon S P, Xu L, Hunter Z R. MYD88 mutations and response to ibrutinib in Waldenstrom's Macroglobulinemia. N Engl J Med 2015; 373:584-6.
5. Ngo V N, Young R M, Schmitz R, Jhavar S, Xiao W, Lim K H, et al: Oncogenically active MYD88 mutations in human lymphoma. Nature 2011, 470:115-9.
6. Bohers E, Mareschal S, Bouzelfen A, Marchand V, Ruminy P, Maingonnat C, et al. Targetable activating mutations are very frequent in GCB and ABC Diffuse Large B-cell Lymphoma. Genes, Chromosomes, Cancer 2014; 53:144-153.
7. Yang G, Zhou Y, Liu X, Xu L, Cao Y, Manning R J, et al. A mutation in MYD88 (L265P) supports the survival of lymphoplasmacytic cells by activation of Bruton tyrosine kinase in Waldenstrom macroglobulinemia. Blood 2013; 122:1222-32.
8. Treon S P, Tripsas C K, Meid K, Warren D, Varma G, Green R, et al. Ibrutinib in previously treated Waldenstrom's Macroglobulinemia. N Engl J Med 2015; 372: 1430-40.
9. Treon S P, Xu L, Hunter Z R. MYD88 mutations and response to ibrutinib in Waldenstrom's Macroglobulinemia. N Engl J Med 2015; 373:584-6.

10. Wilson W H, Young R M, Schmitz R, Yang Y, Pittaluga S, Wright G, et al. Targeting B cell receptor signaling with ibrutinib in diffuse large B cell lymphoma. Nat Med 2015; 21:922-6.

11. Honigberg L A, Smith A M, Sirisawad M, Verner E, Loury D, Chang B, et al. The Bruton tyrosine kinase inhibitor PCI-32765 blocks B-cell activation and is efficacious in models of autoimmune disease and B-cell malignancy. Proc Natl Acad Sci USA 2010; 107:13075-80.

12. Gutiérrez N C, Ocio E M, de las Rivas J, Maiso P, Delgado M, Ferminan E, et al. Gene expression profiling of B lymphocytes and plasma cells from Waldenström's macroglobulinemia: comparison with expression patterns of the same cell counterparts from chronic lymphocytic leukemia, multiple myeloma and normal individuals. Leukemia 2007; 21:541-549.

13. Hallek M, Neumann C, Schäffer M, Danhauser-Riedl S, von Bubnoff N, de Vos G, et al. Signal transduction of interleukin-6 involves tyrosine phosphorylation of multiple cytosolic proteins and activation of Src-family kinases Fyn, Hck, and Lyn in multiple myeloma cell lines. Exp Hematol 1997; 25:1367-77.

14. Schaeffer M, Schneiderbauer M, Weidler S, Tavares R, Warmuth W, de Vos G, et al. Signaling through a novel domain of gp130 mediates cell proliferation and activation of Hck and Erk kinases. Mol Cell Biol 2001; 21:8068-81.

15. Leleu X, Jia X, Runnels J, Ngo H T, Moreau A S, Farag M, et al. The Akt pathway regulates survival and homing in Waldenstrom macroglobulinemia. Blood 2007; 110: 4417-26.

16. Pene-Dumitrescu T, Peterson L F, Donato N J, Smithgall T E. An inhibitor-resistant mutant of HCK protects CML cells against the anti-proliferative and apoptotic effects of the broad-spectrum SRC family kinase inhibitor A-419259. Oncogene 2008; 27:7055-69.

17. Sanner M F, Olson A J, Spehner J C. Reduced surface: an efficient way to compute molecular surfaces. Biopolymers 1996; 38: 305-20.

18. Trott O, Olson A J. AutoDock Vina: improving the speed and accuracy of docking with a new scoring function, efficient optimization, and multithreading. J Comput Chem 2010; 31: 455-61.

19. O'Boyle N M, Banck M, James C A, Morley C, Vandermeersch T, Hutchison G R. Open Babel: An open chemical toolbox. J Cheminform 2011; 3:33.

20. Sahota S S1, Babbage G, Weston-Bell N J. CD27 in defining memory B-cell origins in Waldenström's Macroglobulinemia. Clin. Lymphoma Myeloma 2009; 9:33-5.

21. Janz S. Waldenström Macroglobulinemia: Clinical and Immunological Aspects, Natural History, Cell of Origin, and Emerging Mouse Models. ISRN Hematol. 2013; 2013: 815325.

22. Cheng G, Ye Z S, Baltimore D. Binding of Bruton's tyrosine kinase to Fyn, Lyn, or Hck through a Src homology 3 domain-mediated interaction. Proc Natl Acad Sci USA 1994; 91(17):8152-5.

23. Hong H, Kitaura J, Xiao W, Horejsi V, Ra C, Lowell C A, et al. The Src family kinase Hck regulates mast cell activation by suppressing an inhibitory Src family kinase Lyn. Blood 2007; 110:2511-9.

24. Suh H S, Kim M O, Lee S C. Inhibition of granulocyte-macrophage colony-stimulating factor signaling and microglial proliferation by anti-CD45RO: role of Hck tyrosine kinase and phosphatidylinositol 3-kinase/Akt. J Immunol 2005; 174:2712-9.

25. Pecquet C, Nyga R, Penard-Lacronique V, Smithgail T E, Murakami H, Regnier A, et al. The Src tyrosine kinase Hck is required for Tel-Abl- but not for Tel-Jak2-induced cell transformation. Oncogene 2007; 26:1577-85.

26. Hanke J H, Gardner J P, Dow R L, Changelian P S, Brisette W H, Weringer E J, et al. Discovery of a novel, potent, and Src family-selective tyrosine kinase inhibitor. Study of Lck- and FynT-dependent T cell activation. J Biol Chem 1996; 271: 695-701.

27. Saito Y, Yuki H, Kuratani M, Hashizume Y, Takagi S, Tanaka A, et al. A pyrrolopyrimidine derivative targets human primary AML stem cells in vivo. Sci Transl Med. 2013; 5:181ra52.

28. Evans E K, Tester R, Aslanian S, Karp R, Sheets M, Labenski M T, et al. Inhibition of Btk with CC-292 provides early pharmacodynamic assessment of activity in mice and humans. J Pharmacol Exp Ther 2013; 346: 219-28.

29. Patricelli M P, Nomanbhoy T K, Wu J, Brown H, Zhou D, Zhang J, et al. In situ kinase profiling reveals functionally relevant properties of native kinases. Chem Biol. 2011; 18:699-710.

30. Taguchi T, Kiyokawa N, Sato N, Saito M, Fujimoto J. Characteristic expression of Hck in human B-cell precursors. Exp Hematol 2000; 28:55-64.

31. Jourdan M, Caraux A, Caron G, Robert N, Fiol G, Reme T, et al. Characterization of a transitional preplasmablast population in the process of human B cell to plasma cell differentiation. J Immunol 2011; 187:3931-41.

32. Cao Y, Hunter Z R, Liu X, Xu L, Yang G, Chen J, et al. The WHIM-like CXCR4$^{S338X}$ somatic mutation activates AKT and ERK, and promotes resistance to ibrutinib and other agents used in the treatment of Waldenstrom's Macroglobulinemia. Leukemia 2015; 29:169-76.

33. Cao Y, Hunter Z R, Liu X, Xu L, Yang G, Chen J, et al. CXCR4 WHIM-like frameshift and nonsense mutations promote ibrutinib resistance but do not supplant MYD88 L265P directed survival signaling in Waldenstrom Macroglobulinemia cells. Br J Haematol. 2015; 168:701-7.

34. Gay N J, Symmons M F, Gangloff M, Bryant C E. Assembly and localization of Toll-like receptor signalling complexes. Nat Reviews Immunol. 2014; 14:546-58.

35. Messeguer X, Escudero R, Farré D, Núñez O, Martínez J, AlbiàM M. PROMO: detection of known transcription regulatory elements using species-tailored searches. Bioinformatics. 2002; 18(2):333-4.

36. Farré D, Roset R, Huerta M, Adsuara J E, Roselló L, Albà M M, Messeguer X. Identification of patterns in biological sequences at the ALGGEN server: PROMO and MALGEN. Nucleic Acids Res. 2003; 31(13):3651-3.

37. Juilland M, Gonzalez M, Erdmann T, Banz Y, Jevnikar Z, Hailfinger S, et al. CARMA1- and MYD88-dependent activation of Jun/ATF-type AP-1 complexes is a hallmark of ABC diffuse large B-cell lymphomas. Blood 2016; an 8. pii: blood-2015-07-655647. [Epub ahead of print]

38. Chng W J, Schop R F, Price-Troska T, Ghobrial I, Kay N, Jelinek D F, et al. Gene-expression profiling of Waldenstrom macroglobulinemia reveals a phenotype more similar to chronic lymphocytic leukemia than multiple myeloma. Blood 2006; 108(8): 2755-63.

39. Lam L T, Wright G, Davis R E, Lenz G, Farinha P, Dang L, et al. Cooperative signaling through the signal transducer and activator of transcription 3 and nuclear factor-kappa B pathways in subtypes of diffuse large B-cell lymphoma. Blood 2008; 111:3701-13.

40. Advani R, Buggy J J, Sharman J P, Smith S M, Boyd T E, Grant B, et al. Bruton tyrosine kinase inhibitor ibrutinib 41. Woyach J A, Furman R R, Liu T M, Ozer H G, Zapatka M, Ruppert A S, et al. Resistance mechanisms for the Bruton's tyrosine kinase inhibitor ibrutinib. N Engl J Med 2014; 370:2286-94.
42. Musumeci F, Schenone S, Brullo C, Desoqus A, Botta L, Tinton C. HCK inhibitors as potential therapeutic agents in cancer and HIV infection. Curr Med Chem 2015; 22:1540-64.
43. Poh A R, O'Donoghue R J J, Ernst M. Hematopoeitic cell kinase (HCK) as a therapeutic target in immune and cancer cells. Oncotarget 2015; 6:15752-71.
44. Yang C, Lu P, Lee F Y, Chadburn A, Barrientos J C, Leonard J P, et al. Tyrosine kinase inhibition in diffuse large B-cell lymphoma: molecular basis for antitumor activity and drug resistance of dasatinib. Leukemia 2008; 22:1755-66.
45. Saijo K, Schmedt C, Su I H, Karasuyama H, Lowell C A, Reth M, Adachi T, Patke A, Santana A, Tarakhovsky A. Essential role of Src-family protein tyrosine kinases in NF-kappaB activation during B cell development. Nature immunology. 2003; 4:274-279.
46. Burger J A, Chiorazzi N. B cell receptor signaling in chronic lymphocytic leukemia. Trends Immunol. 2013; 34(12):592-601.
47. Argyropoulos K V, Vogel R, Ziegler C, Altan-Bonnet G, Velardi E, Calafiore M, Dogan A, Arcila M, Patel M, Knapp K, Mallek C, Hunter Z R, Treon S P, van den Brink M R, Palomba M L. Clonal B cells in Waldenström's macroglobulinemia exhibit functional features of chronic active B-cell receptor signaling. Leukemia. 2016 Feb. 12. doi: 10.1038/leu.2016.8. [Epub ahead of print]
48. Young R M, Wu T, Schmitz R, Dawood M, Xiao W, Phelan J D, Xu W, Menard L, Meffre E, Chan W C, Jaffe E S, Gascoyne R D, Campo E, Rosenwald A, Ott G, Delabie J, Rimsza L M, Staudt L M. Survival of human lymphoma cells requires B-cell receptor engagement by self-antigens. Proc Natl Acad Sci USA. 2015 Nov. 3; 112(44):13447-54. doi: 10.1073/pnas.1514944112. Epub 2015 Oct. 19.
49. Ngo H T1, Azab A K, Farag M, Jia X, Melhem M M, Runnels J, Roccaro A M, Azab F, Sacco A, Leleu X, Anderson K C, Ghobrial I M. Src tyrosine kinase regulates adhesion and chemotaxis in Waldenstrom macroglobulinemia. Clin Cancer Res. 2009 Oct. 1; 15(19):6035-41. doi: 10.1158/1078-0432.CCR-09-0718. Epub 2009 Sep. 15.

We claim:

1. A method of treating a subject comprising:
   administering to a subject with MYD88 mutated disease a pharmaceutical composition comprising a compound of the formula

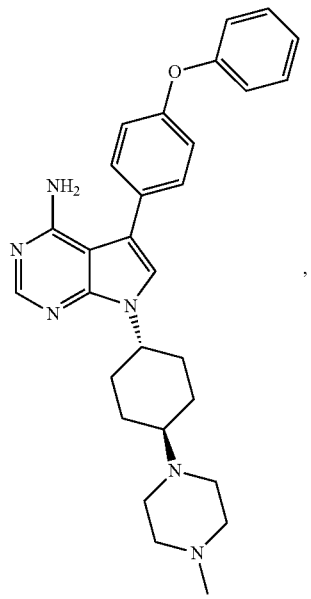 [SMILES: CN1CCN([C@H]2CC[C@H](n3cc(-c4ccc(Oc5ccccc5)cc4)c4c(N)ncnc43)CC2)CC1]

or a pharmaceutically acceptable salt thereof, wherein the MYD88 mutated disease is selected from Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, and immune privileged lymphomas.

2. The method of claim 1, wherein the mutation in the gene encoding MYD88 results in a single nucleotide change from T to C in the MYD88 gene.

3. The method of claim 1, wherein the mutation in the gene encoding MYD88 results in an amino acid change selected from V217F, W218R, I220T, S222R, M232T, S243N, L265P and T294P.

4. The method of claim 1, wherein the subject has been previously tested and is known to have a mutation in the gene encoding MYD88.

5. The method of claim 1, further comprising administering an anti-cancer agent, a proteasome inhibitor, a monoclonal antibody, an alkylator drug, a nucleoside analogue, an MTOR inhibitor, a BTK inhibitor, a BCR inhibitor and/or an immunomodulating agent to the subject.

6. The method of claim 5, wherein the anti-cancer agent is a chemotherapeutic agent.

7. The method of claim 1, further comprising administering an agent that blocks ATP binding to LYN.

8. The method of claim 1, further comprising administering an agent that blocks ATP binding to SRC.

9. A method of treating a subject comprising:
   performing an assay on a biological sample obtained from a subject in need thereof to determine whether the subject has a mutation in the gene encoding MYD88;
   if the subject has a mutation in the gene encoding MYD88, then administering to the subject a pharmaceutical composition comprising a compound of the formula

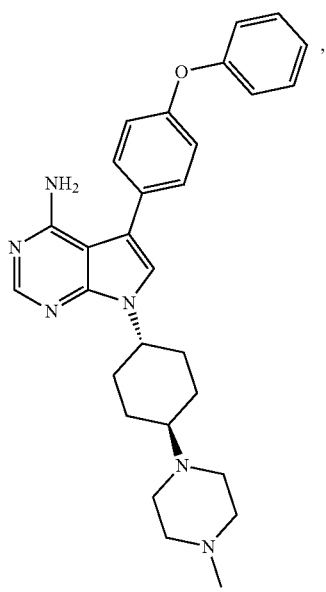 [SMILES: CN1CCN([C@H]2CC[C@H](n3cc(-c4ccc(Oc5ccccc5)cc4)c4c(N)ncnc43)CC2)CC1]

or a pharmaceutically acceptable salt thereof,
and wherein, if the subject has a mutation in the gene encoding MYD88, the subject has a MYD88 mutated disease selected from Waldenstrom's Macroglobulinemia (IgM secreting lymphoplasmacytic lymphoma), non-IgM secreting lymphoplasmacytic lymphoma, ABC subtype of diffuse large B-cell lymphoma, primary central nervous system (CNS) lymphoma, and immune privileged lymphomas.

10. The method of claim 1, wherein immune privileged lymphomas include testicular lymphoma, marginal zone lymphoma, and chronic lymphocytic leukemia.

11. The method of claim 9, wherein immune privileged lymphomas include testicular lymphoma, marginal zone lymphoma, and chronic lymphocytic leukemia.

12. The method of claim 1, wherein a pharmaceutically acceptable trihydrochloride salt of the compound is administered.

13. The method of claim 12, wherein the pharmaceutically acceptable trihydrochloride salt of the compound is A419259.

14. The method of claim 9, wherein a pharmaceutically acceptable trihydrochloride salt of the compound is administered.

15. The method of claim 14, wherein the pharmaceutically acceptable trihydrochloride salt of the compound is A419259.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gctgtgattt ggaagggaa                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
ggatagcgag accactaaa                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 3
ggagcaatat actatcata                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 4
ggaactgtct agtatctta                                              19

<210> SEQ ID NO 5
<211> LENGTH: 24
<212> TYPE: PRT
<213> ORGANISM: Homo sapiens

<400> SEQUENCE: 5

Val Ala Val Lys Thr Leu Lys Pro Gly Thr Met Ser Val Gln Ala Phe
1               5                   10                  15

Leu Glu Glu Ala Asn Leu Met Lys
            20

<210> SEQ ID NO 6
<211> LENGTH: 19
<212> TYPE: PRT
<213> ORGANISM: Homo sapiens

<400> SEQUENCE: 6

Gln Gly Ala Lys Phe Pro Ile Lys Trp Thr Ala Pro Glu Ala Ala Leu
1               5                   10                  15

Tyr Gly Arg
```